United States Patent
Chang et al.

(10) Patent No.: US 11,884,733 B2
(45) Date of Patent: Jan. 30, 2024

(54) ANTIBODY VARIABLE DOMAINS TARGETING THE NKG2D RECEPTOR

(71) Applicant: Dragonfly Therapeutics, Inc., Waltham, MA (US)

(72) Inventors: Gregory P. Chang, Medford, MA (US); Ann F. Cheung, Lincoln, MA (US); Asya Grinberg, Lexington, MA (US); William Haney, Wayland, MA (US); Bradley M. Lunde, Lebanon, NH (US); Bianka Prinz, Lebanon, NH (US)

(73) Assignee: Dragonfly Therapeutics, Inc., Waltham, MA (US)

( * ) Notice: Subject to any disclaimer, the term of this patent is extended or adjusted under 35 U.S.C. 154(b) by 775 days.

(21) Appl. No.: 16/967,216

(22) PCT Filed: Feb. 8, 2019

(86) PCT No.: PCT/US2019/017330
§ 371 (c)(1),
(2) Date: Aug. 4, 2020

(87) PCT Pub. No.: WO2019/157366
PCT Pub. Date: Aug. 15, 2019

(65) Prior Publication Data
US 2021/0054082 A1    Feb. 25, 2021

Related U.S. Application Data

(60) Provisional application No. 62/716,259, filed on Aug. 8, 2018, provisional application No. 62/628,161, filed on Feb. 8, 2018.

(51) Int. Cl.
| | | |
|---|---|---|
| *C07K 16/00* | (2006.01) | |
| *C12P 21/08* | (2006.01) | |
| *C07K 16/28* | (2006.01) | |
| *C07K 16/32* | (2006.01) | |

(52) U.S. Cl.
CPC ...... *C07K 16/2851* (2013.01); *C07K 16/2803* (2013.01); *C07K 16/283* (2013.01); *C07K 16/32* (2013.01); *C07K 2317/31* (2013.01); *C07K 2317/52* (2013.01); *C07K 2317/56* (2013.01); *C07K 2317/565* (2013.01); *C07K 2317/73* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | |
|---|---|---|
| 5,776,427 A | 7/1998 | Thorpe et al. |
| 5,807,706 A | 9/1998 | Carter et al. |
| 5,863,538 A | 1/1999 | Thorpe et al. |
| 5,959,084 A | 9/1999 | Ring et al. |
| 6,036,955 A | 3/2000 | Thorpe et al. |
| 6,054,297 A | 4/2000 | Carter et al. |
| 6,129,914 A | 10/2000 | Weiner et al. |
| 6,165,464 A | 12/2000 | Hudziak et al. |
| 6,210,670 B1 | 4/2001 | Berg |
| 6,294,167 B1 | 9/2001 | Lindhofer et al. |
| 6,387,371 B1 | 5/2002 | Hudziak et al. |
| 6,399,063 B1 | 6/2002 | Hudziak et al. |
| 6,407,213 B1 | 6/2002 | Carter et al. |
| 6,572,856 B1 | 6/2003 | Taylor et al. |
| 6,737,056 B1 | 5/2004 | Presta |
| 7,112,324 B1 | 9/2006 | Dorken et al. |
| 7,235,641 B2 | 6/2007 | Kufer et al. |
| 7,575,923 B2 | 8/2009 | Dorken et al. |
| 7,635,472 B2 | 12/2009 | Kufer et al. |
| 7,642,228 B2 | 1/2010 | Carter et al. |
| 7,695,936 B2 | 4/2010 | Carter et al. |
| 7,820,166 B2 | 10/2010 | Lanzavecchia |
| 7,879,985 B2 | 2/2011 | Urso et al. |
| 7,951,917 B1 | 5/2011 | Arathoon et al. |
| 8,007,796 B2 | 8/2011 | Baeuerle et al. |
| 8,076,459 B2 | 12/2011 | Hofmeister et al. |
| 8,101,722 B2 | 1/2012 | Kufer et al. |
| 8,236,308 B2 | 8/2012 | Kischel et al. |
| 8,409,577 B2 | 4/2013 | Thompson et al. |
| 8,518,403 B2 | 8/2013 | Hoffmann et al. |

(Continued)

FOREIGN PATENT DOCUMENTS

| | | |
|---|---|---|
| CA | 2990511 A1 | 12/2016 |
| CN | 102378768 A | 3/2012 |

(Continued)

OTHER PUBLICATIONS

Felices et al. (2016) "Generation of BiKEs and TriKEs to Improve NK cell-Mediated Targeting of Tumor Cells," Natural Killer Cells: Methods and Protocols, Methods in Molecular Biology 1441:333-346.
Gantke et al. (2016) "Trispecific Antibodies for Selective CD16A-Directed NK-Cell Engagement in Multiple Myeloma," Blood 128(22):4513.
Gantke et al. (2017) "Trispecific antibodies for CD16A-directed NK cell engagement and dual-targeting of tumor cells," Protein Engineering, Design & Selection 38(9):673-684.
Gauthier et al. (2019) "Multifunctional Natural Killer Cell Engagers Targeting NKp46 Trigger Protective Tumor Immunity," Cell 177(7):1701-1713.
Gooden et al. (2012) "Infiltrating CTLs are bothered by HLA-E on tumors," OncoImmunology, 1(1):92-93.

(Continued)

*Primary Examiner* — Chun W Dahle
(74) *Attorney, Agent, or Firm* — Goodwin Procter LLP

(57) ABSTRACT

Antibody heavy chain variable domains that can be paired with antibody light chain variable domains to form an antigen-binding site targeting the NKG2D receptor on natural killer cells are described. Proteins comprising an NKG2D antigen-binding site, pharmaceutical compositions and therapeutic methods thereof, including for the treatment of cancer, are also described.

14 Claims, 19 Drawing Sheets

Specification includes a Sequence Listing.

(56) References Cited

U.S. PATENT DOCUMENTS

| | | |
|---|---|---|
| 8,591,897 B2 | 11/2013 | Bryant |
| 8,658,765 B2 | 2/2014 | Martin, Jr. et al. |
| 8,759,494 B2 | 6/2014 | Bachmann et al. |
| 8,784,821 B1 | 7/2014 | Kufer et al. |
| 8,796,420 B2 | 8/2014 | Martin, Jr. et al. |
| 8,840,888 B2 | 9/2014 | Nagorsen et al. |
| 9,079,969 B2 | 7/2015 | Martin, Jr. et al. |
| 9,102,736 B2 | 8/2015 | Hofmeister et al. |
| 9,127,064 B2 | 9/2015 | Urso et al. |
| 9,150,656 B2 | 10/2015 | Johnson et al. |
| 9,150,663 B2 | 10/2015 | Labrijn et al. |
| 9,200,078 B2 | 12/2015 | Bachmann |
| 9,248,181 B2 | 2/2016 | De Kruif et al. |
| 9,248,182 B2 | 2/2016 | De Kruif et al. |
| 9,273,136 B2 | 3/2016 | Rader et al. |
| 9,493,578 B2 | 11/2016 | Lazar et al. |
| 9,562,109 B2 | 2/2017 | Von Kreudenstein et al. |
| 9,587,036 B2 | 3/2017 | Kufer et al. |
| 9,637,557 B2 | 5/2017 | Scheer et al. |
| 9,683,053 B2 | 6/2017 | Blein et al. |
| 9,690,969 B2 | 6/2017 | Okamoto |
| 9,718,893 B2 | 8/2017 | Jung et al. |
| 9,951,145 B2 | 4/2018 | Kim et al. |
| 9,963,513 B2 | 5/2018 | Vu et al. |
| 10,040,853 B2 | 8/2018 | Spies et al. |
| 10,047,167 B2 | 8/2018 | Demarest et al. |
| 10,059,765 B2 | 8/2018 | Velardi et al. |
| 10,377,827 B2 | 8/2019 | Swanson et al. |
| 10,526,409 B2 | 1/2020 | Urso et al. |
| 11,124,582 B2 | 9/2021 | Ambrogelly et al. |
| 2002/0103345 A1 | 8/2002 | Zhu |
| 2002/0193569 A1 | 12/2002 | Hanna |
| 2004/0038339 A1 | 2/2004 | Kufer et al. |
| 2004/0052783 A1 | 3/2004 | Weiner et al. |
| 2004/0115198 A1 | 6/2004 | Spies et al. |
| 2005/0037002 A1 | 2/2005 | Velardi et al. |
| 2005/0054019 A1 | 3/2005 | Michaud et al. |
| 2005/0058639 A1 | 3/2005 | Gudas et al. |
| 2005/0158307 A1 | 7/2005 | Spies et al. |
| 2005/0244416 A1 | 11/2005 | Jung |
| 2006/0018899 A1 | 1/2006 | Kao et al. |
| 2006/0235201 A1 | 10/2006 | Kischel |
| 2006/0246004 A1 | 11/2006 | Adams et al. |
| 2007/0004909 A1 | 1/2007 | Johnson et al. |
| 2007/0071759 A1 | 3/2007 | Shin et al. |
| 2007/0179086 A1 | 8/2007 | Gliniak et al. |
| 2007/0190063 A1 | 8/2007 | Bahjat et al. |
| 2008/0025975 A1 | 1/2008 | Weiner et al. |
| 2008/0299137 A1 | 12/2008 | Svendsen et al. |
| 2008/0305105 A1 | 12/2008 | Kufer et al. |
| 2009/0142352 A1 | 6/2009 | Jackson et al. |
| 2009/0175867 A1 | 7/2009 | Thompson et al. |
| 2009/0226442 A1 | 9/2009 | Huet et al. |
| 2009/0226466 A1 | 9/2009 | Fong et al. |
| 2009/0252729 A1 | 10/2009 | Farrington et al. |
| 2009/0304693 A1 | 12/2009 | Ghayur et al. |
| 2009/0304696 A1 | 12/2009 | Lawson et al. |
| 2010/0009866 A1 | 1/2010 | Prinz et al. |
| 2010/0055034 A1 | 3/2010 | Martin et al. |
| 2010/0056764 A1 | 3/2010 | Urso et al. |
| 2010/0124764 A1 | 5/2010 | Hufton et al. |
| 2010/0174053 A1 | 7/2010 | Johnson et al. |
| 2010/0178298 A1 | 7/2010 | Lindhofer |
| 2010/0260765 A1 | 10/2010 | Barry et al. |
| 2010/0272718 A1 | 10/2010 | Urso et al. |
| 2010/0286374 A1 | 11/2010 | Kannan et al. |
| 2010/0291112 A1 | 11/2010 | Kellner et al. |
| 2011/0008335 A1 | 1/2011 | Velardi et al. |
| 2011/0020273 A1 | 1/2011 | Chang et al. |
| 2011/0044980 A1 | 2/2011 | Ghayur et al. |
| 2011/0054151 A1 | 3/2011 | Lazar et al. |
| 2011/0150870 A1 | 6/2011 | Rader et al. |
| 2011/0311535 A1 | 12/2011 | Dranoff et al. |
| 2012/0014957 A1 | 1/2012 | Ghayur et al. |
| 2012/0058082 A1 | 3/2012 | Kaplan et al. |
| 2012/0058906 A1 | 3/2012 | Smider et al. |
| 2012/0093823 A1 | 4/2012 | Van Den Brink et al. |
| 2012/0149876 A1 | 6/2012 | Von Kreudenstein et al. |
| 2012/0171173 A1 | 7/2012 | Ideno et al. |
| 2012/0195900 A1 | 8/2012 | Ghayur et al. |
| 2012/0263722 A1 | 10/2012 | Ghayur et al. |
| 2012/0269723 A1 | 10/2012 | Brinkmann et al. |
| 2012/0294796 A1 | 11/2012 | Johnson et al. |
| 2012/0294857 A1 | 11/2012 | Sentman et al. |
| 2012/0321626 A1 | 12/2012 | Zhou |
| 2012/0328619 A1 | 12/2012 | Fey et al. |
| 2013/0115208 A1 | 5/2013 | Ho et al. |
| 2013/0177555 A1 | 7/2013 | Wilkinson et al. |
| 2013/0209514 A1 | 8/2013 | Gilboa et al. |
| 2013/0216528 A1 | 8/2013 | Cheung et al. |
| 2013/0216544 A1 | 8/2013 | Bachmann |
| 2013/0230525 A1 | 9/2013 | Li et al. |
| 2013/0336977 A1 | 12/2013 | Thompson et al. |
| 2014/0044739 A1 | 2/2014 | Teng et al. |
| 2014/0072579 A1 | 3/2014 | De Kruif et al. |
| 2014/0072581 A1 | 3/2014 | Dixit et al. |
| 2014/0105889 A1 | 4/2014 | Igawa et al. |
| 2014/0112926 A1 | 4/2014 | Liu et al. |
| 2014/0120096 A1 | 5/2014 | Bakker et al. |
| 2014/0127203 A1 | 5/2014 | Thompson et al. |
| 2014/0140999 A1 | 5/2014 | De Kruif et al. |
| 2014/0141022 A1 | 5/2014 | Thompson et al. |
| 2014/0154250 A1 | 6/2014 | Thompson et al. |
| 2014/0154252 A1 | 6/2014 | Thompson et al. |
| 2014/0199294 A1 | 7/2014 | Mimoto et al. |
| 2014/0234342 A1 | 8/2014 | Narni-Mancinelli et al. |
| 2014/0242077 A1 | 8/2014 | Choi et al. |
| 2014/0271617 A1 | 9/2014 | Igawa et al. |
| 2014/0288275 A1 | 9/2014 | Moore et al. |
| 2014/0294827 A1 | 10/2014 | Gastwirt et al. |
| 2014/0302064 A1 | 10/2014 | Moore |
| 2014/0363426 A1 | 12/2014 | Moore et al. |
| 2014/0364340 A1 | 12/2014 | Vasquez et al. |
| 2015/0050269 A1 | 2/2015 | Igawa et al. |
| 2015/0056206 A1 | 2/2015 | Zhou |
| 2015/0079088 A1 | 3/2015 | Lowman et al. |
| 2015/0119555 A1 | 4/2015 | Jung et al. |
| 2015/0166636 A1 | 6/2015 | Igawa et al. |
| 2015/0166654 A1 | 6/2015 | Igawa et al. |
| 2015/0175697 A1 | 6/2015 | Bonvini et al. |
| 2015/0175700 A1 | 6/2015 | Lum et al. |
| 2015/0203591 A1 | 7/2015 | Yancopoulos et al. |
| 2015/0210765 A1 | 7/2015 | Roschke et al. |
| 2015/0259431 A1 | 9/2015 | Stemmer et al. |
| 2015/0259434 A1 | 9/2015 | Johnson et al. |
| 2015/0274838 A1 | 10/2015 | Johnson et al. |
| 2015/0299319 A1 | 10/2015 | Velardi et al. |
| 2015/0307617 A1 | 10/2015 | Du et al. |
| 2015/0307628 A1 | 10/2015 | Kim et al. |
| 2015/0329637 A1 | 11/2015 | Urech et al. |
| 2015/0353636 A1 | 12/2015 | Parren et al. |
| 2016/0017038 A1 | 1/2016 | Koenig |
| 2016/0024214 A1 | 1/2016 | Urso et al. |
| 2016/0032009 A1 | 2/2016 | Cheung et al. |
| 2016/0039942 A1 | 2/2016 | Cobbold et al. |
| 2016/0046727 A1 | 2/2016 | Labrijn et al. |
| 2016/0046730 A1 | 2/2016 | Ghayur et al. |
| 2016/0077105 A1 | 3/2016 | Bobrowicz et al. |
| 2016/0090426 A1 | 3/2016 | Zhou et al. |
| 2016/0096892 A1 | 4/2016 | Brogdon et al. |
| 2016/0122432 A1 | 5/2016 | Baty et al. |
| 2016/0159882 A1 | 6/2016 | Landgraf et al. |
| 2016/0159924 A1 | 6/2016 | Padkjaer et al. |
| 2016/0176968 A1 | 6/2016 | Chang et al. |
| 2016/0289341 A1 | 10/2016 | Wu |
| 2016/0326249 A1 | 11/2016 | Ng et al. |
| 2016/0347849 A1 | 12/2016 | Cai et al. |
| 2016/0369002 A1 | 12/2016 | Gauthier et al. |
| 2017/0022291 A1 | 1/2017 | Baruah et al. |
| 2017/0029529 A1 | 2/2017 | Croasdale et al. |
| 2017/0066827 A1 | 3/2017 | Pule et al. |
| 2017/0114141 A1 | 4/2017 | Amann et al. |
| 2017/0233472 A1 | 8/2017 | Barat et al. |
| 2017/0291955 A1 | 10/2017 | Li et al. |

(56) References Cited

U.S. PATENT DOCUMENTS

| | | | |
|---|---|---|---|
| 2017/0362321 A1 | 12/2017 | Campbell et al. | |
| 2017/0368169 A1 | 12/2017 | Loew et al. | |
| 2017/0369595 A1 | 12/2017 | Brinkmann et al. | |
| 2018/0044415 A1 | 2/2018 | Escarpe et al. | |
| 2018/0057608 A1 | 3/2018 | Jung et al. | |
| 2018/0105594 A1 | 4/2018 | Urso et al. | |
| 2018/0105599 A1 | 4/2018 | Cobbold et al. | |
| 2018/0118851 A1 | 5/2018 | Comeau et al. | |
| 2018/0237519 A1 | 8/2018 | Caligiuri et al. | |
| 2018/0273633 A1 | 9/2018 | Jiang et al. | |
| 2018/0312592 A1 | 11/2018 | Junutula et al. | |
| 2019/0048079 A1 | 2/2019 | Spies et al. | |
| 2019/0225702 A1 | 7/2019 | Baeuerle et al. | |
| 2019/0359716 A1 | 11/2019 | Chang et al. | |
| 2019/0375838 A1* | 12/2019 | Chang | C07K 16/2878 |
| 2020/0002436 A1 | 1/2020 | Chang et al. | |
| 2020/0024353 A1 | 1/2020 | Chang et al. | |
| 2020/0048347 A1 | 2/2020 | Miao et al. | |
| 2020/0055939 A1 | 2/2020 | Lombana et al. | |
| 2020/0095327 A1 | 3/2020 | Chang et al. | |
| 2020/0157174 A1 | 5/2020 | Chang et al. | |
| 2020/0157226 A1 | 5/2020 | Chang et al. | |
| 2020/0157227 A1 | 5/2020 | Chang et al. | |
| 2020/0165344 A1 | 5/2020 | Chang et al. | |
| 2020/0216544 A1 | 7/2020 | Chang et al. | |
| 2020/0231678 A1 | 7/2020 | Chang et al. | |
| 2020/0231679 A1 | 7/2020 | Chang et al. | |
| 2020/0231700 A1 | 7/2020 | Cheung et al. | |
| 2020/0277383 A1 | 9/2020 | Chang et al. | |
| 2020/0277384 A1 | 9/2020 | Chang et al. | |
| 2020/0376034 A1 | 12/2020 | Chang et al. | |
| 2021/0009718 A1 | 1/2021 | Ambrogelly et al. | |
| 2021/0032349 A1 | 2/2021 | Dengl et al. | |
| 2021/0054082 A1 | 2/2021 | Chang et al. | |
| 2021/0070887 A1 | 3/2021 | Ambrogelly et al. | |
| 2021/0079102 A1 | 3/2021 | Chang et al. | |
| 2021/0101976 A1 | 4/2021 | Chang et al. | |
| 2021/0130471 A1 | 5/2021 | Chang et al. | |
| 2021/0130474 A1 | 5/2021 | Chang et al. | |
| 2021/0130496 A1 | 5/2021 | Chang et al. | |
| 2021/0198369 A1 | 7/2021 | Chang et al. | |
| 2021/0206859 A1 | 7/2021 | Chang et al. | |
| 2021/0214436 A1 | 7/2021 | Chang et al. | |
| 2021/0221894 A1 | 7/2021 | Bigelow et al. | |
| 2021/0238290 A1 | 8/2021 | Chang et al. | |
| 2021/0261668 A1 | 8/2021 | Chang et al. | |
| 2021/0292420 A1 | 9/2021 | Chang et al. | |
| 2021/0363261 A1 | 11/2021 | Chang et al. | |
| 2022/0025037 A1 | 1/2022 | Baruah et al. | |
| 2022/0119534 A1 | 4/2022 | Baruah et al. | |
| 2022/0195065 A1 | 6/2022 | Chang et al. | |
| 2022/0380459 A1 | 12/2022 | Chang et al. | |

FOREIGN PATENT DOCUMENTS

| | | |
|---|---|---|
| CN | 105906722 A | 8/2016 |
| DE | 102013019352 A1 | 9/2015 |
| EP | 627940 A1 | 12/1994 |
| EP | 845998 A1 | 6/1998 |
| EP | 871673 A1 | 10/1998 |
| EP | 1124568 A1 | 8/2001 |
| EP | 1769000 B1 | 4/2007 |
| EP | 2185595 A1 | 5/2010 |
| EP | 2222706 B2 | 9/2010 |
| EP | 2927321 A1 | 10/2015 |
| EP | 2930188 A1 | 10/2015 |
| EP | 2942629 A1 | 11/2015 |
| EP | 2982380 A1 | 2/2016 |
| EP | 2990416 A1 | 3/2016 |
| RU | 2588668 C2 | 7/2016 |
| RU | 2593720 C2 | 8/2016 |
| WO | WO-1988008854 A1 | 11/1988 |
| WO | WO-1989006544 A1 | 7/1989 |
| WO | WO-1996/027011 A1 | 9/1996 |
| WO | WO-2001071005 A2 | 9/2001 |
| WO | WO-2004056873 A1 | 7/2004 |
| WO | WO-2006037960 A2 | 4/2006 |
| WO | WO-2007002905 A1 | 1/2007 |
| WO | WO-2007042573 A2 | 4/2007 |
| WO | WO-2007055926 A1 | 5/2007 |
| WO | WO-2007097812 A2 | 8/2007 |
| WO | WO-2009007124 A1 | 1/2009 |
| WO | WO-2009077483 A1 | 6/2009 |
| WO | WO-2009/089004 A1 | 7/2009 |
| WO | WO-2010017103 A2 | 2/2010 |
| WO | WO-2010080124 A2 | 7/2010 |
| WO | WO-2011014659 A2 | 2/2011 |
| WO | WO-2011075636 A2 | 6/2011 |
| WO | WO-2011109400 A2 | 9/2011 |
| WO | WO-2011/131746 A2 | 10/2011 |
| WO | WO-2011143545 A1 | 11/2011 |
| WO | WO-2012006490 A2 | 1/2012 |
| WO | WO-2012/025530 A1 | 3/2012 |
| WO | WO-2012/032080 A1 | 3/2012 |
| WO | WO-2012034039 A2 | 3/2012 |
| WO | WO-2012/045752 A1 | 4/2012 |
| WO | WO-2012058768 A1 | 5/2012 |
| WO | WO-2012125850 A1 | 9/2012 |
| WO | WO-2012158818 A2 | 11/2012 |
| WO | WO-2012162482 A1 | 11/2012 |
| WO | WO-2013013700 A1 | 1/2013 |
| WO | WO-2013036799 A2 | 3/2013 |
| WO | WO-2013092001 A1 | 6/2013 |
| WO | WO-2013192594 A2 | 12/2013 |
| WO | WO-2014001324 A1 | 1/2014 |
| WO | WO-2014012085 A2 | 1/2014 |
| WO | WO-2014079000 A1 | 5/2014 |
| WO | WO-2014/084607 A1 | 6/2014 |
| WO | WO-2014110601 A1 | 7/2014 |
| WO | WO-2014124326 A1 | 8/2014 |
| WO | WO-2014/145806 A2 | 9/2014 |
| WO | WO-2014131712 A1 | 9/2014 |
| WO | WO-2014144763 A2 | 9/2014 |
| WO | WO-2014/165818 A2 | 10/2014 |
| WO | WO-2014159940 A1 | 10/2014 |
| WO | WO-2014198748 A1 | 12/2014 |
| WO | WO-2015009856 A2 | 1/2015 |
| WO | WO-2015036582 A2 | 3/2015 |
| WO | WO-2015036606 A1 | 3/2015 |
| WO | WO-2015063187 A1 | 5/2015 |
| WO | WO-2015070061 A1 | 5/2015 |
| WO | WO-2015077891 A1 | 6/2015 |
| WO | WO-2015089344 A1 | 6/2015 |
| WO | WO-2015095412 A1 | 6/2015 |
| WO | WO-2015095539 A1 | 6/2015 |
| WO | WO-2015095972 A1 | 7/2015 |
| WO | WO-2015/150447 A1 | 10/2015 |
| WO | WO-2015153765 A1 | 10/2015 |
| WO | WO-2015153912 A1 | 10/2015 |
| WO | WO-2015158636 A1 | 10/2015 |
| WO | WO-2015169781 A1 | 11/2015 |
| WO | WO-2015181282 A1 | 12/2015 |
| WO | WO-2015184203 A1 | 12/2015 |
| WO | WO-2015184207 A1 | 12/2015 |
| WO | WO-2015197582 A1 | 12/2015 |
| WO | WO-2015197593 A1 | 12/2015 |
| WO | WO-2015197598 A1 | 12/2015 |
| WO | WO-2016001810 A1 | 1/2016 |
| WO | WO-2016011571 A1 | 1/2016 |
| WO | WO-2016023909 A1 | 2/2016 |
| WO | WO-2016025880 A1 | 2/2016 |
| WO | WO-2016028672 A1 | 2/2016 |
| WO | WO-2016032334 A1 | 3/2016 |
| WO | WO-2016070959 A1 | 5/2016 |
| WO | WO-2016090278 A2 | 6/2016 |
| WO | WO-2016097408 A1 | 6/2016 |
| WO | WO-2016100533 A2 | 6/2016 |
| WO | WO-2016109774 A1 | 7/2016 |
| WO | WO-2016115274 A1 | 7/2016 |
| WO | WO-2016122701 A1 | 8/2016 |
| WO | WO-2016134371 A2 | 8/2016 |
| WO | WO-2016135041 A1 | 9/2016 |
| WO | WO-2016135066 A1 | 9/2016 |
| WO | WO-2016142768 A1 | 9/2016 |

(56) References Cited

FOREIGN PATENT DOCUMENTS

| | | |
|---|---|---|
| WO | WO-2016146702 A1 | 9/2016 |
| WO | WO-2016161390 A1 | 10/2016 |
| WO | WO-2016164369 A2 | 10/2016 |
| WO | WO-2016164637 A1 | 10/2016 |
| WO | WO-2016166139 A1 | 10/2016 |
| WO | WO-2016184592 A1 | 11/2016 |
| WO | WO-2016187220 A2 | 11/2016 |
| WO | WO-2016191305 A1 | 12/2016 |
| WO | WO-2016196237 A1 | 12/2016 |
| WO | WO-2016201300 A1 | 12/2016 |
| WO | WO-2016201389 A2 | 12/2016 |
| WO | WO-2016207273 A2 | 12/2016 |
| WO | WO-2016207278 A1 | 12/2016 |
| WO | WO-2017005732 A1 | 1/2017 |
| WO | WO-2017008169 A1 | 1/2017 |
| WO | WO-2017011342 A1 | 1/2017 |
| WO | WO-2017021349 A1 | 2/2017 |
| WO | WO-2017048824 A1 | 3/2017 |
| WO | WO-2017075432 A2 | 5/2017 |
| WO | WO-2017079694 A2 | 5/2017 |
| WO | WO-2017081190 A1 | 5/2017 |
| WO | WO-2017083545 A1 | 5/2017 |
| WO | WO-2017114694 A1 | 7/2017 |
| WO | WO-2017124002 A1 | 7/2017 |
| WO | WO-2017125897 A1 | 7/2017 |
| WO | WO-2017143406 A1 | 8/2017 |
| WO | WO-2017165464 A1 | 9/2017 |
| WO | WO-2017165683 A1 | 9/2017 |
| WO | WO-2017177337 A1 | 10/2017 |
| WO | WO-2017180813 A1 | 10/2017 |
| WO | WO-2017211873 A1 | 12/2017 |
| WO | WO-2017218707 A2 | 12/2017 |
| WO | WO-2018045090 A1 | 3/2018 |
| WO | WO-2018098365 A2 | 5/2018 |
| WO | WO-2018119171 A1 | 6/2018 |
| WO | WO-2018148445 A1 | 8/2018 |
| WO | WO-2018148447 A1 | 8/2018 |
| WO | WO-2018148566 A1 | 8/2018 |
| WO | WO-2018148610 A1 | 8/2018 |
| WO | WO-2018152516 A1 | 8/2018 |
| WO | WO-2018152518 A1 | 8/2018 |
| WO | WO-2018152530 A1 | 8/2018 |
| WO | WO-2018152547 A1 | 8/2018 |
| WO | WO-2018157147 A1 | 8/2018 |
| WO | WO-2018201051 A1 | 11/2018 |
| WO | WO-2018217799 A1 | 11/2018 |
| WO | WO-2018217945 A1 | 11/2018 |
| WO | WO-2018217947 A1 | 11/2018 |
| WO | WO-2019035939 A1 | 2/2019 |
| WO | WO-2019040727 A1 | 2/2019 |
| WO | WO-2019051308 A1 | 3/2019 |
| WO | WO-2019055677 A1 | 3/2019 |
| WO | WO-2019/231920 A1 | 12/2019 |
| WO | WO-2020172189 A1 | 8/2020 |

OTHER PUBLICATIONS

Kluge et al. (2017) "EGFR/CD16A TandAbs are efficacious NK-cell engagers with favorable biological properties which potently kill EGFR(+) tumors with and without Ras mutation," Cancer Research 77(13 Suppl.):Abstract 3641.
McWilliams, et al. (2016) "Targeting the Tumor Evasion Interaction of NKG2A and Its Ligand HLA-E Increases Natural-Killer Cell Activity in Chronic Lymphocytic Leukemia," Blood 1289-1291.
Myers et al. (2021) "Exploring the NK cell platform for cancer immunotherapy," Nature Reviews Clinical Oncology 18(2):85-100.
Nie et al. (2020) "Biology drives the discovery of bispecific antibodies as innovative therapeutics," Antibody Therapeutics 3(1):18-62.
Notice of Opposition for Colombia Patent Application No. NC2020/0010345 dated Dec. 16, 2020.
Vyas et al. (2016) "Mono- and dual-targeting triplebodies activate natural killer cells and have anti-tumor activity in vitro and in vivo against chronic lymphocytic leukemia," Oncoimmunology 5(9):p. e1211220.
Ahmad et al. (2012) "scFv antibody: principles and clinical application," *Clinical and Developmental Immunology* 2012:1-16.
Averdam et al. (2009) "A Novel System of Polymorphic and Diverse NK Cell Receptors in Primates," *PLoS Genetics* 5(10):e1000688.
Busfield et al. (2014) "Targeting of acute myeloid leukemia in vitro and in vivo with an anti-CD123 mAb engineered for optimal ADCC," *Leukemia* 28(11): 2213-2221.
Cai et al. (2014) "Autonomous Stimulation of Cancer Cell Plasticity by the Human NKG2D Lymphocyte Receptor Coexpressed with Its Ligands on Cancer Cells," *PLOS ONE* 9(10):e108942.
Cho et al. (2010) "Delivery of NKG2D Ligand Using an Anti-HER2 Antibody-NKG2D Ligand Fusion Protein Results in an Enhanced Innate and Adaptive Antitumor Response," *Cancer Research* 70(24):10121-10130.
Chu, S. et al. (2014) "Immunotherapy with Long-Lived Anti-CD123 × Anti-CD3 Bispecific Antibodies Stimulates Potent T Cell-Mediated Killing of Human AML Cell Lines and of CD123+ Cells in Monkeys: A Potential Therapy for Acute Myelogenous Leukemia 11," *Blood* 124(21):2316.
Ding et al. (2018) "Fusion Proteins of NKG2D/NKG2DL in Cancer Immunotherapy," *International Journal of Molecular Sciences* 19(1):177.
Germain et al. (2005) "MHC Class I-Related Chain a Conjugated to Antitumor antibodies Can Sensitize Tumor Cells to Specific Lysis by Natural Killer Cell," *Clinical Cancer Research* US 11(20):7516-7522.
Glas et al. (1997) "Analysis of rearranged immunoglobulin heavy chain variable region genes obtained from a bone marrow transplant (BMT) recipient," *Clinical & Experimental Immunology* 107(2):372-380.
Gleason et al. (2012) "Bispecific and Trispecific Killer Cell Engagers Directly Activate Human NK Cells through CD16 Signaling and Induce Cytotoxicity and Cytokine Production," *Molecular Cancer Therapeutics* 11(12):2674-2684.
Gleason et al. (2014) "CD16×CD33 bispecific killer cell engager (BiKE) activates NK cells against primary MDS and MDSC CD33+ targets," *Blood* 123(19):3016-3026.
Hezareh et al. (2001) "Effector Function Activities of a Panel of Mutants of a Broadly Neutralizing Antibody against Human Immunodeficiency Virus Type 1," *Journal of Virology* 75(24):12161-12168.
Jachimowicz et al. (2011) "Induction of In Vitro and In Vivo NK Cell Cytotoxicity Using High-Avidity Immunoligands Targeting Prostate-Specific Membrane Antigen in Prostate Carcinoma," *Mol Cancer Thera*, 10(6):1036-1045.
Kellner et al. (2012) "Fusion proteins between ligands for NKG2D and CD20-directed single-chain variable fragments sensitize lymphoma cells for natural killer cell-mediated lysis and enhance antibody-dependent cellular cytotoxicity," *Leukemia* 26:830-834.
Kellner et al. (2013) "Promoting natural killer cell functions by recombinant immunoligands mimicking an induced self phenotype," *Oncoimmunology* 2(6):e24481.
Kellner et al. (2016) "Enhancing natural killer cell-mediated lysis of lymphoma cells by combining therapeutic antibodies with CD20-specific immunoligands engaging NKG2D or NKp30," *OncoImmunology* 5(1):e1058459-1-e1058459-12.
Kwong et al. (2008) "Generation, affinity maturation, and characterization of a human anti-human NKG2D monoclonal antibody with dual antagonistic and agonistic activity," *Journal of Molecular Biology* 384(5):1143-1156.
Lin et al. (2013) "CD4+ NKG2D+ T cells induce NKG2D down-regulation in natural killer cells in CD86-RAE-1 E transgenic mice," *Immunology* 141(3):401-415.
Liu et al. (2017) "Fc engineering for Developing Therapeutic Bispecific Antibodies and Novel Scaffolds," *Frontiers in Immunology* 8(38):1-15.
Madlener et al. (2010) "A Bispecific Protein Targeting the NKG2D Receptor on Natural Killer Cells: In Vitro and In Vivo activity of ULBP2-CEA," *Blood* 116(21):2095.

(56) References Cited

OTHER PUBLICATIONS

Morvan et al. (2016)."NK cells and cancer: you can teach innate cells new tricks" Nat Rev Cancer 16(1):7-19.
Nagasaki et al. (2014) "Interleukin-6 released by colon cancer-associated fibroblasts is critical for tumour angiogenesis: anti-interleukin-6 receptor antibody suppressed angiogenesis and inhibited tumour-stroma interaction," British Journal of Cancer 110(2):469-478.
Petricevic et al. (2013) "Trastuzumab mediates antibody-dependent cell-mediated cytotoxicity and phagocytosis to the same extent in both adjuvant and metastatic HER2/neu breast cancer patients," Journal of Translational Medicine 11(307).
Raab et al. (2014) "Fc-Optimized NKG2D-Fc Constructs Induce NK Cell Antibody-Dependent Cellular Cytotoxicity Against Breast Cancer Cells Independently of HER2/neu Expession Status," Journal of Immunology 193(8):4261-72.
Romee et al. (2013) "NK cell CD16 surface expression and function is regulated by a disintegrin and metalloprotease-17 (ADAM17)," Blood 121(18):3599-608.
Rothe et al. (2013) "The Bispecific Immunoligand ULBP2-aCEA Redirects Natural Killer Cells to Tumor Cells and Reveals Potent Anti-Tumor Activity Against Colon Carcinoma," Int. J. Cancer 134(12):2829-2840.
Schuster et al. (2015) "Immunotherapy with the trifunctional anti-CD20 × anti-CD3 antibody FBTA05 (Lymphomun) in paediatric high-risk patients with recurrent CD20-positive B cell malignancies," British Journal of Haematology 169(1):90-102.
Smits et al. (2016) "Designing multivalent proteins based on natural killer cell receptors and their ligands as immunotherapy for cancer," Expert Opinion on Biological Therapy 16(9):1105-1112.
Spear et al. (2013) "NKG2D ligands as therapeutic targets," Cancer Immunology 13:8.
Steigerwald et al. (2009) "Human IgG1 antibodies antagonizing activating receptor NKG2D on natural killer cells," mAbs 1(2):115-127.
Steinbacher et al. (2015) "An Fc-optimized NKG2D-immunoglobulin G fusion protein for induction of natural killer cell reactivity against leukemia," International Journal of Cancer 136(5):1073-1084.
Strong (2002) "Asymmetric ligand recognition by the activating natural killer cell receptor NKG2D, a symmetric homodimer," Molecular Immunology 38(14):1029-1037.
Tay et al. (2016) "TriKEs and BiKEs join CARs on the cancer immunotherapy highway." Human Vaccines & Immunotherapeutics 12(11):2790-2796.
Vaks et al. (2018) "Design Principles for Bispecific IgGs, Opportunities and Pitfalls of Artificial Disulfide Bonds," Antibodies 7(27):1-28.
Von Strandmann et al. (2006) "A novel bispecific protein (ULBP2-BB4) targeting the NKG2D receptor on natural killer (NK) cells and CD138 activates NK cells and has potent antitumor activity against human multiple myeloma in vitro and in vivo," Blood 107(5):1955-1962.
Wang et al. (2016) "A bispecific protein rG7S-MICA recruits natural killer cells and enhances NKG2D-mediated immunosurveillance against hepatocellular carcinoma," Cancer Letters 372(2):166-178.
Weiss-Steider et al. (2011) "Expression of MICA, MICB and NKG2D in human leukemic myelomonocytic and cervical cancer cells," Journal of Experimental & Clinical Cancer Research 30(1):37.
Written Opinion for International Application No. PCT/US2019/017330 dated Jun. 11, 2019.
Xu et al. (2019) "A VEGFR2-MICA bispecific antibody activates tumor-infiltrating lymphocytes and exhibits potent anti-tumor efficacy in mice," Cancer Immunology Immunotherapy 68(9):1429-1441.
Yeap et al. (2016) "CD16 is indispensable for antibody dependent cellular cytotoxicity by human monocytes," Scientific Reports 6:34310.
Young et al. (1995) "Thermal stabilization of a single-chain Fv antibody fragment by introduction of a disulphide bond," FEBS Letters 377(2):135-139.
Affimed, Affimed Enters Into Collaboration With Merck to Evaluate AFM13 in Combination With . . . Retrieved < U RL:https ://www. affimed.com/affi med-enters-into-collaboration-with-merck-to-evaluate-afm 13-i n-combination-with-keytruda-pembrolizumab-for-patients-with-hodgkin-lymphoma/>[retrieved on Feb. 1, 2023] Jan. 25, 2016.
Akbar et al. (2021) "A compact vocabulary of paratope-epitope interactions enables predictability of antibody-antigen binding," Cell Reports 34:108856 21 pages.
Altshuler et al. (2010) "Generation of Recombinant Antibodies and Means for Increasing Their Affinity," Biochemistry (Moscow) 75(13):1584-1605.
Atwell et al. (1989) "Stable Heterodimers from Remodeling the Domain Interface of a Homodimer using a Phage Display Library," J Mol Biol 270:26-35.
Baek et al. (2014) "Construction of a Large Synthetic Human Fab Antibody Library on Yeast Cell Surface by Optimized Yeast Mating," J Microbial Biotechnol 24(3):408-420.
Bendayan et al. (1995) "Possibilities of False Immunocytochemical Results Generated by the Use of Monoclonal Antibodies: The Example of the Anti-proinsulin Antibody," J. Histochem. Cytochem. 43:881-886.
Berenbaum (1977) "Synergy, additivism and antagonism in immunosuppression," Clin. Exp. Immunol. 28:1-18.
Berenbaum (1989) "What is Synergy?" Pharmacological Reviews 41:93-141.
Boltz (2011) "Bi-specific Aptamers mediating Tumour Cell Lysis," Dissertation, M.Sc. Molekulare Biotechnologie, Technische Universität Darmstadt, pp. 1-133.
Bost et al. (1988) "Antibodies Against a Peptide Sequence Within the HIV Envelope Protein Crossreacts with Human Interleukin-2," Immunological Investigations 17(6&7):577-586.
Bostrom, et al. (2009) "Improving Antibody Binding Affinity and Specificity for Therapeutic Development," Methods and Protocols 525:353-376.
Bowen et al. (2016) "Revisiting the Immunoglobulin Intramolecular Signaling Hypothesis," Trends Immunol. 37(11):721-723.
Branca et al. (2018) "Nature Biotechnology's academic spinouts of 2017," Nature Biotechnology 36(4):297-306.
Brinkmann et al. (2017) "The making of bispecific antibodies," MABS 9(2):182-212.
Brown et al. (1996) "Tolerance of single, but not multiple, amino acid replacements in antibody VH CDR 2: a means of minimizing B cell wastage from somatic hypermutation?," Journal of Immunology, 156: 3285-3291.
Bruhns et al. (2009) "Specificity and affinity of human FCγ receptors and their polymorphic variants for human IgG subclasses," Blood 113(16):3716-3724.
Bryceson et al. (2006) "Synergy among receptors on resting NK cells for the activation of natural cytotoxicity and cytokine secretion," Blood 107(1):159-166.
Casset et al. (2003) "A peptide mimetic of an anti-CD4 monoclonal antibody by rational design," Biochemical and Biophysical Research Communications 307:198-205.
Chan et al. (2010) "Therapeutic antibodies for autoimmunity and inflammation," Nature Reviews 10:301-316.
Chen et al. (1995) "Enhancement and destruction of antibody function by somatic mutation: unequal occurrence is controlled by V gene combinatorial associations," The EMBO Journal 14(12):2784-2794.
Chen et al. (1999) "Selection and Analysis of an Optimized Anti-VEGF Antibody: Crystal Structure of an Affinity-matured Fab in Complex with Antigen," J. Mol. Biol. 293:865-881.
Chen X. et al. (2013) "Fusion protein linkers: property, design and functionality" Advanced drug delivery reviews, 65(10):1357-1369.
Choi et al. (2013) "A Heterodimeric Fc-Based Bispecific Antibody Simultaneously Targeting VEGFR-2 and Met Exhibits Potent Anti-tumor Activity," Mol Cancer Ther. 12(12):2748-2759.

(56) References Cited

OTHER PUBLICATIONS

Choi et al. (2015) "Crystal structures of immunoglobulin Fc heterodimers reveal the molecular basis for heterodimer formation," Molecular Immunology 65(2):377-83.
Choi et al. (2015) "Engineering of Immunoglobulin Fc Heterodimers Using Yeast Surface-Displayed Combinatorial Fc Library Screening," PloS One. Dec. 16, 2015; 10(12);e0145349; pp. 1-20.
Colman P. M. (1994) "Effects of amino acid sequence changes on antibody-antigen interactions" Research in Immunology 145(1):33-36.
Cunningham et al. (1969) "Subgroups of Amino Acid Sequences in the Variable Regions of Immunoglobulin Heavy Chains," Proc Natl Acad Sci USA 64(3):997-1003.
Dahlberg et al. (2015) "Natural Killer Cell-Based Therapies Targeting Cancer: Possible Strategies to Gain and sustain Anti-Tumor Activity" Frontiers in Immunology 6(Article 605):19 pages.
Davis et al. (2010) "SEEDbodies: Fusion Proteins Based on Strand-Exchange Engineered Domain (SEED) CH3 Heterodimers in an Fc Analogue Platform for Asymmetric Binders or Immunofusions and Bispecific Antibodies," Protein Eng Des Sel 23(4):195-202.
De Pascalis et al. (2002) "Grafting of "Abbreviated" Complementarity-Determining Regions Containing Specificity-Determining Residues Essential for Ligand Contact to Engineer a Less Immunogenic Humanized Monoclonal Antibody," *The Journal of Immunology* 169:3076-3084.
Dickopf et al. (2020) "Format and geometries matter: Structure-based design defines the functionality of bispecific antibodies," *Computational and Structural Biotechnology Journal* 18:1221-1227.
Edwards et al. (2003) "The Remarkable Flexibility of the Human Antibody Repertoire; Isolation of Over One Thousand Different Antibodies to a Single Protein, BLyS," *J. Mol. Biol.* 334:103-118.
El-Amine et al. (2002) "In vivo induction of tolerance by an Ig peptide is not affected by the deletion of FcR or a mutated IgG Fc fragment," *International Immunology* 14(7):761-766.
Elliott et al. (2014) "Antiparallel conformation of knob and hole aglycosylated half-antibody homodimers is mediated by a CH2-CH3 hydrophobic interaction", J. Mol. Biol., 426(9):1947-57.
Feng et al. (2011) "Design, Expression and Characterization of a Soluble Single-Chain Functional Human Neonatal Fc Receptor," Protein Expr Purif 79(1):66-71.
Feng et al., (2020) "NKG2D-Fc fusion protein promotes antitumor immunity through the depletion of immunosuppressive cells," Cancer Immunol. Immunother. 69(10):2147-2155.
Germain et al. (2008) "Redirecting NK cells mediated tumor cell lysis by a new recombinant bifunctional protein," *Protein Engineering, Design & Selection* 21(11):665-672.
Goel et al. (2004) "Plasticity within the Antigen-Combining Site May Manifest as Molecular Mimicry in the Humoral Immune Response," *The Journal of Immunology* 173(12):7358-7367.
Gonzales, et al. (2005) "Minimizing the Immunogenicity of Antibodies for Clinical Application," *Tumor Biol.* 26(1):31-43.
Gunasekaran et al. (2010) "Enhancing Antibody Fc Heterodimer Formation through Electrostatic Steering Effects: Applications to Bispecific Molecules and Monovalent IgG," J Biol Chem 285(25):19637-46.
Ha et al. (2016) "Immunoglobulin Fc Heterodimer Platform Technology: From Design to Applications in Therapeutic Antibodies and Proteins," Front Immunol. 7:394, 16 pages.
Han et al. (2018) "Control of triple-negative breast cancer using ex vivo self-enriched, constimulated NKG2D CAR T cells," 11:92 13 pages.
Hasegawa et al. (2017) "Single amino acid substitution in LC-CDR1 induces Russell body phenotype that attenuates cellular protein synthesis through eIF2α phosphorylation and thereby downregulates IgG secretion despite operational secretory pathway traffic," *MABS* 9(5):854-873.

Henry et al. (2017) "Stability-Diversity Tradeoffs Impose Fundamental Constraints on Selection of Synthetic Human $V_H/V_L$ Single-Domain Antibodies from In Vitro Display Libraries," *Frontiers in Immunology*, 8:1-15.
Herold et al. (2017) "Determinants of the assembly and function of antibody variable domains," Scientific Reports, 7:12276.
Hlavacek et al. 1999 "Steric Effects on Multivalent Ligand-Receptor Binding: Exclusion of Ligand Sites by Bound Cell Surface Receptors," *Biophysical Journal* 76:3031-3043.
Holliger et al. (2005) "Engineered antibody fragments and the rise of single domains," Nat Biotechnol 23(9): 1126-36.
Hoseini et al. (2017) "Acute myeloid leukemia targets for bispecific antibodies," *Blood Cancer Journal* 7(2):e522 (12 pages).
Janeway et al. (1997) Chapter 3, Structure of the Antibody Molecule and Immunoglobulin Genes, *Immunology Third Edition, Garland Publishing Inc.*, 3:1-3:11.
Jonnalagadda et al. (2015) "Chimeric Antigen Receptors With Mutated IgG4 Fc Spacer Avoid Fc Receptor Binding and Improve T Cell Persistence and Antitumor Efficacy," *Molecular Therapy* 23(4):757-768.
Junttila et al. (2014) "Antitumor Efficacy of a Bispecific Antibody That Targets HER2 and Activates T Cells," *Cancer Research* 74(19):5561-5571.
Kanyavuz et al. (2019) "Breaking the law: unconventional strategies for antibody diversification," *Nature Reviews Immunology* 19(6):355-368.
Kaur et al. (2015) "Applications of In Vitro—In Vivo Correlations in Generic Drug Development: Case Studies," *The AAPS Journal* 17(4):1035-1039; doi: 10.1208/s12248-015-9765-1.
Kijanka et al. (2013) "Rapid optical imaging of human breast tumour xenografts using anti-HER2 VHHs site-directly conjugated to IRDye 800CW for image-guided surgery," Eur J Nucl Med Mol Imaging 40:1718-1729.
Kim et al. (2014) "Mutational approaches to improve the biophysical properties of human single-domain antibodies," *Biochimica et Biophysica Acta*, 1844:1983-2001.
Kjellev et al. (2007) "Inhibition of NKG2D receptor function by antibody therapy attenuates transfer-induced colitis in SCID mice," *Eur. J. Immunol.* 37:1397-1406.
Klein et al. (2012) "Progress in overcoming the chain association issue in bispecific; heterodimeric IgG antibodies," mAbs 4(6):653-663.
Koerner et al. (2015) "Induction of NK and T Cell Immune Responses Against Leukemia Cells by Bispecific NKG2D-CD16 and -CD3 Fusion Proteins," Blood 126(23):2558, Abstract 606 (2 pages).
Kranz et al. (1981) "Restricted reassociation of heavy and light chains from hapten-specific monoclonal antibodies," *Pro. Natl. Acad. Sci. USA* 78(9):5807-5811.
Krieg et al. (2005) "Functional Analysis of B and T Lymphocyte Attenuator Engagement on CD4+ and CD8+ T Cells," *The Journal of Immunology* 175(10):6420-6427.
Kunik, et al. (2012) "Structural consensus among antibodies defines the antigen binding site," *PLoS Comput Biol.* 8(2):e1002388.
Lamminmäki et al. (2001) "Crystal Structure of a Recombinant Anti-estradiol Fab Fragment in Complex with 17ß-Estradiol," *The Journal of Biological Chemistry* 276(39):36687-36694.
Lewis et al. (2014) "Generation of bispecific IgG antibodies by structure-based design of an orthogonal Fab interface," Nat Biotechnol 32(2):191-98.
Lin et al. (2011) "Improved affinity of a chicken single-chain antibody to avian infectious bronchitis virus by site-directed mutagenesis of complementarity-determining region H3," *African Journal of Biotechnology* 10(79):18294-18303.
Lippow et al. (2007) "Computational design of antibody-affinity improvement beyond in vivo maturation," *Nature Biotechnology* 25(10):1171-1176.
Lloyd et al. (2009) "Modelling the human immune response: performance of a 1011 human antibody repertoire against a broad panel of therapeutically relevant antigens," *Protein Engineering, Design and Selection* 22(3):159-168.

(56) References Cited

OTHER PUBLICATIONS

Lo et al. (2021) "Conformational epitope matching and prediction based on protein surface spiral features," *BMC Genomics* 22(Suppl 2):116 16 pages.
Long et al. (2013) "Controlling NK Cell Responses: Integration of Signals for Activation and Inhibition," Annu Rev Immunol. 2013 ; 31: 10.1146/annurev-immunol-020711-075005.
Lund et al. (1996) "Multiple interactions of IgG with its core oligosaccharide can modulate recognition by complement and human Fc gamma receptor I and influence the synthesis of its oligosaccharide chains," *J. Immunol* 157:4963-4969.
MacCallum et al. (1996) "Antibody-antigen Interactions: Contact Analysis and Binding Site Topography," *J. Mol. Biol.* 262:732-745.
Maeda et al. (2015) "New antibody modification technology and its application to antibody drugs," Farumashia 51(5):424-428.
Maeda Y. et al. (1997) "Engineering of Functional Chimeric Protein G-Vargula Luciferase" Analytical biochemistry, 249(2):147-152.
Maelig et al. (2016) "NK cells and cancer: you can teach innate cells new tricks", Nature Reviews Cancer, 16(1):7-19.
Mandelboim et al. (1999) "Human CD16 as a lysis receptor mediating direct natural killer cell cytotoxicity," *PNAS USA* 96(10):5640-5644; doi: 10.1073/pnas.96.10.5640.
Mariuzza et al. (1987) "The Structural Basis of Antigen-Antibody Recognition," *Ann. Rev. Biophys. Chem.* 16:139:59.
Marks et al. (2020) "How repertoire data are changing antibody science," *J. Biol. Chem.* 295(29):9823-9837.
McCarthy et al. (2001) "Altering the fine specificity of an anti-Legionella single chain antibody by a single amino acid insertion," *Journal of Immunological Methods* 251:137-149.
Merchant et al. (1998), "An efficient route to human bispecific IgG," Nature Biotechnology 16, 677-681 doi : 10.1038/nbt0798-677.
Miller et al. (2003) "Design, Construction, and in Vitro Analyses of Multivalent Antibodies," J Immunol 170(9):4854-61.
Mimoto et al. (2014) "Crystal structure of a novel asymmetrically engineered Fe variant with improved affinity for FcγRs," Mo/ Immunol 58(1):132-38.
Moore et al. (2011) "A novel bispecific antibody format enables simultaneous bivalent and monovalent co-engagement of distinct target antigens," mAbs 3:6, 546-557; Nov./Dec. 2011, Landes Bioscience, DOI: 10.4161/mabs.3.6.18123.
Morris "Epitope Mapping of Protein Antigens by Competition ELISA," The Protein Protocols Handbook, Totowa, NJ, Humana Press, (Jan. 1, 1996):595-600.
Muda et al. (2011) "Therapeutic assessment of SEED: a new engineered antibody platform designed to generate mono- and bispecific antibodies," Protein Eng Des Se/ 24(5):447-54.
Muller et al. (2015) "Trastuzumab emtansine (T-DM1) renders HER2+ breast cancer highly susceptible to CTLA-4/PD-1 blockade," Sci. Transl. Med. 7(315):1-14.
Muntasell et al. (2017) "Interplay between Natural Killer Cells and Anti-HER2 Antibodies:Perspectives for Breast Cancer Immunotherapy," *Front. Immunol.* 8:1544, doi: 10.3389/fimmu.2017.01544, 15 pages.
Muntasell et al. (2017) "Targeting NK-cell checkpoints for cancer immunotherapy," Current Opinion in Immunology 45:73-81.
Padlan et al. (1989) "Structure of an antibody-antigen complex: Crystal structure of the HyHEL-10 Fab-lysozyme complex," *Pro. Natl. Acad. Sci. USA* 86:5938-5942.
Pakula et al. (1989) "Genetic Analysis of Protein Stability and Function," *Annu. Rev. Genet.* 23:289-310.
Parsons et al. (2016) "NKG2D Acts as a Co-Receptor for Natural Killer Cell-Mediated Anti-HIV-1 Antibody-Dependent Cellular Cytotoxicity," AIDS Research and Human Retroviruses 32(10-11) 1089-1096.
Paul et al. (1993) "Fundamental Immunology," (textbook) 292-295.
Piche-Nicholas et al. (2018) "Changes in complementarity-determining regions significantly alter IgG binding to the neonatal Fc receptor (FcRn) and pharmacokinetics," *MABS* 10(1)81-94.
Portolano et al. (1993) "Lack of promiscuity in autoantigen-specific H and L chain combinations as revealed by human H and L chain roulette," *J. Immunol.* 15(30):880-887.

Powers et al. (2016) "Abstract 1407: FPA 144, a therapeutic monoclonal antibody targeting the FGFR2b receptor, promotes antibody dependent cell-mediated cytotoxicity and stimulates sensitivity to PD-1 in the 4T1 syngeneic tumor model," *Cancer Research* (4 pages).
Rabia et al. (2018) "Understanding and overcoming trade-offs between antibody affinity, specificity, stability and solubility" Biochem Eng J. 137:365-374.
Raulet (2003) "Roles of the NKG2D immunoreceptor and its ligands," *Nature: Reviews Immunology* 3:781-790; doi: 10.1038/nri1199.
Ridgway et al. (1996) "'Knobs-into-Holes' engineering of antibody Ch3 domains for heavy chain heterodimerization," Protein Engineering 9(7):617-21.
Roda-Navarro et al. (2020) "Understanding the Spatial Topology of Artificial Immunological Synapses Assembled in T Cell-Redirecting Strategies: A Major Issue in Cancer Immunotherapy," *Frontiers in Cell and Developmental Biology* 7:1-5.
Roell et al. (2017) "An Introduction to Terminology and Methoodology of Chemical Synergy—Perspectives from Across Disciplines," *Frontiers in Pharmacology: Cancer Molecular Targets and Therapeutics* 8:1-11.
Rosano et al. (2014) "Recombinant protein expression in *Escherichia coli*: advances and challenges" Frontiers in Microbiology 5(172):17 pages.
Rudikoff et al. (1982) "Single amino acid substitution altering antigen-binding specificity," *Pro. Natl. Acad. Sci USA* 79:1979-1983.
Safdari Y. et al. (2013) "Antibody humanization methods-a review and update" Biotechnology and Genetic Engineering Reviews, 29(2):175-186.
Sazinsky et al. (2008) "Aglycosylated immunoglobulin $G_1$ variants productively engage activating Fc receptors," *Proceedings of the National Academy of Sciences* 105(51)20167-20172.
Schroeder et al. (2010) "Structure and Function of Immunoglobulins," *J Allergy Clin Immunol* 125:S41-S52 (24 pages).
Shen J. et al. (2006) "Single variable domain-IgG fusion: a novel recombinant approach to Fc domain-containing bispecific antibodies" Journal of Biological Chemistry, 281(16):10706-10714.
Shum et al. (2002) "Conservation and Variation in Human and Common Chimpanzee CD94 and NKG2 Genes," *The Journal of Immunology* 168:240-252.
Siena et al. (2010) "Reduced Incidence of Infusion-Related Reactions in Metastatic Colorectal Cancer During Treatment With Cetuximab Plus Irinotecan With Combined Corticosteroid and Antihistamine Premedication," *Cancer* 116(7):1827-1837.
Singer et al. (1998) "Genes and Genomes," Moscow, "Mir" 1:63-64.
Sondermann et al. (2000) "The 3.2-Å crystal structure of the human IgG1 Fc fragment—Fc[gamma]RIII complex," Nature 406(6793):267-273.
Stamova et al. (2011) "Simultaneous engagement of the activatory receptors NKG2D and CD3 for retargeting of effector cells to CD33-positive malignant cells," *Leukemia* 25:1053-1056.
Stein et al. (2012) "Natural Killer (NK)- and T-Cell Engaging Antibody-Derived Therapeutics," *Antibodies* 1:88-123.
Strop et al. (2012) "Generating Bispecific Human IgG1 and IgG2 Antibodies from Any Antibody Pair," J Mol Biol 420:204-19.
Sulea et al. (2018) "Application of Assisted Design of Antibody and Protein Therapeutics (ADAPT) improves efficacy of a *Clostridium difficile* toxin A single-domain antibody," 8:2260 11 pages.
Tallarida (2000) "Drug Synergism and Dose Effect Analysis," Ed. Chapman & Hall pp. 1-71.
Teplyakov A. et al. (2014) "Antibody modeling assessment II. Structures and models" Proteins: Structure, Function, and Bioinformatics, 82(8):1563-1582.
Thakur et al. (2018) "Bispecific antibody based therapeutics: Strengths and challenges," Blood Review 32:339-347.
Torres M. et al. (2008) "The immunoglobulin constant region contributes to affinity and specificity" Trends in immunology, 29(2):91-97.
Trivedi et al. (2017) "Clinical pharmacology and translational aspects of bispecific antibodies," Clin. Transl. Sci., 10:147-162.

(56) References Cited

OTHER PUBLICATIONS

Vajda et al. (2021) "Progress toward improved understanding of antibody maturation," *Current Opinion in Structural Biology* 67:226-231.

Vajdos et al. (2002) "Comprehensive Functional Maps of the Antigen-binding Site of an Anti-ErbB2 Antibody Obtained with Shotgun Scanning Mutagenesis," *J. Mol. Biol.* 320:415-428.

Vallera et al. (2016) "IL 15 Trispecific Killer Engagers (TriKE) Make Natural Killer Cells Specific to CD33+ Targets While Also Inducing Persistence, In Vivo Expansion, and Enhanced Function," *Clin Cancer Res*, 22(14):3440-50.

Van de Winkel et al. (1993) "Human IgG Fc receptor heterogeneity: molecular aspects and clinical implications," Immunology Today 14(5):215-221.

Vidarsson et al. (2014) "IgG subclasses and allotypes: from structure to effector functions," Front. Immunol. 5:520, 17 pages.

Von Kreudenstein et al. (2013) "Improving Biophysical Properties of a Bispecific Antibody Scaffold to Aid Developability: Quality by Molecular Design," mAbs 5(5):646-54.

Von Kreudenstein et al. (2014), "Protein Engineering and the Use of Molecular Modeling and Simulation: The Case of Heterodimeric Fc Engineering," Methods 65(1):77-94.

Wang et al. (2018) "IgG Fc engineering to modulate antibody effector functions," Protein Cell 9(1):63-73.

Ward et al. (1989) "Binding activities of a epertoire of single immunoglobulin variable domains secreted from *Escherichia coli*," Nature 341:544-546.

Wark et al. (2006) "Latest technologies for the enhancement of antibody affinity", *Advanced Drug Delivery Reviews* 58(5-6):657-670.

Wensveen et al. (2018) "NKG2D: A Master Regulator of Immune Cell Responsiveness," *Frontiers in Immunology* 9(Article 411):8 pages.

Wikipedia: "Trifunctional antibody Feb. 1, 2018",, Jan. 2, 2018 (Jan. 2, 2018), pp. 1-4, XP093016568, Retrieved from the Internet: URL:https://en.wikipedia.org/w/index.php?title=Trifunctional antibody8 oldid=818265015.

Wranik et al. (2012) "LUZ-Y, a novel platform for the mammalian cell production of full-length IgG-bispecific antibodies," J Biol Chem 287(52):43331-9.

Wu et al. (1999) "Humanization of a Murine Monoclonal Antibody by Simultaneous Optimization of Framework and CDR Residues," *J. Mol. Biol.* 294:151-162.

Xie et al. (2005) "A new format of bispecific antibody: highly efficient heterodimerization, expression and tumor cell lysis," J Immunol Methods 296(1):95-101.

Xu et al. (2014) "Production of bispecific antibodies in "knobs-into-holes" using a cell-free expression system," mAbs 7(1)231-242.

Yan et al. (2014) "Construction of a synthetic phage-displayed Nanobody library with CDR3 regions randomized by trinucleotide cassettes for diagnostic applications," *Journal of Translational Medicine* 12:343 (12 pages).

Zhang et al. (2021) "Bispecific antibody-mediated redirection of NKG2D-CAR natural killer cells facilitates dual targeting and enhances antitumor activity," *Journal for ImmunoTherapy of Cancer*; 9:e002980 (24 pages). doi:10.1136/jitc-2021-002980.

Zhou et al. (1995) "Characterization of human homologue of 4-1BB and its ligand," Immunology Letters 45:67-73.

* cited by examiner

ANTIBODY VARIABLE DOMAINS TARGETING THE NKG2D RECEPTOR

CROSS-REFERENCE TO RELATED APPLICATIONS

This application is a U.S. national stage application, filed under 35 U.S.C. § 371, of International Application No. PCT/US2019/017330, filed on Feb. 8, 2019, which claims the benefit of and priority to U.S. Provisional Patent Application No. 62/628,161, filed on Feb. 8, 2018, the disclosure of which is incorporated by reference herein in its entirety for all purposes; and U.S. Provisional Patent Application 62/716,259, filed on Aug. 8, 2018.

FIELD OF THE INVENTION

The invention provides proteins with antibody heavy chain and light chain variable domains that can be paired to form an antigen-binding site targeting the Natural Killer group 2D (NKG2D) receptor on natural killer cells, pharmaceutical compositions comprising such proteins, and therapeutic methods using such proteins and pharmaceutical compositions, including for the treatment of cancer.

BACKGROUND

Cancer continues to be a significant health problem despite the substantial research efforts and scientific advances reported in the literature for treating this disease. Some of the most frequently diagnosed cancers include prostate cancer, breast cancer, and lung cancer. Prostate cancer is the most common form of cancer in men. Breast cancer remains a leading cause of death in women. Current treatment options for these cancers are not effective for all patients and/or can have substantial adverse side effects. Other types of cancer also remain challenging to treat using existing therapeutic options.

Cancer immunotherapies are desirable because they are highly specific and can facilitate destruction of cancer cells using the patient's own immune system. Fusion proteins such as bi-specific T-cell engagers are cancer immunotherapies described in the literature that bind to tumor cells and T-cells to facilitate destruction of tumor cells. Antibodies that bind to certain tumor-associated antigens and to certain immune cells have been described in the literature. See, for example WO 2016/134371 and WO 2015/095412.

Natural killer (NK) cells are a component of the innate immune system and make up approximately 15% of circulating lymphocytes. NK cells infiltrate virtually all tissues and were originally characterized by their ability to kill tumor cells effectively without the need for priming, which distinguishes them from T cells. Activated NK cells kill target cells by means similar to cytotoxic T cells—i.e., via cytolytic granules that contain perforin and granzymes as well as via death receptor pathways. Activated NK cells also secrete inflammatory cytokines such as IFN-gamma and chemokines that promote the recruitment of other leukocytes to the target tissue.

NK cells respond to signals through a variety of activating and inhibitory receptors on their surface. For example, when NK cells encounter healthy self-cells, their activity is inhibited through activation of the killer-cell immunoglobulin-like receptors (KIRs). Alternatively, when NK cells encounter cancer cells, they are activated via their activating receptors (e.g., NKG2D, NCRs, DNAM1). NK cells are also activated by the constant region of some immunoglobulins through CD16 receptors on their surface. The overall sensitivity of NK cells to activation depends on the sum of stimulatory and inhibitory signals. NKG2D is a type-II transmembrane protein that is expressed by essentially all natural killer cells where NKG2D serves as an activating receptor. The ability to modulate NK cell function via NKG2D is useful in various therapeutic contexts including malignancy.

SUMMARY

Antibodies to NKG2D have been identified that provide important advantages in the design of therapeutic agents. For example, some of these antibodies do not merely bind human NKG2D receptor, but have one or more further advantages such as the ability to agonize the receptor; the ability to compete with a natural ligand for binding to the receptor; and/or the ability to cross-react with NKG2D from other species such as cynomolgus monkey. These advantages can be achieved across a range of affinities for NKG2D.

Accordingly, one aspect of the invention relates to an antibody heavy chain variable domain at least 90% identical to the amino acid sequence QVQLVQSGAEVKKPGASVKVSCKASGYTFTSYYMHWVRQAPGQGLEWMGIINPSG GSTSYAQKFQGRVTMTRDTSTSTVYMELSSLRSEDTAVYYCARGAPNYGDTTHDYYYMDVWGKGTTVTVSS (SEQ ID NO:1, ADI-29379). In some embodiments, the antibody heavy chain variable domain is at least 95% identical to SEQ ID NO:1. In some embodiments, the heavy chain variable domain includes amino acid sequences YTFTSYYMH (SEQ ID NO:11) as the first complementarity-determining region 1 ("CDR1"), IINPSGGSTSYAQKFQG (SEQ ID NO:12) as the second CDR ("CDR2"), and ARGAPNYGDTTHDYYYMDV (SEQ ID NO:13) as the third CDR ("CDR3") of SEQ ID NO:1. In some embodiments, the heavy chain variable domain includes amino acid sequences SYYMH (SEQ ID NO:45) as CDR1, IINPSGGSTSYAQKFQG (SEQ ID NO:12) as CDR2, and GAPNYGDTTHDYYYMDV (SEQ ID NO:68) as CDR3 of SEQ ID NO:1.

Another aspect of the invention relates to an antibody heavy chain variable domain at least 90% identical to the amino acid sequence QVQLVQSGAEVKKPGASVKVSCKASGYTFTGYYMHWVRQAPGQGLEWMGWINPN SGGTNYAQKFQGRVTMTRDTSISTAYMELSRLRSDDTAVYYCARDTGEYYDTDDH GMDVWGQGTTVTVSS (SEQ ID NO: 3, ADI-29463). In some embodiments, the antibody heavy chain variable domain is at least 95% identical to SEQ ID NO:3. In some embodiments, the heavy chain variable domain includes amino acid sequences YTFTGYYMH (SEQ ID NO: 17) as the first complementarity-determining region ("CDR1"), WINPNSGGTNYAQKFQG (SEQ ID NO:18) as the second CDR ("CDR2"), and ARDTGEYYDTDDHGMDV (SEQ ID NO:19) as the third CDR ("CDR3") of SEQ ID NO:3. In some embodiments, the heavy chain variable domain includes amino acid sequences GYYMH (SEQ ID NO: 92) as CDR1, WINPNSGGTNYAQKFQG (SEQ ID NO:18) as CDR2, and DTGEYYDTDDHGMDV (SEQ ID NO:69) as CDR3 of SEQ ID NO:3.

Another aspect of the invention relates to an antibody heavy chain variable domain at least 90% identical to the amino acid sequence EVQLLESGGGLVQPGGSLRLSCAASGFTFSSYAMSWVRQAPGKGLEWVSAISGSGG STYYADSVKGRFTISRDNSKNTLYLQMNSLRAEDTAVYYCAKDGGYYDSGAGDYW GQGTLVTVSS (SEQ ID NO:5, ADI-27744). In some embodiments, the antibody heavy chain variable domain is at least 95% identical to SEQ ID NO:5. In some embodiments, the heavy chain variable domain includes amino acid sequences FTFSSYAMS (SEQ ID NO:23) as the first complementarity-determining region ("CDR1"), AISGSGGSTYYADSVKG (SEQ ID NO:24) as the second CDR ("CDR2"), and AKDGGYYDSGAGDY (SEQ ID NO:25) as the third CDR ("CDR3") of SEQ ID NO:5. In some embodiments, the heavy chain variable domain includes amino acid sequences SYAMS (SEQ ID NO:47) as CDR1, AISGSGGSTYYADSVKG (SEQ ID NO:24) as CDR2, and DGGYYDSGAGDY (SEQ ID NO:70) as CDR3 of SEQ ID NO:5.

Another aspect of the invention relates to an antibody heavy chain variable domain at least 90% identical to the amino acid sequence EVQLVESGGGLVKPGGSLRLS-CAASGFTFSSYSMNWVRQAPGKGLEWVSSISSSSSYI YYADSVKGRFTISRDNAKNSLYLQMNSLRAED-TAVYYCARGAPMGAAAGWFDPW GQGTLVTVSS (SEQ ID NO:7, ADI-27749). In some embodiments, the antibody heavy chain variable domain is at least 95% identical to SEQ ID NO:7. In some embodiments, the heavy chain variable domain includes amino acid sequences FTFS-SYSMN (SEQ ID NO:29) as the first complementarity-determining region ("CDR1"), SISSSSSYIYYADSVKG (SEQ ID NO: 30) as the second CDR ("CDR2"), and ARGAPMGAAAGWFDP (SEQ ID NO:31) as the third CDR ("CDR3") of SEQ ID NO:7. In some embodiments, the heavy chain variable domain includes amino acid sequences SYSMN (SEQ ID NO:48) as CDR1, SIS-SSSSYIYYADSVKG (SEQ ID NO: 30) as CDR2, and GAPMGAAAGWFDP (SEQ ID NO:71) as CDR3 of SEQ ID NO:7.

Another aspect of the invention relates to an antibody heavy chain variable domain at least 90% identical to the amino acid sequence EVQLVESGGGLVKPGGSLRLS-CAASGFTFSSYSMNWVRQAPGKGLEWVSSISSSSSYI YYADSVKGRFTISRDNAKNSLYLQMNSLRAED-TAVYYCARGAPIGAAAGWFDPWG QGTLVTVSS (SEQ ID NO:85, A49MI). In some embodiments, the antibody heavy chain variable domain is at least 95% identical to SEQ ID NO:85. In some embodiments, the heavy chain variable domain includes amino acid sequences FTFS-SYSMN (SEQ ID NO:29) as CDR1, SISSSSSYIYY-ADSVKG (SEQ ID NO: 30) as CDR2, and ARGAPI-GAAAGWFDP (SEQ ID NO:77) as CDR3 of SEQ ID NO:85. In some embodiments, the heavy chain variable domain includes amino acid sequences SYSMN (SEQ ID NO:48) as CDR1, SISSSSSYIYYADSVKG (SEQ ID NO: 30) as CDR2, and GAPIGAAAGWFDP (SEQ ID NO:78) as CDR3 of SEQ ID NO:85.

Another aspect of the invention relates to an antibody heavy chain variable domain at least 90% identical to the amino acid sequence QVQLVQSGAEVKKP-GASVKVSCKASGYTFTSYYMHWVRQAPGQ-GLEWMGIINPSG GSTSYAQKFQGRVTMTRDTST-STVYMELSSLRSEDTAVYYCAREGAGFAYGMDYY YMDVWGKGTTVTVSS (SEQ ID NO:9, ADI-29378). In some embodiments, the antibody heavy chain variable domain is at least 95% identical to SEQ ID NO:9. In some embodiments, the heavy chain variable domain includes amino acid sequences YTFTSYYMH (SEQ ID NO:35) as the first complementarity-determining region ("CDR1"), IINPSGGSTSYAQKFQG (SEQ ID NO: 36) as the second CDR ("CDR2"), and AREGAGFAYGMDYYYMDV (SEQ ID NO:37) as the third CDR ("CDR3") of SEQ ID NO:9. In some embodiments, the heavy chain variable domain includes amino acid sequences SYYMH (SEQ ID NO:45) as CDR1, IINPSGGSTSYAQKFQG (SEQ ID NO: 36) as CDR2, and EGAGFAYGMDYYYMDV (SEQ ID NO:72) as CDR3 of SEQ ID NO:9.

An antibody heavy chain variable domain of the invention can optionally be coupled to an amino acid sequence at least 90% identical to an antibody constant region, such as an IgG constant region including hinge, CH2 and CH3 domains with or without CH1 domain. In some embodiments, the amino acid sequence of the constant region is at least 90% identical to a human antibody constant region, such as an human IgG1 constant region, an IgG2 constant region, IgG3 constant region, or IgG4 constant region. In some other embodiments, the amino acid sequence of the constant region is at least 90% identical to an antibody constant region from another mammal, such as rabbit, dog, cat, mouse, or horse. One or more mutations can be included into the constant region as compared to human IgG1 constant region, for example at Q347, Y349, L351, S354, E356, E357, K360, Q362, S364, T366, L368, K370, N390, K392, T394, D399, S400, D401, F405, Y407, K409, T411 and/or K439. Exemplary substitutions include, for example, Q347E, Q347R, Y349S, Y349K, Y349T, Y349D, Y349E, Y349C, T350V, L351K, L351D, L351Y, S354C, E356K, E357Q, E357L, E357W, K360E, K360W, Q362E, S364K, S364E, S364H, S364D, T366V, T366I, T366L, T366M, T366K, T366W, T366S, L368E, L368A, L368D, K370S, N390D, N390E, K392L, K392M, K392V, K392F, K392D, K392E, T394F, T394W, D399R, D399K, D399V, S400K, S400R, D401K, F405A, F405T, Y407A, Y407I, Y407V, K409F, K409W, K409D, T411D, T411E, K439D, and K439E.

In certain embodiments, mutations that can be included into the CH1 of a human IgG1 constant region may be at amino acid V125, F126, P127, T135, T139, A140, F170, P171, and/or V173. In certain embodiments, mutations that can be included into the Cκ of a human IgG1 constant region may be at amino acid E123, F116, S176, V163, S174, and/or T164.

In some embodiments, one of the heavy chain variable domains described herein is combined with a light chain variable domain to form an antigen-binding site capable of binding NKG2D. For example, an antibody heavy chain variable domain at least 90% identical to the amino acid sequence of SEQ ID NO:1 can be paired with an antibody light chain variable domain at least 90% identical to the amino acid sequence EIVMTQSPATLSVSPGER-ATLSCRASQSVSSNLAWYQQKPGQAPRLLIYGAS-TRATGI PARFSGSGSGTEFTLTISSLQSED-FAVYYCQQYDDWPFTFGGGTKVEIK (SEQ ID NO:2, ADI-29379). In some embodiments, the antibody light chain variable domain is at least 95% identical to SEQ ID NO:2. In some embodiments, the light chain variable domain includes amino acid sequences RASQSVSSNLA (SEQ ID NO:14) as the first complementarity-determining region ("CDR"), GASTRAT (SEQ ID NO:15) as the second CDR, and QQYDDWPFT (SEQ ID NO:16) as the third CDR.

For example, an antibody heavy chain variable domain at least 90% identical to the amino acid sequence of SEQ ID NO:3 can be paired with an antibody light chain variable domain at least 90% identical to the amino acid sequence EIVLTQSPGTLSLSPGERATLSCRASQSVSSN-LAWYQQKPGQAPRLLIYGASTRATGIP ARFSGSGSGTEFTLTISSLQSEDFAVYYCQQD-DYWPPTFGGGTKVEIK (SEQ ID NO:4, ADI-29463). In some embodiments, the antibody light chain variable domain is at least 95% identical to SEQ ID NO:4. In some embodiments, the light chain variable domain includes amino acid sequences RASQSVSSNLA (SEQ ID NO:20) as the first complementarity-determining region ("CDR"), GASTRAT (SEQ ID NO:21) as the second CDR, and QQDDYWPPT (SEQ ID NO:22) as the third CDR.

For example, an antibody heavy chain variable domain at least 90% identical to the amino acid sequence of SEQ ID NO:5 can be paired with an antibody light chain variable domain at least 90% identical to the amino acid sequence DIQMTQSPSSVSASVGDRVTITCRASQGIDSWLAW-YQQKPGKAPKLLIYAASSLQSG VPSRFSGSGSGTD-FTLTISSLQPEDFATYYCQQGVSYPRTFGGGTKVEIK (SEQ ID NO:6, ADI-27744). In some embodiments, the antibody light chain variable domain is at least 95% identical to SEQ ID NO:6. In some embodiments, the light chain variable domain includes amino acid sequences RASQGID-SWLA (SEQ ID NO:26) as the first complementarity-determining region ("CDR"), AASSLQS (SEQ ID NO:27) as the second CDR, and QQGVSYPRT (SEQ ID NO:28) as the third CDR.

For example, an antibody heavy chain variable domain at least 90% identical to the amino acid sequence of SEQ ID NO:7 or 85 can be paired with an antibody light chain variable domain at least 90% identical to the amino acid sequence DIQMTQSPSSVSASVGDRVTITCRASQGISS-WLAWYQQKPGKAPKLLIYAASSLQSG VPSRFSGS-GSGTDFTLTISSLQPEDFATYYCQQGVSFPRTFGG-GTKVEIK (SEQ ID NO:8, ADI-27749). In some embodiments, the antibody light chain variable domain is at least 95% identical to SEQ ID NO:8. In some embodiments, the light chain variable domain includes amino acid sequences RASQGISSWLA (SEQ ID NO:32) as the first complementarity-determining region ("CDR"), AASSLQS (SEQ ID NO:33) as the second CDR, and QQGVSFPRT (SEQ ID NO:34) as the third CDR.

For example, an antibody heavy chain variable domain at least 90% identical to the amino acid sequence of SEQ ID NO:9 can be paired with an antibody light chain variable domain at least 90% identical to the amino acid sequence EIVLTQSPATLSLSPGERATLSCRASQSVSSYLAWYQ-QKPGQAPRLLIYDASNRATGI PARFSGSGSGT-DFTLTISSLEPEDFAVYYCQQSDNWPFTFGGG-TKVEIK (SEQ ID NO:10, ADI-29378). In some embodiments, the antibody light chain variable domain is at least 95% identical to SEQ ID NO:10. In some embodiments, the light chain variable domain includes amino acid sequences RASQSVSSYLA (SEQ ID NO:38) as the first complementarity-determining region ("CDR"), DASNRAT (SEQ ID NO:39) as the second CDR, and QQSDNWPFT (SEQ ID NO:40) as the third CDR.

When a heavy chain variable domain is combined with a light chain variable domain to form an antigen-binding site capable of binding NKG2D, the antigen-binding site can be included into a variety of structures, for example, a typical antibody structure with two identical heavy chains and two identical light chains, forming a pair of antigen-binding sites capable of binding NKG2D; a bi-specific, tri-specific, tetra-specific or other multi-specific antibody; or a smaller structure such as an scFv (in which the heavy chain variable domain is linked to the light chain variable domain).

In some embodiments, any NKG2D antigen-binding site disclosed in the instant invention is included into a protein that also includes a separate antigen-binding site that binds a tumor-associated antigen, which may permit the protein to simultaneously interact with an NK cell and a tumor cell. The tumor-associated antigen, for example, can be CD33, HER2, EpCAM, CD2, CD3, CD8, CD10, CD19, CD20, CD21, CD22, CD23, CD24, CD25, CD30, CD37, CD38, CD40, CD45RO, CD48, CD52, CD55, CD59, CD70, CD74, CD80, CD86, CD138, CD147, HLA-DR, CSAp, CA-125, TAG-72, EFGR/ERBB1, IGF1R, HER2, HER3, HER4, IGF-1R, c-Met, PDGFR, MUC1, MUC2, MUC3, MUC4, TNFR1, TNFR2, NGFR, TRAILR1, TRAILR2, Fas (CD95), DR3, DR4, DR5, DR6, VEGF, PlGF, tenascin, ED-B fibronectin, PSA, and IL-6, MAGE-A3, B7.1, B7.2, CTLA4 or PD1.

In some embodiments, any NKG2D antigen-binding site disclosed in the instant invention is included into a protein that also contain a tumor-associated antigen site and CD16 binding site. The CD16 binding site can be an additional antigen-binding site or an antibody constant region or a portion thereof, such as an IgG1 constant region (which may optionally include one or more mutations affecting, for example, effector activity or CD16 binding affinity).

Another aspect of the invention provides a method of enhancing tumor cell death and treating cancer in a patient. The method comprises administering to a patient in need thereof a therapeutically effective amount of a protein described herein to treat the cancer.

BRIEF DESCRIPTION OF THE DRAWINGS

FIG. 3A is the NKG2D-binding affinity of the NKG2D-binding domain ADI-27744 measured by surface plasmon resonance; FIG. 3B is the NKG2D-binding affinity of the NKG2D-binding domain ADI-29379 measured by surface plasmon resonance; FIG. 3C is the NKG2D-binding affinity of the NKG2D-binding domain ADI-27749 measured by surface plasmon resonance; FIG. 3D is the NKG2D-binding affinity of the NKG2D-binding domain ADI-29463 measured by surface plasmon resonance; and FIG. 3E is the NKG2D-binding affinity of the NKG2D-binding domain ADI-29378 measured by surface plasmon resonance.

FIG. 4A shows the profile of NKG2D monoclonal antibody comprising ADI-27744 injected over immobilized NKG2D, followed by injection of ULBP6. FIG. 4B shows the profile of ULBP6 injected over immobilized NKG2D, followed by injection of NKG2D monoclonal antibody comprising ADI-27744. FIG. 4C shows the profile of MS monoclonal antibody injected over immobilized NKG2D, followed by injection of ULBP6. FIG. 4D shows the profile of MS injected over the immobilized NKG2D, followed by injection of NKG2D monoclonal antibody comprising ADI-27744. FIG. 4E shows the profile of 1D11 injected over the immobilized NKG2D, followed by injection of NKG2D monoclonal antibody comprising ADI-27744. FIG. 4F shows the profile of MAB139 injected over the immobilized NKG2D, followed by injection of NKG2D monoclonal antibody comprising ADI-27744. FIG. 4G shows the profile of NKG2D monoclonal antibody comprising ADI-27744 was injected over the immobilized NKG2D, followed by injection of NKG2D monoclonal antibody comprising ADI-27749 (A49); and FIG. 4H shows the profile of NKG2D monoclonal antibody comprising ADI-27744 was injected over the immobilized NKG2D, followed by injection of NKG2D monoclonal antibody comprising F47.

FIG. 27A is an exemplary representation of one form of a κλ-Body; FIG. 27B is an exemplary representation of another κλ-Body.

DETAILED DESCRIPTION

Figure 1:
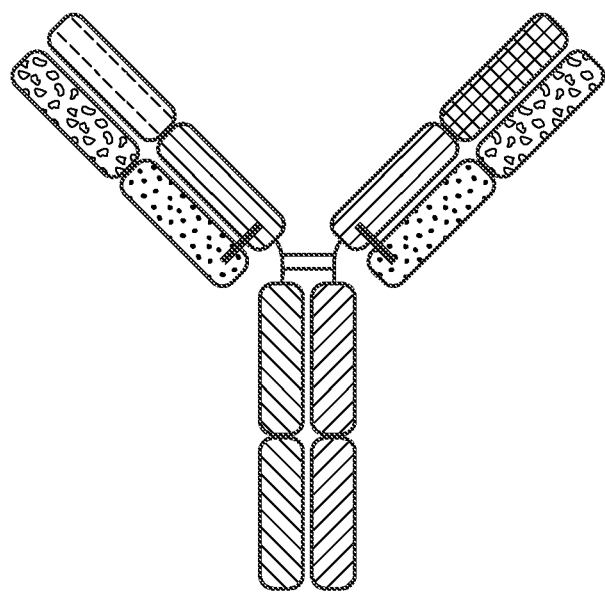
FIG. 1 is a representation of a multispecific binding protein that contains an NKG2D-binding domain (right arm), a tumor-associated antigen-binding domain (left arm) and an Fc domain or a portion thereof that binds to CD16.

The invention provides antibody heavy chain variable domains that can be paired with antibody light chain variable domains to form an antigen-binding site targeting the NKG2D receptor on natural killer cells, proteins that include the NKG2D antigen-binding sites, pharmaceutical compositions comprising such proteins, and therapeutic methods using such proteins and pharmaceutical compositions for the treatment of cancer. Various aspects of the invention are set forth below in sections; however, aspects of the invention described in one particular section are not to be limited to any particular section.

To facilitate an understanding of the present invention, a number of terms and phrases are defined below.

The terms "a" and "an" as used herein mean "one or more" and include the plural unless the context is inappropriate.

As used herein, the terms "subject" and "patient" refer to an organism to be treated by the methods and compositions described herein. Such organisms preferably include, but are not limited to, mammals (e.g., murines, simians, equines, bovines, porcines, canines, felines, and the like), and more preferably include humans.

As used herein, the term "antigen-binding site" refers to the part of the immunoglobulin molecule that participates in antigen binding. In human antibodies, the antigen-binding site is formed by amino acid residues of the N-terminal variable ("V") regions of the heavy ("H") and light ("L") chains. Three highly divergent stretches within the V regions of the heavy and light chains are referred to as "hypervariable regions" which are interposed between more conserved flanking stretches known as "framework regions," or "FRs." Thus the term "FR" refers to amino acid sequences which are naturally found between and adjacent to hypervariable regions in immunoglobulins. In a human antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs." In certain animals, such as camels and cartilaginous fish, the antigen-binding site is formed by a single antibody chain providing a "single domain antibody." Antigen-binding sites can exist in an intact antibody, in an antigen-binding fragment of an antibody that retains the antigen-binding surface, or in a recombinant polypeptide such as an scFv, using a peptide linker to connect the heavy chain variable domain to the light chain variable domain in a single polypeptide.

As used herein, the term "effective amount" refers to the amount of a compound (e.g., a compound of the present invention) sufficient to effect beneficial or desired results. An effective amount can be administered in one or more administrations, applications or dosages and is not intended to be limited to a particular formulation or administration route. As used herein, the term "treating" includes any effect, e.g., lessening, reducing, modulating, ameliorating or eliminating, that results in the improvement of the condition, disease, disorder, and the like, or ameliorating a symptom thereof.

As used herein, the term "pharmaceutical composition" refers to the combination of an active agent with a carrier, inert or active, making the composition especially suitable for diagnostic or therapeutic use in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants, see e.g., Martin, Remington's Pharmaceutical Sciences, 15th Ed., Mack Publ. Co., Easton, PA [1975].

Throughout the description, where compositions are described as having, including, or comprising specific components, or where processes and methods are described as having, including, or comprising specific steps, it is contemplated that, additionally, there are compositions of the present invention that consist essentially of, or consist of, the recited components, and that there are processes and methods according to the present invention that consist essentially of, or consist of, the recited processing steps.

As a general matter, compositions specifying a percentage are by weight unless otherwise specified. Further, if a variable is not accompanied by a definition, then the previous definition of the variable controls.

NKG2D Antigen-Binding Site

The invention provides antigen-binding sites that bind NKG2D, and antigen heavy chain variable domains that can be used to create such antigen-binding sites.

Antibody heavy chain variable domains and the light chain variable domains which they pair to form antigen-binding sites capable of binding and agonizing the NKG2D receptor have now been identified and are provided in Table 1, below. Unless otherwise indicated, the CDR sequences provided in Table 1 are determined under Kabat.

TABLE 1

| Clones | Heavy chain variable region amino acid sequence | Light chain variable region amino acid sequence |
| --- | --- | --- |
| ADI-29379 (E79) | QVQLVQSGAEVKKPGASVKVSCKAS GYTFTSYYMHWVRQAPGQGLEWMGI INPSGGSTSYAQKFQGRVTMTRDTSTS TVYMELSSLRSEDTAVYYCARGAPNY GDTTHDYYYMDVWGKGTTVTVSS (SEQ ID NO: 1) CDR1 non-Kabat (SEQ ID NO: 11) - YTFTSYYMH or CDR1 (SEQ ID NO: 45) - SYYMH CDR2 (SEQ ID NO: 12) - IINPSGGSTSYAQKFQG CDR3 non-Kabat (SEQ ID NO: 13) - | EIVMTQSPATLSVSPGERATLSC RASQSVSSNLAWYQQKPGQAPR LLIYGASTRATGIPARFSGSGSGT EFTLTISSLQSEDFAVYYCQQYD DWPFTFGGGTKVEIK (SEQ ID NO: 2) CDR1 (SEQ ID NO: 14) - RASQSVSSNLA CDR2 (SEQ ID NO: 15) - GASTRAT CDR3 (SEQ ID NO: 16) - QQYDDWPFT |

TABLE 1-continued

| Clones | Heavy chain variable region amino acid sequence | Light chain variable region amino acid sequence |
| --- | --- | --- |
| | ARGAPNYGDTTHDYYYMDV or CDR3 (SEQ ID NO: 68) - GAPNYGDTTHDYYYMDV | |
| ADI-29463 (F63) | QVQLVQSGAEVKKPGASVKVSCKAS GYTFTGYYMHWVRQAPGQGLEWMG WINPNSGGTNYAQKFQGRVTMTRDT SISTAYMELSRLRSDDTAVYYCARDT GEYYDTDDHGMDVWGQGTTVTVSS (SEQ ID NO: 3) CDR1 non-Kabat (SEQ ID NO: 17) - YTFTGYYMH or CDR1 (SEQ ID NO: 46) - GYYMH CDR2 (SEQ ID NO: 18) - WINPNSGGTNYAQKFQG CDR3 non-Kabat (SEQ ID NO: 19) - ARDTGEYYDTDDHGMDV or CDR3 (SEQ ID NO: 69) - DTGEYYDTDDHGMDV | EIVLTQSPGTLSLSPGERATLSCR ASQSVSSNLAWYQQKPGQAPRL LIYGASTRATGIPARFSGSGSGTE FTLTISSLQSEDFAVYYCQQDDY WPPTFGGGTKVEIK (SEQ ID NO: 4) CDR1 (SEQ ID NO: 20) - RASQSVSSNLA CDR2 (SEQ ID NO: 21) - GASTRAT CDR3 (SEQ ID NO: 22) - QQDDYWPPT |
| ADI-27744 (A44) | EVQLLESGGGLVQPGGSLRLSCAASG FTFSSYAMSWVRQAPGKGLEWVSAIS GSGGSTYYADSVKGRFTISRDNSKNT LYLQMNSLRAEDTAVYYCAKDGGYY DSGAGDYWGQGTLVTVSS (SEQ ID NO: 5) CDR1 non-Kabat (SEQ ID NO: 23) - FTFSSYAMS or CDR1 (SEQ ID NO: 47) - SYAMS CDR2 (SEQ ID NO: 24) - AISGSGGSTYYADSVKG CDR3 non-Kabat (SEQ ID NO: 25) - AKDGGYYDSGAGDY or CDR3 (SEQ ID NO: 70) - DGGYYDSGAGDY | DIQMTQSPSSVSASVGDRVTITC RASQGIDSWLAWYQQKPGKAP KLLIYAASSLQSGVPSRFSGSGS GTDFTLTISSLQPEDFATYYCQQ GVSYPRTFGGGTKVEIK (SEQ ID NO: 6) CDR1 (SEQ ID NO: 26) - RASQGIDSWLA CDR2 (SEQ ID NO: 27) - AASSLQS CDR3 (SEQ ID NO: 28) - QQGVSYPRT |
| ADI-27749 (A49) | EVQLVESGGGLVKPGGSLRLSCAASG FTFSSYSMNWVRQAPGKGLEWVSSIS SSSSYIYYADSVKGRFTISRDNAKNSL YLQMNSLRAEDTAVYYCARGAPMGA AAGWFDPWGQGTLVTVSS (SEQ ID NO: 7) CDR1 non-Kabat (SEQ ID NO: 29) - FTFSSYSMN or CDR1 (SEQ ID NO: 48) - SYSMN CDR2 (SEQ ID NO: 30) - SISSSSSYIYYADSVKG CDR3 non-Kabat (SEQ ID NO: 31) - ARGAPMGAAAGWFDP or CDR3 (SEQ ID NO: 71) - GAPMGAAAGWFDP | DIQMTQSPSSVSASVGDRVTITC RASQGISSWLAWYQQKPGKAP KLLIYAASSLQSGVPSRFSGSGS GTDFTLTISSLQPEDFATYYCQQ GVSFPRTFGGGTKVEIK (SEQ ID NO: 8) CDR1 (SEQ ID NO: 32) - RASQGISSWLA CDR2 (SEQ ID NO: 33) - AASSLQS CDR3 (SEQ ID NO: 34) - QQGVSFPRT |
| ADI-29378 (E78) | QVQLVQSGAEVKKPGASVKVSCKAS GYTFTSYYMEIWVRQAPGQGLEWMGI INPSGGSTSYAQKFQGRVTMTRDTSTS TVYMELSSLRSEDTAVYYCAREGAGF AYGMDYYYMDVWGKGTTVTVSS (SEQ ID NO: 9) CDR1 non-Kabat (SEQ ID NO: 35) - YTFTSYYMH or CDR1 (SEQ ID NO: 45) - SYYMI-1 CDR2 (SEQ ID NO: 36) - IINPSGGSTSYAQKFQG CDR3 non-Kabat (SEQ ID NO: 37) - AREGAGFAYGMDYYYMDV or CDR3 (SEQ ID NO: 72) - EGAGFAYGMDYYYMDV | EIVLTQSPATLSLSPGERATLSCR ASQSVSSYLAWYQQKPGQAPRL LIYDASNRATGIPARFSGSGSGT DFTLTISSLEPEDFAVYYCQQSD NWPPTFGGGTKVEIK (SEQ ID NO: 10) CDR1 (SEQ ID NO: 38) - RASQSVSSYLA CDR2 (SEQ ID NO: 39) - DASNRAT CDR3 (SEQ ID NO: 40) - QQSDNWPFT |
| A49MQ | EVQLVESGGGLVKPGGSLRLSCAASG FTFSSYSMNWVRQAPGKGLEWVSSIS SSSSYIYYADSVKGRFTISRDNAKNSL YLQMNSLRAEDTAVYYCARGAPQGA AAGWFDPWGQGTLVTVSS (SEQ ID NO: 83) CDR1 non-Kabat (SEQ ID NO: 29) - FTFSSYSMN or CDR1 (SEQ ID NO: 48) - SYSMN CDR2 (SEQ ID NO: 30) - SISSSSSYIYYADSVKG | DIQMTQSPSSVSASVGDRVTITC RASQGISSWLAWYQQKPGKAP KLLIYAASSLQSGVPSRFSGSGS GTDFTLTISSLQPEDFATYYCQQ GVSFPRTFGGGTKVEIK (SEQ ID NO: 8) CDR1 (SEQ ID NO: 32) - RASQGISSWLA CDR2 (SEQ ID NO: 33) - AASSLQS CDR3 (SEQ ID NO: 34) - QQGVSFPRT |

TABLE 1-continued

| Clones | Heavy chain variable region amino acid sequence | Light chain variable region amino acid sequence |
| --- | --- | --- |
| | CDR3 non-Kabat (SEQ ID NO: 73) - ARGAPQGAAAGWFDP or CDR3 (SEQ ID NO: 74) - GAPQGAAAGWFDP | |
| A49ML | EVQLVESGGGLVKPGGSLRLSCAASG FTFSSYSMNWVRQAPGKGLEWVSSIS SSSSYIYYADSVKGRFTISRDNAKNSL YLQMNSLRAEDTAVYYCARGAPLGA AAGWFDPWGQGTLVTVSS (SEQ ID NO: 84) CDR1 non-Kabat (SEQ ID NO: 29) - FTFSSYSMN or CDR1 (SEQ ID NO: 48) - SYSMN CDR2 (SEQ ID NO: 30) - SISSSSSYIYYADSVKG CDR3 non-Kabat (SEQ ID NO: 75) - ARGAPLGAAAGWFDP or CDR3 (SEQ ID NO: 76) - GAPLGAAAGWFDP | DIQMTQSPSSVSASVGDRVTITC RASQGISSWLAWYQQKPGKAP KLLIYAASSLQSGVPSRFSGSGS GTDFTLTISSLQPEDFATYYCQQ GVSFPRTFGGGTKVEIK (SEQ ID NO: 8) CDR1 (SEQ ID NO: 32) - RASQGISSWLA CDR2 (SEQ ID NO: 33) - AASSLQS CDR3 (SEQ ID NO: 34) - QQGVSFPRT |
| A49MI | EVQLVESGGGLVKPGGSLRLSCAASG FTFSSYSMNWVRQAPGKGLEWVSSIS SSSSYIYYADSVKGRFTISRDNAKNSL YLQMNSLRAEDTAVYYCARGAPIGA AAGWFDPWGQGTLVTVSS (SEQ ID NO: 85) CDR1 non-Kabat (SEQ ID NO: 29) - FTFSSYSMN or CDR1 (SEQ ID NO: 48) - SYSMN CDR2 (SEQ ID NO: 30) - SISSSSSYIYYADSVKG CDR3 non-Kabat (SEQ ID NO: 77) - ARGAPIGAAAGWFDP or CDR3 (SEQ ID NO: 78) - GAPIGAAAGWFDP | DIQMTQSPSSVSASVGDRVTITC RASQGISSWLAWYQQKPGKAP KLLIYAASSLQSGVPSRFSGSGS GTDFTLTISSLQPEDFATYYCQQ GVSFPRTFGGGTKVEIK (SEQ ID NO: 8) CDR1 (SEQ ID NO: 32) - RASQGISSWLA CDR2 (SEQ ID NO: 33) - AASSLQS CDR3 (SEQ ID NO: 34) - QQGVSFPRT |
| A49MF | EVQLVESGGGLVKPGGSLRLSCAASG FTFSSYSMNWVRQAPGKGLEWVSSIS SSSSYIYYADSVKGRFTISRDNAKNSL YLQMNSLRAEDTAVYYCARGAPFGA AAGWFDPWGQGTLVTVSS (SEQ ID NO: 86) CDR1 non-Kabat (SEQ ID NO: 29) - FTFSSYSMN or CDR1 (SEQ ID NO: 48) - SYSMN CDR2 (SEQ ID NO: 30) - SISSSSSYIYYADSVKG CDR3 non-Kabat (SEQ ID NO: 79) - ARGAPFGAAAGWFDP or CDR3 (SEQ ID NO: 80) - GAPFGAAAGWFDP | DIQMTQSPSSVSASVGDRVTITC RASQGISSWLAWYQQKPGKAP KLLIYAASSLQSGVPSRFSGSGS GTDFTLTISSLQPEDFATYYCQQ GVSFPRTFGGGTKVEIK (SEQ ID NO: 8) CDR1 (SEQ ID NO: 32) - RASQGISSWLA CDR2 (SEQ ID NO: 33) - AASSLQS CDR3 (SEQ ID NO: 34) - QQGVSFPRT |
| A49MV | EVQLVESGGGLVKPGGSLRLSCAASG FTFSSYSMNWVRQAPGKGLEWVSSIS SSSSYIYYADSVKGRFTISRDNAKNSL YLQMNSLRAEDTAVYYCARGAPVGA AAGWFDPWGQGTLVTVSS (SEQ ID NO: 41) CDR1 non-Kabat (SEQ ID NO: 29) - FTFSSYSMN or CDR1 (SEQ ID NO: 48) - SYSMN CDR2 (SEQ ID NO: 30) - SISSSSSYIYYADSVKG CDR3 non-Kabat (SEQ ID NO: 81) - ARGAPVGAAAGWFDP or CDR3 (SEQ ID NO: 82) - GAPVGAAAGWFDP | DIQMTQSPSSVSASVGDRVTITC RASQGISSWLAWYQQKPGKAP KLLIYAASSLQSGVPSRFSGSGS GTDFTLTISSLQPEDFATYYCQQ GVSFPRTFGGGTKVEIK (SEQ ID NO: 8) CDR1 (SEQ ID NO: 32) - RASQGISSWLA CDR2 (SEQ ID NO: 33) - AASSLQS CDR3 (SEQ ID NO: 34) - QQGVSFPRT |
| A49-consensus | EVQLVESGGGLVKPGGSLRLSCAASG FTFSSYSMNWVRQAPGKGLEWVSSIS SSSSYIYYADSVKGRFTISRDNAKNSL YLQMNSLRAEDTAVYYCARGAPXGA AAGWFDPWGQGTLVTVSS, wherein X is M, L, I, V, Q, or F (SEQ ID NO: 42) CDR1 non-Kabat (SEQ ID NO: 29) - FTFSSYSMN or CDR1 (SEQ ID NO: 48) - SYSMN CDR2 (SEQ ID NO: 30) - SISSSSSYIYYADSVKG | DIQMTQSPSSVSASVGDRVTITC RASQGISSWLAWYQQKPGKAP KLLIYAASSLQSGVPSRFSGSGS GTDFTLTISSLQPEDFATYYCQQ GVSFPRTFGGGTKVEIK (SEQ ID NO: 8) CDR1 (SEQ ID NO: 32) - RASQGISSWLA CDR2 (SEQ ID NO: 33) - AASSLQS CDR3 (SEQ ID NO: 34) - QQGVSFPRT |

TABLE 1-continued

| Clones | Heavy chain variable region amino acid sequence | Light chain variable region amino acid sequence |
|---|---|---|
| | CDR3 non-Kabat (SEQ ID NO: 43) - ARGAPXGAAAGWFDP or CDR3 (SEQ ID NO: 44) - GAPXGAAAGWFDP, wherein X is M, L, I, V. Q, or F | |

One advantage of one or more of the antibody heavy chain variable domain amino acid sequences described above is that they can bind to NKG2D from humans and cynomolgus monkeys to agonize the receptor, and compete with natural ligands for binding to the receptor. Additional antigen-binding sites that bind NKG2D and share one or more of these properties are also particularly useful and can be identified by binding competition assays known in the art. For example, the additional antigen-binding sites can be identified by competition with ADI-29379, ADI-29463, ADI-27744, ADI-27749, or ADI-29378 for binding to both human and optionally cynomolgus monkey NKG2D.

Another advantage of the NKG2D-binding sites which comprise the antibody heavy chain variable domains and light chain variable domains sequences described above is that they can bind to NKG2D with high affinity. In some embodiments, NKG2D-binding sites bind to NKG2D with a $K_D$ of 0.1 to 1000 nM. In some embodiments, NKG2D-binding sites bind to NKG2D with a $K_D$ of 1 to 500 nM. In some embodiments, NKG2D-binding sites bind to NKG2D with a $K_D$ of 5 to 100 nM. In some embodiments, NKG2D-binding sites bind to NKG2D with a $K_D$ of 10 to 62 nM.

In certain embodiments, the present invention provides an antigen-binding site that includes an antibody heavy chain variable domain that includes an amino acid sequence at least 90% (e.g., 91%, 92%, 93%, 94%, 95%, 96%, 97%, 98%, 99%, or 100%) identical to the amino acid sequence of SEQ ID NO:1, and an antibody light chain variable domain that includes an amino acid sequence at least 90% (e.g., 91%, 92%, 93%, 94%, 95%, 96%, 97%, 98%, 99%, or 100%) identical to SEQ ID NO:2. In certain embodiments, an antigen-binding site that includes an antibody heavy chain variable domain with an amino acid sequence at least 90% (e.g., 91%, 92%, 93%, 94%, 95%, 96%, 97%, 98%, 99%, or 100%) identical to the amino acid sequence of SEQ ID NO:1, includes a CDR1 sequence represented by the amino acid sequence of SEQ ID NO:11 or SEQ ID NO:91, a CDR2 sequence represented by the amino acid sequence of SEQ ID NO:12, and a CDR3 sequence represented by the amino acid sequence of SEQ ID NO:13 or 68. In certain embodiments, an antigen-binding site that includes an antibody light chain variable domain with an amino acid sequence at least 90% (e.g., 91%, 92%, 93%, 94%, 95%, 96%, 97%, 98%, 99%, or 100%) identical to the amino acid sequence of SEQ ID NO:2, includes a CDR1 sequence represented by the amino acid sequence of SEQ ID NO:14, a CDR2 sequence represented by the amino acid sequence of SEQ ID NO:15, and a CDR3 sequence represented by the amino acid sequence of SEQ ID NO:16.

In certain embodiments, the present invention provides an antigen-binding site that includes an antibody heavy chain variable domain that includes an amino acid sequence at least 90% (e.g., 91%, 92%, 93%, 94%, 95%, 96%, 97%, 98%, 99%, or 100%) identical to the amino acid sequence of SEQ ID NO:3, and an antibody light chain variable domain that includes an amino acid sequence at least 90% (e.g., 91%, 92%, 93%, 94%, 95%, 96%, 97%, 98%, 99%, or 100%) identical to SEQ ID NO:4. In certain embodiments, an antigen-binding site that includes an antibody heavy chain variable domain with an amino acid sequence at least 90% (e.g., 91%, 92%, 93%, 94%, 95%, 96%, 97%, 98%, 99%, or 100%) identical to the amino acid sequence of SEQ ID NO:3, includes a CDR1 sequence represented by the amino acid sequence of SEQ ID NO:17 or SEQ ID NO:92, a CDR2 sequence represented by the amino acid sequence of SEQ ID NO:18, and a CDR3 sequence represented by the amino acid sequence of SEQ ID NO:19 or SEQ ID NO:69. In certain embodiments, an antigen-binding site that includes an antibody light chain variable domain with an amino acid sequence at least 90% (e.g., 91%, 92%, 93%, 94%, 95%, 96%, 97%, 98%, 99%, or 100%) identical to the amino acid sequence of SEQ ID NO:4, includes a CDR1 sequence represented by the amino acid sequence of SEQ ID NO:20, a CDR2 sequence represented by the amino acid sequence of SEQ ID NO:21, and a CDR3 sequence represented by the amino acid sequence of SEQ ID NO:22.

In certain embodiments, the present invention provides an antigen-binding site that includes an antibody heavy chain variable domain that includes an amino acid sequence at least 90% (e.g., 91%, 92%, 93%, 94%, 95%, 96%, 97%, 98%, 99%, or 100%) identical to the amino acid sequence of SEQ ID NO:5, and an antibody light chain variable domain that includes an amino acid sequence at least 90% (e.g., 91%, 92%, 93%, 94%, 95%, 96%, 97%, 98%, 99%, or 100%) identical to SEQ ID NO:6. In certain embodiments, an antigen-binding site that includes an antibody heavy chain variable domain with an amino acid sequence at least 90% (e.g., 91%, 92%, 93%, 94%, 95%, 96%, 97%, 98%, 99%, or 100%) identical to the amino acid sequence of SEQ ID NO:5, includes a CDR1 sequence represented by the amino acid sequence of SEQ ID NO:23 or SEQ ID NO:93, a CDR2 sequence represented by the amino acid sequence of SEQ ID NO:24, and a CDR3 sequence represented by the amino acid sequence of SEQ ID NO:25 or SEQ ID NO:70. In certain embodiments, an antigen-binding site that includes an antibody light chain variable domain with an amino acid sequence at least 90% (e.g., 91%, 92%, 93%, 94%, 95%, 96%, 97%, 98%, 99%, or 100%) identical to the amino acid sequence of SEQ ID NO:6, includes a CDR1 sequence represented by the amino acid sequence of SEQ ID NO:26, a CDR2 sequence represented by the amino acid sequence of SEQ ID NO:27, and a CDR3 sequence represented by the amino acid sequence of SEQ ID NO:28.

In certain embodiments, the present invention provides an antigen-binding site that includes an antibody heavy chain variable domain that includes an amino acid sequence at least 90% (e.g., 91%, 92%, 93%, 94%, 95%, 96%, 97%, 98%, 99%, or 100%) identical to the amino acid sequence of SEQ ID NO:7, and an antibody light chain variable domain that includes an amino acid sequence at least 90% (e.g., 91%, 92%, 93%, 94%, 95%, 96%, 97%, 98%, 99%, or 100%) identical to SEQ ID NO:8. In certain embodiments, an antigen-binding site that includes an antibody heavy chain variable domain with an amino acid sequence at least 90% (e.g., 91%, 92%, 93%, 94%, 95%, 96%, 97%, 98%, 99%, or 100%) identical to the amino acid sequence of SEQ ID NO:7, includes a CDR1 sequence represented by the amino acid sequence of SEQ ID NO:29 or SEQ ID NO:94, a CDR2 sequence represented by the amino acid sequence of SEQ ID NO:30, and a CDR3 sequence represented by the amino acid sequence of SEQ ID NO:31 or SEQ ID NO:71. In certain embodiments, an antigen-binding site that includes an antibody light chain variable domain with an amino acid sequence at least 90% (e.g., 91%, 92%, 93%, 94%, 95%, 96%, 97%, 98%, 99%, or 100%) identical to the amino acid sequence of SEQ ID NO:8, includes a CDR1 sequence represented by the amino acid sequence of SEQ ID NO:32, a CDR2 sequence represented by the amino acid sequence of SEQ ID NO:33, and a CDR3 sequence represented by the amino acid sequence of SEQ ID NO:34.

The amino acid residue M at position 102 of SEQ ID NO:7, which is in CDR3 of the heavy chain variable domain, can be mutated. In certain embodiments, M102 is substituted by a non-charged residue. In certain embodiments, M102 is substituted by a hydrophobic residue (Gly, Ala, Val, Leu, Ile, Pro, Phe, or Trp). In certain embodiments, M102 is substituted by a polar residue (Ser, Thr, Cys, Asn, Gln, or Tyr). In certain embodiments, M102 is substituted by Leu, Ile, Val, Gln, or Phe.

Accordingly, in certain embodiments, the present invention provides an antigen-binding site that includes an antibody heavy chain variable domain that includes an amino acid sequence at least 90% (e.g., 91%, 92%, 93%, 94%, 95%, 96%, 97%, 98%, 99%, or 100%) identical to the amino acid sequence of SEQ ID NO:83, and an antibody light chain variable domain that includes an amino acid sequence at least 90% (e.g., 91%, 92%, 93%, 94%, 95%, 96%, 97%, 98%, 99%, or 100%) identical to SEQ ID NO:8. In certain embodiments, an antigen-binding site that includes an antibody heavy chain variable domain with an amino acid sequence at least 90% (e.g., 91%, 92%, 93%, 94%, 95%, 96%, 97%, 98%, 99%, or 100%) identical to the amino acid sequence of SEQ ID NO:83, includes a CDR1 sequence represented by the amino acid sequence of SEQ ID NO:29 or SEQ ID NO:94, a CDR2 sequence represented by the amino acid sequence of SEQ ID NO:30, and a CDR3 sequence represented by the amino acid sequence of SEQ ID NO:73 or SEQ ID NO:74. In certain embodiments, an antigen-binding site that includes an antibody light chain variable domain with an amino acid sequence at least 90% (e.g., 91%, 92%, 93%, 94%, 95%, 96%, 97%, 98%, 99%, or 100%) identical to the amino acid sequence of SEQ ID NO:8, includes a CDR1 sequence represented by the amino acid sequence of SEQ ID NO:32, a CDR2 sequence represented by the amino acid sequence of SEQ ID NO:33, and a CDR3 sequence represented by the amino acid sequence of SEQ ID NO:34.

In certain embodiments, the present invention provides an antigen-binding site that includes an antibody heavy chain variable domain that includes an amino acid sequence at least 90% (e.g., 91%, 92%, 93%, 94%, 95%, 96%, 97%, 98%, 99%, or 100%) identical to the amino acid sequence of SEQ ID NO:84, and an antibody light chain variable domain that includes an amino acid sequence at least 90% (e.g., 91%, 92%, 93%, 94%, 95%, 96%, 97%, 98%, 99%, or 100%) identical to SEQ ID NO:8. In certain embodiments, an antigen-binding site that includes an antibody heavy chain variable domain with an amino acid sequence at least 90% (e.g., 91%, 92%, 93%, 94%, 95%, 96%, 97%, 98%, 99%, or 100%) identical to the amino acid sequence of SEQ ID NO:84, includes a CDR1 sequence represented by the amino acid sequence of SEQ ID NO:29 or SEQ ID NO:94, a CDR2 sequence represented by the amino acid sequence of SEQ ID NO:30, and a CDR3 sequence represented by the amino acid sequence of SEQ ID NO:75 or SEQ ID NO:76. In certain embodiments, an antigen-binding site that includes an antibody light chain variable domain with an amino acid sequence at least 90% (e.g., 91%, 92%, 93%, 94%, 95%, 96%, 97%, 98%, 99%, or 100%) identical to the amino acid sequence of SEQ ID NO:8, includes a CDR1 sequence represented by the amino acid sequence of SEQ ID NO:32, a CDR2 sequence represented by the amino acid sequence of SEQ ID NO:33, and a CDR3 sequence represented by the amino acid sequence of SEQ ID NO:34.

In certain embodiments, the present invention provides an antigen-binding site that includes an antibody heavy chain variable domain that includes an amino acid sequence at least 90% (e.g., 91%, 92%, 93%, 94%, 95%, 96%, 97%, 98%, 99%, or 100%) identical to the amino acid sequence of SEQ ID NO:85, and an antibody light chain variable domain that includes an amino acid sequence at least 90% (e.g., 91%, 92%, 93%, 94%, 95%, 96%, 97%, 98%, 99%, or 100%) identical to SEQ ID NO:8. In certain embodiments, an antigen-binding site that includes an antibody heavy chain variable domain with an amino acid sequence at least 90% (e.g., 91%, 92%, 93%, 94%, 95%, 96%, 97%, 98%, 99%, or 100%) identical to the amino acid sequence of SEQ ID NO:85, includes a CDR1 sequence represented by the amino acid sequence of SEQ ID NO:29 or SEQ ID NO:94, a CDR2 sequence represented by the amino acid sequence of SEQ ID NO:30, and a CDR3 sequence represented by the amino acid sequence of SEQ ID NO:77 or SEQ ID NO:78. In certain embodiments, an antigen-binding site that includes an antibody light chain variable domain with an amino acid sequence at least 90% (e.g., 91%, 92%, 93%, 94%, 95%, 96%, 97%, 98%, 99%, or 100%) identical to the amino acid sequence of SEQ ID NO:8, includes a CDR1 sequence represented by the amino acid sequence of SEQ ID NO:32, a CDR2 sequence represented by the amino acid sequence of SEQ ID NO:33, and a CDR3 sequence represented by the amino acid sequence of SEQ ID NO:34.

In certain embodiments, the present invention provides an antigen-binding site that includes an antibody heavy chain variable domain that includes an amino acid sequence at least 90% (e.g., 91%, 92%, 93%, 94%, 95%, 96%, 97%, 98%, 99%, or 100%) identical to the amino acid sequence of SEQ ID NO:86, and an antibody light chain variable domain that includes an amino acid sequence at least 90% (e.g., 91%, 92%, 93%, 94%, 95%, 96%, 97%, 98%, 99%, or 100%) identical to SEQ ID NO:8. In certain embodiments, an antigen-binding site that includes an antibody heavy chain variable domain with an amino acid sequence at least 90% (e.g., 91%, 92%, 93%, 94%, 95%, 96%, 97%, 98%, 99%, or 100%) identical to the amino acid sequence of SEQ ID NO:86, includes a CDR1 sequence represented by the amino acid sequence of SEQ ID NO:29 or SEQ ID NO:94, a CDR2 sequence represented by the amino acid sequence of SEQ ID NO:30, and a CDR3 sequence represented by the amino acid sequence of SEQ ID NO:79 or 80. In certain embodiments, an antigen-binding site that includes an antibody light chain variable domain with an amino acid sequence at least 90% (e.g., 91%, 92%, 93%, 94%, 95%, 96%, 97%, 98%, 99%, or 100%) identical to the amino acid sequence of SEQ ID NO:8, includes a CDR1 sequence represented by the amino acid sequence of SEQ ID NO:32, a CDR2 sequence represented by the amino acid sequence of SEQ ID NO:33, and a CDR3 sequence represented by the amino acid sequence of SEQ ID NO:34.

In certain embodiments, the present invention provides an antigen-binding site that includes an antibody heavy chain variable domain that includes an amino acid sequence at least 90% (e.g., 91%, 92%, 93%, 94%, 95%, 96%, 97%, 98%, 99%, or 100%) identical to the amino acid sequence of SEQ ID NO:41, and an antibody light chain variable domain that includes an amino acid sequence at least 90% (e.g., 91%, 92%, 93%, 94%, 95%, 96%, 97%, 98%, 99%, or 100%) identical to SEQ ID NO:8. In certain embodiments, an antigen-binding site that includes an antibody heavy chain variable domain with an amino acid sequence at least 90% (e.g., 91%, 92%, 93%, 94%, 95%, 96%, 97%, 98%, 99%, or 100%) identical to the amino acid sequence of SEQ ID NO:41, includes a CDR1 sequence represented by the amino acid sequence of SEQ ID NO:29 or SEQ ID NO:94, a CDR2 sequence represented by the amino acid sequence of SEQ ID NO:30, and a CDR3 sequence represented by the amino acid sequence of SEQ ID NO:81 or SEQ ID NO:82. In certain embodiments, an antigen-binding site that includes an antibody light chain variable domain with an amino acid sequence at least 90% (e.g., 91%, 92%, 93%, 94%, 95%, 96%, 97%, 98%, 99%, or 100%) identical to the amino acid sequence of SEQ ID NO:8, includes a CDR1 sequence represented by the amino acid sequence of SEQ ID NO:32, a CDR2 sequence represented by the amino acid sequence of SEQ ID NO:33, and a CDR3 sequence represented by the amino acid sequence of SEQ ID NO:34.

In certain embodiments, the present invention provides an antigen-binding site that includes an antibody heavy chain variable domain that includes an amino acid sequence at least 90% (e.g., 91%, 92%, 93%, 94%, 95%, 96%, 97%, 98%, 99%, or 100%) identical to the amino acid sequence of SEQ ID NO:9, and an antibody light chain variable domain that includes an amino acid sequence at least 90% (e.g., 91%, 92%, 93%, 94%, 95%, 96%, 97%, 98%, 99%, or 100%) identical to SEQ ID NO:10. In certain embodiments, an antigen-binding site that includes an antibody heavy chain variable domain with an amino acid sequence at least 90% (e.g., 91%, 92%, 93%, 94%, 95%, 96%, 97%, 98%, 99%, or 100%) identical to the amino acid sequence of SEQ ID NO:9, includes a CDR1 sequence represented by the amino acid sequence of SEQ ID NO:35 or SEQ ID NO:91, a CDR2 sequence represented by the amino acid sequence of SEQ ID NO:36, and a CDR3 sequence represented by the amino acid sequence of SEQ ID NO:37 or SEQ ID NO:72. In certain embodiments, an antigen-binding site that includes an antibody light chain variable domain with an amino acid sequence at least 90% (e.g., 91%, 92%, 93%, 94%, 95%, 96%, 97%, 98%, 99%, or 100%) identical to the amino acid sequence of SEQ ID NO:10, includes a CDR1 sequence represented by the amino acid sequence of SEQ ID NO:38, a CDR2 sequence represented by the amino acid sequence of SEQ ID NO:39, and a CDR3 sequence represented by the amino acid sequence of SEQ ID NO:40.

In certain embodiments, the present invention provides an antigen-binding site that includes an antibody heavy chain variable domain that includes an amino acid sequence at least 90% (e.g., 91%, 92%, 93%, 94%, 95%, 96%, 97%, 98%, 99%, or 100%) identical to the amino acid sequence of SEQ ID NO:5, and an antibody light chain variable domain that includes an amino acid sequence at least 90% (e.g., 91%, 92%, 93%, 94%, 95%, 96%, 97%, 98%, 99%, or 100%) identical to SEQ ID NO:6, that does not block the binding of anti-NKG2D antibodies MS, 1D11, and MAB139 to NKG2D.

In embodiments, an antigen-binding site that includes an antibody heavy chain variable domain that includes an amino acid sequence at least 90% (e.g., 91%, 92%, 93%, 94%, 95%, 96%, 97%, 98%, 99%, or 100%) identical to the amino acid sequence of SEQ ID NO:7, 83, 84, 85, 86, or 87, and an antibody light chain variable domain that includes an amino acid sequence at least 90% (e.g., 91%, 92%, 93%, 94%, 95%, 96%, 97%, 98%, 99%, or 100%) identical to SEQ ID NO:8, does not block binding of an antigen-binding site that includes an antibody heavy chain variable domain that includes an amino acid sequence at least 90% (e.g., 91%, 92%, 93%, 94%, 95%, 96%, 97%, 98%, 99%, or 100%) identical to the amino acid sequence of SEQ ID NO:5, and an antibody light chain variable domain that includes an amino acid sequence at least 90% (e.g., 91%, 92%, 93%, 94%, 95%, 96%, 97%, 98%, 99%, or 100%) identical to SEQ ID NO:6 to NKG2D.

In certain embodiments, an antigen-binding site that includes an antibody heavy chain variable domain that includes an amino acid sequence at least 90% (e.g., 91%, 92%, 93%, 94%, 95%, 96%, 97%, 98%, 99%, or 100%) identical to the amino acid sequence of SEQ ID NO:5, and an antibody light chain variable domain that includes an amino acid sequence at least 90% (e.g., 91%, 92%, 93%, 94%, 95%, 96%, 97%, 98%, 99%, or 100%) identical to SEQ ID NO:6, binds to a unique epitope on NKG2D, different from MS, 1D11, MAB139, ADI-27749 and F47 binding epitope(s).

Antibodies and Multi-Specific Binding Proteins

In some embodiments of this invention, the NKG2D antigen-binding sites formed by pairing an antibody heavy chain variable domain with a light chain variable domain described herein can be included into larger proteins such as intact antibodies, multi-specific binding proteins or multi-specific binding antibodies. For example, an NKG2D-binding site can be combined with a second component, e.g., a second antigen-binding site. In some embodiments, the second antigen-binding site binds to one or more tumor-associated antigens, such as CD33, HER2, EpCAM, CD2, CD3, CD8, CD10, CD19, CD20, CD21, CD22, CD23, CD24, CD25, CD30, CD33, CD37, CD38, CD40, CD45RO, CD48, CD52, CD55, CD59, CD70, CD74, CD80, CD86, CD138, CD147, HLA-DR, CSAp, CA-125, TAG-72, EFGR/ERBB1, IGF1R, HER3, HER4, IGF-1R, c-Met, PDGFR, MUC1, MUC2, MUC3, MUC4, TNFR1, TNFR2, NGFR, TRAILR1, TRATLR2, Fas (CD95), DR3, DR4, DR5, DR6, VEGF, PIGF, tenascin, ED-B fibronectin, PSA, and IL-6, MAGE-A3, B7.1, B7.2, CTLA4 or PD1. Binding of a multi-specific protein to NKG2D and to a tumor-associated antigen on a cancer cell brings the cancer cell into proximity to the natural killer cell, which facilitates destruction of the cancer cell by the natural killer cell either directly or indirectly.

In some embodiments, in addition to an NKG2D-binding site and a tumor-associated antigen-binding site, a multi-specific binding protein can further include a domain that binds to CD16, an Fc receptor on the surface of leukocytes including natural killer cells, macrophages, neutrophils, eosinophils, mast cells, and follicular dendritic cells. In some embodiments, the CD16 binding domain can include an antibody Fc region or a portion thereof. In some embodiments, the domain that binds to CD16 contains hinge, CH2 and CH3 domains of an antibody Fc region without or without CH1 domain. In some embodiments, the antibody Fc region is derived from the Fc regions in the human and/or other mammalian immunoglobulins. It is known that within the Fc region, CD16 binding is mediated by the hinge region and the CH2 domain. For example, within human IgG1, the interaction with CD16 is mediated through amino acid residues Asp 265-Glu 269, Asn 297-Thr 299, Ala 327-Ile 332, Leu 234-Ser 239, and carbohydrate residue N-acetyl-D-glucosamine in the CH2 domain (see Sondermann et al, Nature, 406(6793):267-273). Based on the known domains and amino acid residues, in some embodiments, mutations can be selected within the CD16 binding domain to enhance or reduce its binding affinity to CD16. Selection methods are well known methods in the art, such as phage-displayed libraries or yeast surface-displayed cDNA libraries. Appropriate selection methods can also be designed based on the known three-dimensional structure of the interaction by a skilled person in the art.

The multi-specific binding proteins described herein can take various formats. For example, one format is a heterodimeric, multi-specific antibody that includes a first immunoglobulin heavy chain, a first immunoglobulin light chain, a second immunoglobulin heavy chain and a second immunoglobulin light chain. The first immunoglobulin heavy chain includes a first Fc (hinge-CH2-CH3) domain, a first heavy chain variable domain and optionally a first CH1 heavy chain domain. The first immunoglobulin light chain includes a first light chain variable domain and a first light chain constant domain. The first immunoglobulin light chain, together with the first immunoglobulin heavy chain, forms an antigen-binding site that binds NKG2D. The second immunoglobulin heavy chain comprises a second Fc (hinge-CH2-CH3) domain, a second heavy chain variable domain and optionally a second CH1 heavy chain domain. The second immunoglobulin light chain includes a second light chain variable domain and a second light chain constant domain. The second immunoglobulin light chain, together with the second immunoglobulin heavy chain, forms an antigen-binding site that binds a tumor antigen. The first Fc domain and second Fc domain together are able to bind to CD16 (FIG. 1).

Figure 2:
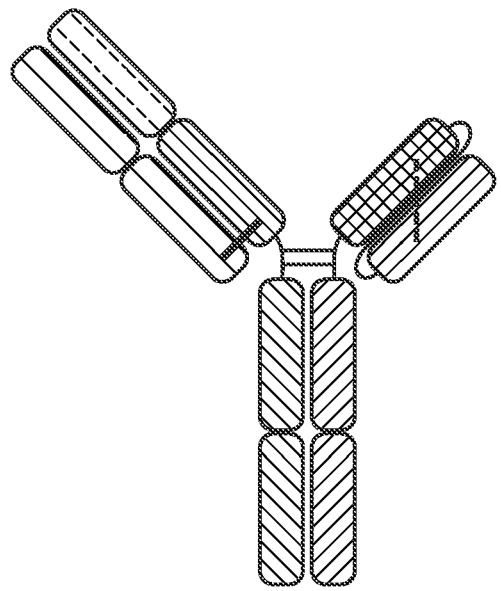
FIG. 2 is a representation of a multispecific binding protein that includes a NKG2D-binding domain or a tumor-associated antigen-binding domain, either one of which can be in an scFv format, and an Fc domain or a portion thereof that binds to CD16.
Figure 3A:
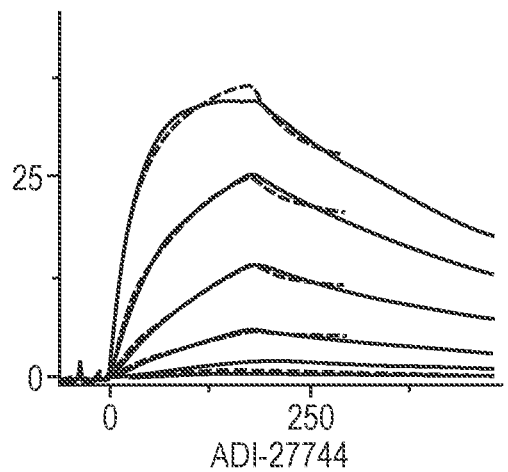
FIGS. 3A-3E are profiles of NKG2D-binding affinity of the NKG2D-binding domains measured by surface plasmon resonance.
Figure 3B:
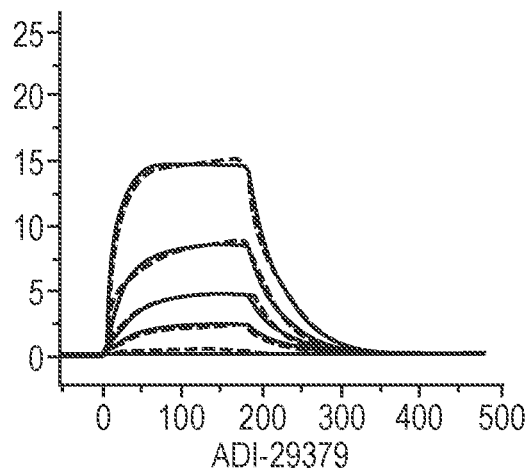
Figure 3C:
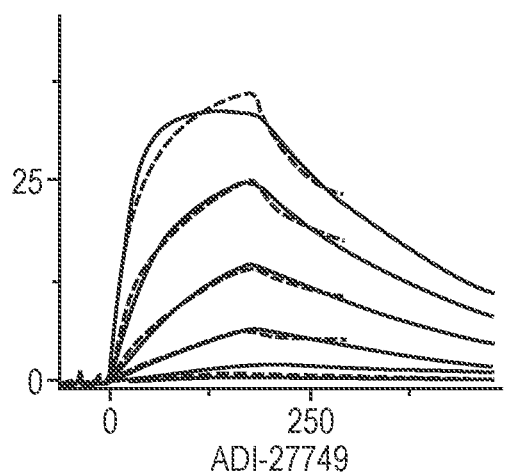
Figure 3D:
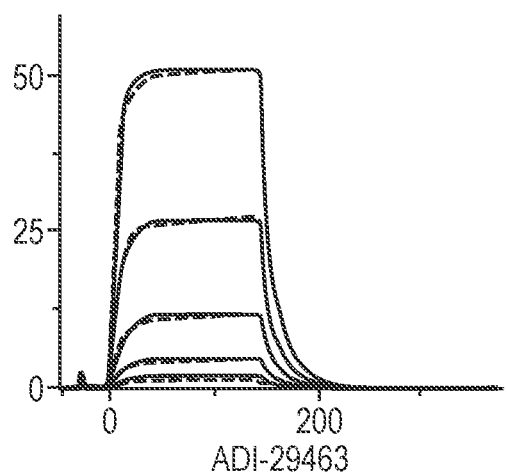
Figure 3E:
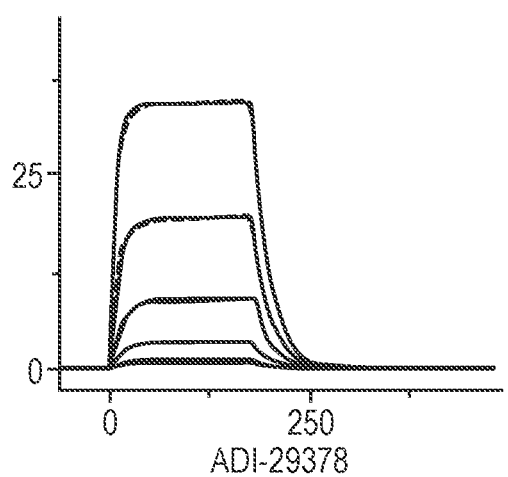

Another exemplary format involves a heterodimeric, multi-specific antibody that includes a first immunoglobulin heavy chain, a second immunoglobulin heavy chain and an immunoglobulin light chain. The first immunoglobulin heavy chain includes a first Fc (hinge-CH2-CH3) domain fused via either a linker or an antibody hinge to a single-chain variable fragment (scFv) composed of a heavy variable domain and light chain variable domain which pair and bind NKG2D. The second immunoglobulin heavy chain includes a second Fc (hinge-CH2-CH3) domain, a second heavy chain variable domain and optionally a CH1 heavy chain domain. The immunoglobulin light chain includes a light chain variable domain and a constant light chain domain. The second immunoglobulin heavy chain pairs with the immunoglobulin light chain and binds to a tumor-associated antigen. The first Fc domain and the second Fc domain together are able to bind to CD16 (FIG. 2). Additional formats of the multi-specific binding proteins can be devised by combining various formats of NKG2D-binding-fragments described herein.

One or more additional binding motifs may be fused to the C-terminus of the constant region CH3 domain, optionally via a linker sequence. In certain embodiments, the antigen-binding site could be a single-chain or disulfide-stabilized variable region (scFv) or could form a tetravalent or trivalent molecule.

In some embodiments, the multi-specific binding protein is in the Triomab form, which is a trifunctional, bispecific antibody that maintains an IgG-like shape. This chimera consists of two half antibodies, each with one light and one heavy chain, that originate from two parental antibodies. Triomab form is an heterodimeric construct containing ½ of rat antibody and ½ of mouse antibody.

In some embodiments, the multi-specific binding protein is the KiH Common Light Chain (LC) form, which involves the knobs-into-holes (KIHs) technology. The KIH involves engineering $C_H3$ domains to create either a "knob" or a "hole" in each heavy chain to promote heterodimerization. The concept behind the "Knobs-into-Holes (KiH)" Fc technology was to introduce a "knob" in one CH3 domain (CH3A) by substitution of a small residue with a bulky one (i.e., $T366W_{CH3A}$ in EU numbering). To accommodate the "knob," a complementary "hole" surface was created on the other CH3 domain (CH3B) by replacing the closest neighboring residues to the knob with smaller ones (i.e., T366S/L368A/$Y407V_{CH3B}$). The "hole" mutation was optimized by structured-guided phage library screening (Atwell S, Ridgway J B, Wells J A, Carter P. Stable heterodimers from remodeling the domain interface of a homodimer using a phage display library. J Mol Biol (1997) 270(1):26-35). X-ray crystal structures of KiH Fc variants (Elliott J M, Ultsch M, Lee J, Tong R, Takeda K, Spiess C, et al., Antiparallel conformation of knob and hole aglycosylated half-antibody homodimers is mediated by a CH2-CH3 hydrophobic interaction. J Mol Biol (2014) 426(9):1947-57; Mimoto F, Kadono S, Katada H, Igawa T, Kamikawa T, Hattori K. Crystal structure of a novel asymmetrically engineered Fc variant with improved affinity for FcgammaRs. Mol Immunol (2014) 58(1):132-8) demonstrated that heterodimerization is thermodynamically favored by hydrophobic interactions driven by steric complementarity at the inter-CH3 domain core interface, whereas the knob-knob and the hole-hole interfaces do not favor homodimerization owing to steric hindrance and disruption of the favorable interactions, respectively.

In some embodiments, the multi-specific binding protein is in the dual-variable domain immunoglobulin (DVD-Ig™) form, which combines the target binding domains of two monoclonal antibodies via flexible naturally occurring linkers, and yields a tetravalent IgG-like molecule. DVD-Ig™ is an homodimeric construct where variable domain targeting antigen 2 is fused to the N terminus of variable domain of Fab targeting antigen 1 Construct contains normal Fc.

In some embodiments, the multi-specific binding protein is in the Orthogonal Fab interface (Ortho-Fab) form, which is an heterodimeric construct that contains 2 Fabs binding to target 1 and target 2 fused to Fc. LC-HC pairing is ensured by orthogonal interface. Heterodimerization is ensured by mutations in the Fc. In ortho-Fab IgG approach (Lewis S M, Wu X, Pustilnik A, Sereno A, Huang F, Rick H L, et al. Generation of bispecific IgG antibodies by structure-based design of an orthogonal Fab interface. Nat. Biotechnol. (2014) 32(2):191-8), structure-based regional design introduces complementary mutations at the LC and $HC_{VH-CH1}$ interface in only one Fab, without any changes being made to the other Fab.

In some embodiments, the multi-specific binding protein is in the 2-in-1 Ig format. In some embodiments, the multi-specific binding protein is in the ES form, which is an heterodimeric construct containing 2 different Fabs binding to target 1 and target 2 fused to the Fc. Heterodimerization is ensured by electrostatic steering mutations in the Fc.

In some embodiments, the multi-specific binding protein is in the κλ-Body form, which are an heterodimeric constructs with 2 different Fabs fused to Fc stabilized by heterodimerization mutations: Fab targeting antigen 1 contains kappa LC, while second Fab targeting antigen 2 contains lambda LC.

In some embodiments, the multi-specific binding protein is in Fab Arm Exchange form (antibodies that exchange Fab arms by swapping a heavy chain and attached light chain (half-molecule) with a heavy-light chain pair from another molecule, which results in bispecific antibodies). Fab Arm Exchange form (cFae) is a heterodimer containing 2 Fabs binding to target 1 and 2, and an Fc stabilized by heterodimerization mutations.

In some embodiments, the multi-specific binding protein is in the SEED Body form which is an heterodimer containing 2 Fabs binding to target 1 and 2, and an Fc stabilized by heterodimerization mutations. The strand-exchange engineered domain (SEED) platform was designed to generate asymmetric and bispecific antibody-like molecules, a capability that expands therapeutic applications of natural antibodies. This protein engineered platform is based on exchanging structurally related sequences of immunoglobulin within the conserved CH3 domains. The SEED design allows efficient generation of AG/GA heterodimers, while disfavoring homodimerization of AG and GA SEED CH3 domains. (Muda M. et al., *Protein Eng. Des. Sel.* (2011, 24(5):447-54)).

In some embodiments, the multi-specific binding protein is in the LuZ-Y form, in which leucine zipper is used to induce heterodimerization of two different HCs. (Wranik, B J. et al., *J. Biol. Chem.* (2012), 287:43331-9). LuZ-Y form is a heterodimer containing 2 different scFabs binding to target 1 and 2, fused to Fc. Heterodimerization is ensured through leucine zipper motifs fused to C-terminus of Fc.

In some embodiments, the multi-specific binding protein is in the Cov-X-Body form (In bispecific CovX-Bodies, two different peptides are joined together using a branched azetidinone linker and fused to the scaffold antibody under mild conditions in a site-specific manner. Whereas the pharmacophores are responsible for functional activities, the antibody scaffold imparts long half-life and Ig-like distribution. The pharmacophores can be chemically optimized or replaced with other pharmacophores to generate optimized or unique bispecific antibodies. (Doppalapudi V R et al., *PNAS* (2010), 107(52); 22611-22616).

In some embodiments, the multi-specific binding protein is in an Oasc-Fab heterodimeric format that includes Fab binding to target 1 and scFab binding to target 2 fused to Fc. Heterodimerization is ensured by mutations in the Fc.

In some embodiments, the multi-specific binding protein is in an DuetMab format containing 2 different Fabs binding to antigen 1 and 2 and Fc stabilized by heterodimerization mutations. Fab 1 and 2 contain differential S-S bridges that ensure correct LC and HC pairing.

In some embodiments, the multi-specific binding protein is in an CrossmAb format which is an heterodimeric construct with 2 different Fabs binding to Target 1 and 2 fused to Fc stabilized by heterodimerization. CL and CH1 domains and VH and VL domains are switched, e.g. CH1 is fused in-line with VL, while CL is fused in-line with VH.

In some embodiments, the multi-specific binding protein is in an CrossmAb format which is an homodimeric constructs where Fab binding to antigen 2 is fused to the N terminus of HC of Fab that binds to antigen 1. The construct contains wild—

Heterodimeric Antibody Heavy Chains

Assembly of heterodimeric antibody heavy chains can be accomplished by expressing two different antibody heavy chain sequences in the same cell, which may lead to the assembly of homodimers of each antibody heavy chain as well as assembly of heterodimers. Preferential assembly of heterodimeric heavy chains within the multi-specific binding proteins described herein can be promoted by incorporating distinct pairs of amino acid substitutions into the first CH3 domain within the first heavy chain polypeptide and the second CH3 domain within the second heavy chain polypeptide that allow these two chains to selectively heterodimerize with each other, as shown in U.S. Ser. No. 13/494,870, U.S. Ser. No. 16/028,850, U.S. Ser. No. 11/533,709, U.S. Ser. No. 12/875,015, U.S. Ser. No. 13/289,934, U.S. Ser. No. 14/773,418, U.S. Ser. No. 12/811,207, U.S. Ser. No. 13/866,756, U.S. Ser. No. 14/647,480, U.S. Ser. No. 14/830,336. In some embodiments, the multi-specific binding proteins contain the Fc domain of human IgG1. Various examples of amino acid substitutions within the pair of human IgG1 Fc domains are listed below to facilitate heterodimerization of two heavy chains. Each positions of amino acid substitutions is numbered according to the EU index as in Kabat.

In one scenario, an amino acid substitution in the first polypeptide replaces the original amino acid with a larger amino acid, selected from arginine (R), phenylalanine (F), tyrosine (Y) or tryptophan (W), and at least one amino acid substitution in the second polypeptide replaces the original amino acid(s) with a smaller amino acid(s), chosen from alanine (A), serine (S), threonine (T), or valine (V), such that the larger amino acid substitution (a protuberance) fits into the surface of the smaller amino acid substitutions (a cavity). For example, one polypeptide can include a T366W substitution, and the other can include three substitutions including T366S, L368A, and Y407V.

Alternatively, amino acid substitutions could be selected from the following sets of substitutions shown in Table 2.

TABLE 2

| | First Polypeptide | Second Polypeptide |
|---|---|---|
| Set 1 | S364E/F405A | Y349K/T394F |
| Set 2 | S364H/D401K | Y349T/T411E |
| Set 3 | S364H/T394F | Y349T/F405A |
| Set 4 | S364E/T394F | Y349K/F405A |
| Set 5 | S364E/T411E | Y349K/D401K |
| Set 6 | S364D/T394F | Y349K/F405A |
| Set 7 | S364H/F405A | Y349T/T394F |
| Set 8 | S364K/E357Q | L368D/K370S |
| Set 9 | L368D/K370S | S364K |
| Set 10 | L368E/K370S | S364K |
| Set 11 | K360E/Q362E | D401K |
| Set 12 | L368D/K370S | S364K/E357L |
| Set 13 | K370S | S364K/E357Q |
| Set 14 | F405L | K409R |
| Set 15 | K409R | F405L |

Alternatively, amino acid substitutions could be selected from the following sets of substitutions shown in Table 3.

TABLE 3

| | First Polypeptide | Second Polypeptide |
|---|---|---|
| Set 1 | K409W | D399V/F405T |
| Set 2 | Y349S | E357W |
| Set 3 | K360E | Q347R |
| Set 4 | K360E/K409W | Q347R/D399V/F405T |
| Set 5 | Q347E/K360E/K409W | Q347R/D399V/F405T |
| Set 6 | Y349S/K409W | E357W/D399V/F405T |

Alternatively, amino acid substitutions could be selected from the following set of substitutions shown in Table 4.

TABLE 4

|  | First Polypeptide | Second Polypeptide |
| --- | --- | --- |
| Set 1 | T366K/L351K | L351D/L368E |
| Set 2 | T366K/L351K | L351D/Y349E |
| Set 3 | T366K/L351K | L351D/Y349D |
| Set 4 | T366K/L351K | L351D/Y349E/L368E |
| Set 5 | T366K/L351K | L351D/Y349D/L368E |
| Set 6 | E356K/D399K | K392D/K409D |

Alternatively, at least one amino acid substitution in each polypeptide chain could be selected from Table 5.

TABLE 5

| First Polypeptide | Second Polypeptide |
| --- | --- |
| L351Y, D399R, D399K, S400K, S400R, Y407A, Y407I, Y407V | T366V, T366I, T366L, T366M, N390D, N390E, K392L, K392M, K392V, K392F K392D, K392E, K409F, K409W, T411D and T411E |

Alternatively, at least one amino acid substitutions could be selected from the following set of substitutions in Table 6, where the position(s) indicated in the First Polypeptide column is replaced by any known negatively-charged amino acid, and the position(s) indicated in the Second Polypeptide Column is replaced by any known positively-charged amino acid.

TABLE 6

| First Polypeptide | Second Polypeptide |
| --- | --- |
| K392, K370, K409, or K439 | D399, E356, or E357 |

Alternatively, at least one amino acid substitutions could be selected from the following set of in Table 7, where the position(s) indicated in the First Polypeptide column is replaced by any known positively-charged amino acid, and the position(s) indicated in the Second Polypeptide Column is replaced by any known negatively-charged amino acid.

TABLE 7

| First Polypeptide | Second Polypeptide |
| --- | --- |
| D399, E356, or E357 | K409, K439, K370, or K392 |

Alternatively, amino acid substitutions could be selected from the following set of in Table 8.

TABLE 8

| First Polypeptide | Second Polypeptide |
| --- | --- |
| T350V, L351Y, F405A, and Y407V | T350V, T366L, K392L, and T394W |

Alternatively, or in addition, the structural stability of heterodimeric heavy chains within the multi-specific binding proteins can be increased by introducing S354C on either of the first or second polypeptide chain, and Y349C on the opposing polypeptide chain, which forms an artificial disulfide bridge within the interface of the two polypeptides.

The multi-specific binding proteins described above can be made using recombinant DNA technology well known to a skilled person in the art. For example, a first nucleic acid sequence encoding the first immunoglobulin heavy chain can be cloned into a first expression vector; a second nucleic acid sequence encoding the second immunoglobulin heavy chain can be cloned into a second expression vector; a third nucleic acid sequence encoding the first immunoglobulin light chain can be cloned into a third expression vector; a fourth nucleic acid sequence encoding the second immunoglobulin light chain can be cloned into a fourth expression vector; the first, second, third and fourth expression vectors can be stably transfected together into host cells to produce the multimeric proteins.

To achieve the highest yield of the multi-specific binding proteins, different ratios of the first, second, third and fourth expression vectors can be explored to determine the optimal ratio for transfection into the host cells. After transfection, single clones can be isolated for cell bank generation using methods known in the art, such as limited dilution, ELISA, FACS, microscopy, or Clonepix.

Clones can be cultured under conditions suitable for bio-reactor scale-up and maintained expression of the multi-specific protein. The multi-specific binding proteins can be isolated and purified using methods known in the art including centrifugation, depth filtration, cell lysis, homogenization, freeze-thawing, affinity purification, gel filtration, ion exchange chromatography, hydrophobic interaction exchange chromatography, and mixed-mode chromatography.

A Protein Comprising an Antigen-Binding Site that Competes with the NKG2D-Binding Sites Described Herein In certain embodiments, the present invention provides a protein that includes an antigen-binding site that competes with the NKG2D-binding sites described herein to bind to NKG2D. The NKG2D-binding sites described herein comprises amino acid sequences of SEQ ID NOs: 1 and 2; amino acid sequences of SEQ ID NOs: 3 and 4; amino acid sequences of SEQ ID NOs: 5 and 6; amino acid sequences of SEQ ID NOs: 7 and 8; amino acid sequences of SEQ ID NOs: 9 and 10; amino acid sequences of SEQ ID NOs: 83 and 8; amino acid sequences of SEQ ID NOs: 84 and 8; amino acid sequences of SEQ ID NOs: 85 and 8; amino acid sequences of SEQ ID NOs: 86 and 8; or amino acid sequences of SEQ ID NOs: 87 and 8. These NKG2D-binding sites can bind to different epitopes on NKG2D mapped by surface plasmon resonance. For example, ADI-27744 binds to a different epitope on NKG2D from ADI-27749 and other existing NKG2D antibodies, as shown in Example 2.

In some embodiments, an antigen-binding site of the protein that competes with the NKG2D-binding sites includes a heavy chain variable domain having an amino acid sequence at least 50% (e.g., 50%, 60%, 70%, 80%, 90%, 91%, 92%, 93%, 94%, 95%, 96%, 97%, 98%, 99%, or 100%) identical to the amino acid sequence of SEQ ID NO:1 and a light chain variable domain having an amino acid sequence at least at least 50% (e.g., 50%, 60%, 70%, 80%, 90%, 91%, 92%, 93%, 94%, 95%, 96%, 97%, 98%, 99%, or 100%) identical to the amino acid sequence of SEQ ID NO:2. In some embodiments, an antigen-binding site of the protein that competes with the NKG2D-binding sites includes a heavy chain variable domain having an amino acid sequence at least at least 50% (e.g., 50%, 60%, 70%, 80%, 90%, 91%, 92%, 93%, 94%, 95%, 96%, 97%, 98%, 99%, or 100%) identical to the amino acid sequence of SEQ ID NO:3 and a light chain variable domain having an amino acid sequence at least at least 50% (e.g., 50%, 60%, 70%, 80%, 90%, 91%, 92%, 93%, 94%, 95%, 96%, 97%, 98%, 99%, or 100%) identical to the amino acid sequence of SEQ ID NO:4. In some embodiments, an antigen-binding site of the protein that competes with the NKG2D-binding sites includes a heavy chain variable domain having an amino acid sequence at least at least 50% (e.g., 50%, 60%, 70%, 80%, 90%, 91%, 92%, 93%, 94%, 95%, 96%, 97%, 98%, 99%, or 100%) identical to the amino acid sequence of SEQ ID NO:5 and a light chain variable domain having an amino acid sequence at least at least 50% (e.g., 50%, 60%, 70%, 80%, 90%, 91%, 92%, 93%, 94%, 95%, 96%, 97%, 98%, 99%, or 100%) identical to the amino acid sequence of SEQ ID NO:6. In some embodiments, an antigen-binding site of the protein that competes with the NKG2D-binding sites includes a heavy chain variable domain having an amino acid sequence at least at least 50% (e.g., 50%, 60%, 70%, 80%, 90%, 91%, 92%, 93%, 94%, 95%, 96%, 97%, 98%, 99%, or 100%) identical to the amino acid sequence of SEQ ID NO:7 and a light chain variable domain having an amino acid sequence at least at least 50% (e.g., 50%, 60%, 70%, 80%, 90%, 91%, 92%, 93%, 94%, 95%, 96%, 97%, 98%, 99%, or 100%) identical to the amino acid sequence of SEQ ID NO:8. In some embodiments an antigen-binding site of the protein that competes with the NKG2D-binding sites includes a heavy chain variable domain having an amino acid sequence at least 50% (e.g., 50%, 60%, 70%, 80%, 90%, 91%, 92%, 93%, 94%, 95%, 96%, 97%, 98%, 99%, or 100%) identical to the amino acid sequence of SEQ ID NO:9 and a light chain variable domain having an amino acid sequence at least at least 50% (e.g., 50%, 60%, 70%, 80%, 90%, 91%, 92%, 93%, 94%, 95%, 96%, 97%, 98%, 99%, or 100%) identical to the amino acid sequence of SEQ ID NO:10.

In some embodiments, the protein that includes an antigen-binding site that competes with NKG2D-binding sites described herein further includes a second antigen-binding site that binds a tumor-associated antigen and/or a CD16 binding site. In some embodiments, the CD16 binding site is an antibody constant region or a portion thereof capable of binding CD16. In some embodiments, the CD16 binding site contains a human IgG1 Fc domain.

Cell for Expressing a Protein

In one aspect, the present disclosure provides a cell comprising one or more nucleic acids encoding a protein that contains: an NKG2D-binding site with a heavy chain variable domain having an amino acid sequence at least 90% (e.g., 91%, 92%, 93%, 94%, 95%, 96%, 97%, 98%, 99%, or 100%) identical to the amino acid sequence of SEQ ID NO:1, and a light chain variable domain having an amino acid sequence at least 90% (e.g., 91%, 92%, 93%, 94%, 95%, 96%, 97%, 98%, 99%, or 100%) identical to the amino acid sequence of SEQ ID NO:2; a NKG2D-binding site with a heavy chain variable domain having an amino acid sequence at least 90% (e.g., 91%, 92%, 93%, 94%, 95%, 96%, 97%, 98%, 99%, or 100%) identical to the amino acid sequence of SEQ ID NO:3, and a light chain variable domain having an amino acid sequence at least 90% (e.g., 91%, 92%, 93%, 94%, 95%, 96%, 97%, 98%, 99%, or 100%) identical to the amino acid sequence of SEQ ID NO:4; an NKG2D-binding site with a heavy chain variable domain having an amino acid sequence at least 90% (e.g., 91%, 92%, 93%, 94%, 95%, 96%, 97%, 98%, 99%, or 100%) identical to the amino acid sequence of SEQ ID NO:5, and a light chain variable domain having an amino acid sequence at least 90% (e.g., 91%, 92%, 93%, 94%, 95%, 96%, 97%, 98%, 99%, or 100%) identical to the amino acid sequence of SEQ ID NO:6; an NKG2D-binding site with a heavy chain variable domain having an amino acid sequence at least 90% (e.g., 91%, 92%, 93%, 94%, 95%, 96%, 97%, 98%, 99%, or 100%) identical to the amino acid sequence of SEQ ID NO:7, 83, 84, 85, 86, or 87, and a light chain variable domain having an amino acid sequence at least 90% (e.g., 91%, 92%, 93%, 94%, 95%, 96%, 97%, 98%, 99%, or 100%) identical to the amino acid sequence of SEQ ID NO:8; or an NKG2D-binding site with a heavy chain variable domain having an amino acid sequence at least 90% (e.g., 91%, 92%, 93%, 94%, 95%, 96%, 97%, 98%, 99%, or 100%) identical to the amino acid sequence of SEQ ID NO:9, and a light chain variable domain having an amino acid sequence at least 90% (e.g., 91%, 92%, 93%, 94%, 95%, 96%, 97%, 98%, 99%, or 100%) identical to the amino acid sequence of SEQ ID NO:10.

Therapeutic Applications

The invention provides methods for enhancing tumor cell death and/or treating cancer using a multi-specific binding protein described herein and/or a pharmaceutical composition described herein. The methods may be used to treat a variety of cancers. The type of cancer to be treated is desirably matched with the type of cancer cell to which the protein binds. Additional aspects and embodiments of the therapeutic methods are described below.

Pharmaceutical Compositions

In one aspect, the present disclosure also features pharmaceutical compositions that contain an effective amount of a protein, which contains an NKG2D-binding site described herein or an NKG2D-binding site that competes with the NKG2D-binding sites described herein, and a pharmaceutically acceptable carrier.

In certain embodiments, the formulation includes a protein that comprises an antigen-binding site with a heavy chain variable domain having an amino acid sequence at least 90% (e.g., 91%, 92%, 93%, 94%, 95%, 96%, 97%, 98%, 99%, or 100%) identical to the amino acid sequence of SEQ ID NO:1, and a light chain variable domain having an amino acid sequence at least 90% (e.g., 91%, 92%, 93%, 94%, 95%, 96%, 97%, 98%, 99%, or 100%) identical to the amino acid sequence of SEQ ID NO:2. In certain embodiments, the formulation includes a protein that includes an antigen-binding site with a heavy chain variable domain having an amino acid sequence at least 90% (e.g., 91%, 92%, 93%, 94%, 95%, 96%, 97%, 98%, 99%, or 100%) identical to the amino acid sequence of SEQ ID NO:3, and a light chain variable domain having an amino acid sequence at least 90% (e.g., 91%, 92%, 93%, 94%, 95%, 96%, 97%, 98%, 99%, or 100%) identical to the amino acid sequence of SEQ ID NO:4. In certain embodiments, the formulation includes a protein that includes an antigen-binding site with a heavy chain variable domain having an amino acid sequence at least 90% (e.g., 91%, 92%, 93%, 94%, 95%, 96%, 97%, 98%, 99%, or 100%) identical to the amino acid sequence of SEQ ID NO:5, and a light chain variable domain having an amino acid sequence at least 90% (e.g., 91%, 92%, 93%, 94%, 95%, 96%, 97%, 98%, 99%, or 100%) identical to the amino acid sequence of SEQ ID NO:6. In certain embodiments, the formulation includes a protein that includes an antigen-binding site with a heavy chain variable domain having an amino acid sequence at least 90% (e.g., 91%, 92%, 93%, 94%, 95%, 96%, 97%, 98%, 99%, or 100%) identical to the amino acid sequence of SEQ ID NO:7, 83, 84, 85, 86, or 87, and a light chain variable domain having an amino acid sequence at least 90% (e.g., 91%, 92%, 93%, 94%, 95%, 96%, 97%, 98%, 99%, or 100%) identical to the amino acid sequence of SEQ ID NO:8. In certain embodiments, the formulation includes a protein that includes an antigen-binding site with a heavy chain variable domain having an amino acid sequence at least 90% (e.g., 91%, 92%, 93%, 94%, 95%, 96%, 97%, 98%, 99%, or 100%) identical to the amino acid sequence of SEQ ID NO:9, and a light chain variable domain having an amino acid sequence at least 90% (e.g., 91%, 92%, 93%, 94%, 95%, 96%, 97%, 98%, 99%, or 100%) identical to the amino acid sequence of SEQ ID NO:10.

The composition can be formulated for use in a variety of drug delivery systems. One or more physiologically acceptable excipients or carriers can be included in the composition for proper formulation. Suitable formulations for use in the present disclosure are found in Remington's Pharmaceutical Sciences, Mack Publishing Company, Philadelphia, Pa., 17th ed., 1985. For a brief review of methods for drug delivery, see, e.g., Langer (Science 249:1527-1533, 1990).

For example, this present disclosure could exist in an aqueous pharmaceutical formulation including a therapeutically effective amount of the protein in a buffered solution forming a formulation. Aqueous carriers can include sterile water for injection (SWFI), bacteriostatic water for injection (BWFI), a pH buffered solution (e.g. phosphate-buffered saline), sterile saline solution, Ringer's solution or dextrose solution. In certain embodiments, an aqueous formulation is prepared including the protein disclosed herein in a pH-buffered solution. The pH of the preparations typically will be between 3 and 11, more preferably between 5 and 9 or between 6 and 8, and most preferably between 7 and 8, such as 7 to 7.5. Ranges intermediate to the above recited pH's are also intended to be part of this disclosure. For example, ranges of values using a combination of any of the above recited values as upper and/or lower limits are intended to be included. Examples of buffers that will control the pH within this range include acetate (e.g. sodium acetate), succinate (such as sodium succinate), gluconate, histidine, citrate and other organic acid buffers. In certain embodiments, the buffer system includes citric acid monohydrate, sodium citrate, disodium phosphate dihydrate, and/or sodium dihydrogen phosphate dihydrate. In certain embodiments, the buffer system includes about 1.3 mg/ml of citric acid (e.g., 1.305 mg/ml), about 0.3 mg/ml of sodium citrate (e.g., 0.305 mg/ml), about 1.5 mg/ml of disodium phosphate dihydrate (e.g. 1.53 mg/ml), about 0.9 mg/ml of sodium dihydrogen phosphate dihydrate (e.g., 0.86), and about 6.2 mg/ml of sodium chloride (e.g., 6.165 mg/ml). In certain embodiments, the buffer system includes 1-1.5 mg/ml of citric acid, 0.25 to 0.5 mg/ml of sodium citrate, 1.25 to 1.75 mg/ml of disodium phosphate dihydrate, 0.7 to 1.1 mg/ml of sodium dihydrogen phosphate dihydrate, and 6.0 to 6.4 mg/ml of sodium chloride. The pH of the liquid formulation may be set by addition of a pharmaceutically acceptable acid and/or base. In certain embodiments, the pharmaceutically acceptable acid may be hydrochloric acid. In certain embodiments, the base may be sodium hydroxide.

In some embodiments, the formulation includes an aqueous carrier, which is pharmaceutically acceptable (safe and non-toxic for administration to a human) and is useful for the preparation of a liquid formulation. Illustrative carriers include sterile water for injection (SWFI), bacteriostatic water for injection (BWFI), a pH buffered solution (e.g. phosphate-buffered saline), sterile saline solution, Ringer's solution or dextrose solution.

A polyol, which acts as a tonicifier and may stabilize the antibody, may also be included in the formulation. The polyol is added to the formulation in an amount which may vary with respect to the desired isotonicity of the formulation. In certain embodiments, the aqueous formulation may be isotonic. The amount of polyol added may also be altered with respect to the molecular weight of the polyol. For example, a lower amount of a monosaccharide (e.g. mannitol) may be added, compared to a disaccharide (such as trehalose). In certain embodiments, the polyol which may be used in the formulation as a tonicity agent is mannitol. In certain embodiments, the mannitol concentration may be about 5 to about 20 mg/ml. In certain embodiments, the concentration of mannitol may be about 7.5 to 15 mg/ml. In certain embodiments, the concentration of mannitol may be about 10-14 mg/ml. In certain embodiments, the concentration of mannitol may be about 12 mg/ml. In certain embodiments, the polyol sorbitol may be included in the formulation.

A detergent or surfactant may also be added to the formulation. Exemplary detergents include nonionic detergents such as polysorbates (e.g. polysorbates 20, 80 etc.) or poloxamers (e.g., poloxamer 188). The amount of detergent added is such that it reduces aggregation of the formulated antibody and/or minimizes the formation of particulates in the formulation and/or reduces adsorption. In certain embodiments, the formulation may include a surfactant which is a polysorbate. In certain embodiments, the formulation may contain the detergent polysorbate 80 or Tween 80. Tween 80 is a term used to describe polyoxyethylene (20) sorbitanmonooleate (see Fiedler, Lexikon der Hifsstoffe, Editio Cantor Verlag Aulendorf, 4th edi., 1996). In certain embodiments, the formulation may contain between about 0.1 mg/mL and about 10 mg/mL of polysorbate 80, or between about 0.5 mg/mL and about 5 mg/mL. In certain embodiments, about 0.1% polysorbate 80 may be added in the formulation.

In certain embodiments, the liquid formulation of the disclosure may be prepared as a 10 mg/mL concentration solution in combination with a sugar at stabilizing levels. In certain embodiments the liquid formulation may be prepared in an aqueous carrier. In certain embodiments, a stabilizer may be added in an amount no greater than that which may result in a viscosity undesirable or unsuitable for intravenous administration. In certain embodiments, the sugar may be disaccharides, e.g., sucrose. In certain embodiments, the liquid formulation may also include one or more of a buffering agent, a surfactant, and a preservative, which is added to the formulations herein to reduce bacterial action. The addition of a preservative may, for example, facilitate the production of a multi-use (multiple-dose) formulation.

In some embodiments, the present disclosure provides a formulation with an extended shelf life including the protein of the present disclosure, in combination with mannitol, citric acid monohydrate, sodium citrate, disodium phosphate dihydrate, sodium dihydrogen phosphate dihydrate, sodium chloride, polysorbate 80, water, and sodium hydroxide.

Deamidation is a common product variant of peptides and proteins that may occur during fermentation, harvest/cell clarification, purification, drug substance/drug product storage and during sample analysis. Deamidation is the loss of NH3 from a protein forming a succinimide intermediate that can undergo hydrolysis. The succinimide intermediate results in a mass decrease of 17 Da from the parent peptide. The subsequent hydrolysis results in an 18 u mass increase. Isolation of the succinimide intermediate is difficult due to instability under aqueous conditions. As such, deamidation is typically detectable as 1 u mass increase. Deamidation of an asparagine results in either aspartic or isoaspartic acid. The parameters affecting the rate of deamidation include pH, temperature, solvent dielectric constant, ionic strength, primary sequence, local polypeptide conformation and tertiary structure. The amino acid residues adjacent to Asn in the peptide chain affect deamidation rates. Gly and Ser following an Asn in protein sequences results in a higher susceptibility to deamidation. In certain embodiments, the liquid formulation of the present disclosure may be preserved under conditions of pH and humidity to prevent deamination of the protein product.

In some embodiment, the formulation is a lyophilized formulation. In certain embodiments, the formulation is freeze-dried (lyophilized) and contained in about 12-60 vials. In certain embodiments, the formulation is freeze-dried and 45 mg of the freeze-dried formulation may be contained in one vial. In certain embodiments, the about 40 mg-about 100 mg of freeze-dried formulation is contained in one vial. In certain embodiments, freeze dried formulation from 12, 27, or 45 vials are combined to obtained a therapeutic dose of the protein in the intravenous drug formulation. The formulation may be a liquid formulation. In some embodiments, a liquid formulation is stored as about 250 mg/vial to about 1000 mg/vial. In certain embodiments, the liquid formulation is stored as about 600 mg/vial. In certain embodiments, the liquid formulation is stored as about 250 mg/vial.

In some embodiments, the lyophilized formulation includes the proteins described herein and a lyoprotectant. The lyoprotectant may be sugar, e.g., disaccharides. In certain embodiments, the lycoprotectant may be sucrose or maltose. The lyophilized formulation may also include one or more of a buffering agent, a surfactant, a bulking agent, and/or a preservative. The amount of sucrose or maltose useful for stabilization of the lyophilized drug product may be in a weight ratio of at least 1:2 protein to sucrose or maltose. In certain embodiments, the protein to sucrose or maltose weight ratio may be of from 1:2 to 1:5.

In certain embodiments, the pH of the formulation, prior to lyophilization, may be set by addition of a pharmaceutically acceptable acid and/or base. In certain embodiments the pharmaceutically acceptable acid may be hydrochloric acid. In certain embodiments, the pharmaceutically acceptable base may be sodium hydroxide. Before lyophilization, the pH of the solution containing the protein of the present disclosure may be adjusted between 6 to 8. In certain embodiments, the pH range for the lyophilized drug product may be from 7 to 8.

In certain embodiments, a "bulking agent" may be added. A "bulking agent" is a compound which adds mass to a lyophilized mixture and contributes to the physical structure of the lyophilized cake (e.g., facilitates the production of an essentially uniform lyophilized cake which maintains an open pore structure). Illustrative bulking agents include mannitol, glycine, polyethylene glycol and sorbitol. The lyophilized formulations of the present invention may contain such bulking agents.

In certain embodiments, the lyophilized protein product is constituted with an aqueous carrier. The aqueous carrier of interest herein is one which is pharmaceutically acceptable (e.g., safe and non-toxic for administration to a human) and is useful for the preparation of a liquid formulation, after lyophilization. Illustrative diluents include sterile water for injection (SWFI), bacteriostatic water for injection (BWFI), a pH buffered solution (e.g. phosphate-buffered saline), sterile saline solution, Ringer's solution or dextrose solution. In certain embodiments, the lyophilized drug product of the current disclosure is reconstituted with either Sterile Water for Injection, USP (SWFI) or 0.9% Sodium Chloride Injection, USP. During reconstitution, the lyophilized powder dissolves into a solution. In certain embodiments, the lyophilized protein product of the instant disclosure is constituted to about 4.5 mL water for injection and diluted with 0.9% saline solution (sodium chloride solution).

The protein compositions may be sterilized by conventional sterilization techniques, or may be sterile filtered. The resulting aqueous solutions may be packaged for use as-is, or lyophilized, the lyophilized preparation being combined with a sterile aqueous carrier prior to administration. The resulting compositions in solid form may be packaged in multiple single dose units, each containing a fixed amount of the above-mentioned agent or agents. The composition in solid form can also be packaged in a container for a flexible quantity.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The specific dose can be a uniform dose for each patient, for example, 50-5000 mg of protein. Alternatively, a patient's dose can be tailored to the approximate body weight or surface area of the patient. Other factors in determining the appropriate dosage can include the disease or condition to be treated or prevented, the severity of the disease, the route of administration, and the age, sex and medical condition of the patient. Further refinement of the calculations necessary to determine the appropriate dosage for treatment is routinely made by those skilled in the art, especially in light of the dosage information and assays disclosed herein. The dosage can also be determined through the use of known assays for determining dosages used in conjunction with appropriate dose-response data. An individual patient's dosage can be adjusted as the progress of the disease is monitored. Blood levels of the targetable construct or complex in a patient can be measured to see if the dosage needs to be adjusted to reach or maintain an effective concentration. Pharmacogenomics may be used to determine which targetable constructs and/or complexes, and dosages thereof, are most likely to be effective for a given individual (Schmitz et al., Clinica Chimica Acta 308: 43-53, 2001; Steimer et al., Clinica Chimica Acta 308: 33-41, 2001).

In general, dosages based on body weight are from about 0.01 µg to about 100 mg per kg of body weight, such as about 0.01 µg to about 100 mg/kg of body weight, about 0.01 µg to about 50 mg/kg of body weight, about 0.01 g to about 10 mg/kg of body weight, about 0.01 g to about 1 mg/kg of body weight, about 0.01 µg to about 100 µg/kg of body weight, about 0.01 µg to about 50 µg/kg of body weight, about 0.01 g to about 10 µg/kg of body weight, about 0.01 µg to about 1 µg/kg of body weight, about 0.01 µg to about 0.1 µg/kg of body weight, about 0.1 µg to about 100 mg/kg of body weight, about 0.1 µg to about 50 mg/kg of body weight, about 0.1 µg to about 10 mg/kg of body weight, about 0.1 µg to about 1 mg/kg of body weight, about 0.1 µg to about 100 µg/kg of body weight, about 0.1 µg to about 10 µg/kg of body weight, about 0.1 µg to about 1 µg/kg of body weight, about 1 µg to about 100 mg/kg of body weight, about 1 µg to about 50 mg/kg of body weight, about 1 µg to about 10 mg/kg of body weight, about 1 µg to about 1 mg/kg of body weight, about 1 µg to about 100 µg/kg of body weight, about 1 µg to about 50 µg/kg of body weight, about 1 µg to about 10 µg/kg of body weight, about 10 µg to about 100 mg/kg of body weight, about 10 µg to about 50 mg/kg of body weight, about 10 µg to about 10 mg/kg of body weight, about 10 µg to about 1 mg/kg of body weight, about 10 µg to about 100 µg/kg of body weight, about 10 g to about 50 µg/kg of body weight, about 50 µg to about 100 mg/kg of body weight, about 50 µg to about 50 mg/kg of body weight, about 50 µg to about 10 mg/kg of body weight, about 50 µg to about 1 mg/kg of body weight, about 50 µg to about 100 µg/kg of body weight, about 100 µg to about 100 mg/kg of body weight, about 100 µg to about 50 mg/kg of body weight, about 100 µg to about 10 mg/kg of body weight, about 100 µg to about 1 mg/kg of body weight, about 1 mg to about 100 mg/kg of body weight, about 1 mg to about 50 mg/kg of body weight, about 1 mg to about 10 mg/kg of body weight, about 10 mg to about 100 mg/kg of body weight, about 10 mg to about 50 mg/kg of body weight, about 50 mg to about 100 mg/kg of body weight. Doses may be given once or more times daily, weekly, monthly or yearly, or even once every 2 to 20 years. Persons of ordinary skill in the art can easily estimate repetition rates for dosing based on measured residence times and concentrations of the targetable construct or complex in bodily fluids or tissues. Administration of the present invention could be intravenous, intraarterial, intraperitoneal, intramuscular, subcutaneous, intrapleural, intrathecal, intracavitary, by perfusion through a catheter or by direct intralesional injection. This may be administered once or more times daily, once or more times weekly, once or more times monthly, and once or more times annually.

Enhancing Tumor Cell Death and Cancer Treatment

The invention provides methods of enhancing tumor cell death and/or treating cancer in patient. In some embodiments, the method comprises exposing a tumor and natural killer cells to a multi-specific binding protein disclosed herein. In some embodiments, the method includes administering to a patient in need thereof a therapeutically effective amount of a protein and or its desired formulation described herein. In those embodiments, the multi-specific binding protein can contain: an antigen-binding site with a heavy chain variable domain having an amino acid sequence at least 90% (e.g., 91%, 92%, 93%, 94%, 95%, 96%, 97%, 98%, 99%, or 100%) identical to the amino acid sequence of SEQ ID NO:1, and a light chain variable domain having an amino acid sequence at least 90% (e.g., 91%, 92%, 93%, 94%, 95%, 96%, 97%, 98%, 99%, or 100%) identical to the amino acid sequence of SEQ ID NO:2; an antigen-binding site with a heavy chain variable domain having an amino acid sequence at least 90% (e.g., 91%, 92%, 93%, 94%, 95%, 96%, 97%, 98%, 99%, or 100%) identical to the amino acid sequence of SEQ ID NO:3 and a light chain variable domain having an amino acid sequence at least 90% (e.g., 91%, 92%, 93%, 94%, 95%, 96%, 97%, 98%, 99%, or 100%) identical to the amino acid sequence of SEQ ID NO:4; an antigen-binding site with a heavy chain variable domain having an amino acid sequence at least 90% (e.g., 91%, 92%, 93%, 94%, 95%, 96%, 97%, 98%, 99%, or 100%) identical to the amino acid sequence of SEQ ID NO:5 and a light chain variable domain having an amino acid sequence at least 90% (e.g., 91%, 92%, 93%, 94%, 95%, 96%, 97%, 98%, 99%, or 100%) identical to the amino acid sequence of SEQ ID NO:6; an antigen-binding site with a heavy chain variable domain having an amino acid sequence at least 90% (e.g., 91%, 92%, 93%, 94%, 95%, 96%, 97%, 98%, 99%, or 100%) identical to the amino acid sequence of SEQ ID NO:7, 83, 84, 85, 86, or 87 and a light chain variable domain having an amino acid sequence at least 90% (e.g., 91%, 92%, 93%, 94%, 95%, 96%, 97%, 98%, 99%, or 100%) identical to the amino acid sequence of SEQ ID NO:8; or an antigen-binding site with a heavy chain variable domain having an amino acid sequence at least 90% (e.g., 91%, 92%, 93%, 94%, 95%, 96%, 97%, 98%, 99%, or 100%) identical to the amino acid sequence of SEQ ID NO:9 and a light chain variable domain having an amino acid sequence at least 90% (e.g., 91%, 92%, 93%, 94%, 95%, 96%, 97%, 98%, 99%, or 100%) identical to the amino acid sequence of SEQ ID NO:10.

The type of cancer to be treated is desirably matched with the type of cancer cell to which the multi-specific binding protein disclosed herein binds. For example, treatment of a cancer expressing epithelial cell adhesion molecule (Ep-CAM), such as a colon cancer expressing EpCAM, is desirably treated using a multispecific-binding protein described herein that binds to EpCAM and NKG2D.

In some embodiment, patients to be treated contain cancer cells that expresses one or more of the following: CD33, HER2, CD2, CD19, CD20, CD30, CD38, CD40, CD52, CD70, EGFR/ERBB1, IGF1R, HER3/ERBB3, HER4/ERBB4, MUC1, CEA, cMET, SLAMF7, PSCA, MICA, MICB, TRAILR1, TRAILR2, MAGE-A3, B7.1, B7.2, CTLA4, and PD1. In some embodiments, the patients to be treated have a solid cancer, such as brain cancer, bladder cancer, breast cancer, cervical cancer, colon cancer, colorectal cancer, endometrial cancer, esophageal cancer, leukemia, lung cancer, liver cancer, melanoma, ovarian cancer, pancreatic cancer, prostate cancer, rectal cancer, renal cancer, stomach cancer, testicular cancer, or uterine cancer. In yet other embodiments, the cancer is a vascularized tumor, squamous cell carcinoma, adenocarcinoma, small cell carcinoma, melanoma, glioma, neuroblastoma, sarcoma (e.g., an angiosarcoma or chondrosarcoma), larynx cancer, parotid cancer, bilary tract cancer, thyroid cancer, acral lentiginous melanoma, actinic keratoses, acute lymphocytic leukemia, acute myeloid leukemia, adenoid cycstic carcinoma, adenomas, adenosarcoma, adenosquamous carcinoma, anal canal cancer, anal cancer, anorectum cancer, astrocytic tumor, bartholin gland carcinoma, basal cell carcinoma, biliary cancer, bone cancer, bone marrow cancer, bronchial cancer, bronchial gland carcinoma, carcinoid, cholangiocarcinoma, chondosarcoma, choriod plexus papilloma/carcinoma, chronic lymphocytic leukemia, chronic myeloid leukemia, clear cell carcinoma, connective tissue cancer, cystadenoma, digestive system cancer, duodenum cancer, endocrine system cancer, endodermal sinus tumor, endometrial hyperplasia, endometrial stromal sarcoma, endometrioid adenocarcinoma, endothelial cell cancer, ependymal cancer, epithelial cell cancer, Ewing's sarcoma, eye and orbit cancer, female genital cancer, focal nodular hyperplasia, gallbladder cancer, gastric antrum cancer, gastric fundus cancer, gastrinoma, glioblastoma, glucagonoma, heart cancer, hemangiblastomas, hemangioendothelioma, hemangiomas, hepatic adenoma, hepatic adenomatosis, hepatobiliary cancer, hepatocellular carcinoma, Hodgkin's disease, ileum cancer, insulinoma, intaepithelial neoplasia, interepithelial squamous cell neoplasia, intrahepatic bile duct cancer, invasive squamous cell carcinoma, jejunum cancer, joint cancer, Kaposi's sarcoma, pelvic cancer, large cell carcinoma, large intestine cancer, leiomyosarcoma, lentigo maligna melanomas, lymphoma, male genital cancer, malignant melanoma, malignant mesothelial tumors, medulloblastoma, medulloepithelioma, meningeal cancer, mesothelial cancer, metastatic carcinoma, mouth cancer, mucoepidermoid carcinoma, multiple myeloma, muscle cancer, nasal tract cancer, nervous system cancer, neuroepithelial adenocarcinoma nodular melanoma, non-epithelial skin cancer, non-Hodgkin's lymphoma, oat cell carcinoma, oligodendroglial cancer, oral cavity cancer, osteosarcoma, papillary serous adenocarcinoma, penile cancer, pharynx cancer, pituitary tumors, plasmacytoma, pseudosarcoma, pulmonary blastoma, rectal cancer, renal cell carcinoma, respiratory system cancer, retinoblastoma, rhabdomyosarcoma, sarcoma, serous carcinoma, sinus cancer, skin cancer, small cell carcinoma, small intestine cancer, smooth muscle cancer, soft tissue cancer, somatostatin-secreting tumor, spine cancer, squamous cell carcinoma, striated muscle cancer, submesothelial cancer, superficial spreading melanoma, T cell leukemia, tongue cancer, undifferentiated carcinoma, ureter cancer, urethra cancer, urinary bladder cancer, urinary system cancer, uterine cervix cancer, uterine corpus cancer, uveal melanoma, vaginal cancer, verrucous carcinoma, VIPoma, vulva cancer, well differentiated carcinoma, or Wilms tumor.

In some embodiments, the patients to be treated have non-Hodgkin's lymphoma, such as a B-cell lymphoma or a T-cell lymphoma. In certain embodiments, the non-Hodgkin's lymphoma is a B-cell lymphoma, such as a diffuse large B-cell lymphoma, primary mediastinal B-cell lymphoma, follicular lymphoma, small lymphocytic lymphoma, mantle cell lymphoma, marginal zone B-cell lymphoma, extranodal marginal zone B-cell lymphoma, nodal marginal zone B-cell lymphoma, splenic marginal zone B-cell lymphoma, Burkitt lymphoma, lymphoplasmacytic lymphoma, hairy cell leukemia, or primary central nervous system (CNS) lymphoma. In certain other embodiments, the non-Hodgkin's lymphoma is a T-cell lymphoma, such as a precursor T-lymphoblastic lymphoma, peripheral T-cell lymphoma, cutaneous T-cell lymphoma, angioimmunoblastic T-cell lymphoma, extranodal natural killer/T-cell lymphoma, enteropathy type T-cell lymphoma, subcutaneous panniculitis-like T-cell lymphoma, anaplastic large cell lymphoma, or peripheral T-cell lymphoma.

In some embodiments, proteins described herein are used in combination with additional therapeutic agents to treat patients with cancer. Exemplary therapeutic agents that may be used as part of a combination therapy in treating cancer, include, for example, radiation, mitomycin, tretinoin, ribomustin, gemcitabine, vincristine, etoposide, cladribine, mitobronitol, methotrexate, doxorubicin, carboquone, pentostatin, nitracrine, zinostatin, cetrorelix, letrozole, raltitrexed, daunorubicin, fadrozole, fotemustine, thymalfasin, sobuzoxane, nedaplatin, cytarabine, bicalutamide, vinorelbine, vesnarinone, aminoglutethimide, amsacrine, proglumide, elliptinium acetate, ketanserin, doxifluridine, etretinate, isotretinoin, streptozocin, nimustine, vindesine, flutamide, drogenil, butocin, carmofur, razoxane, sizofilan, carboplatin, mitolactol, tegafur, ifosfamide, prednimustine, picibanil, levamisole, teniposide, improsulfan, enocitabine, lisuride, oxymetholone, tamoxifen, progesterone, mepitiostane, epitiostanol, formestane, interferon-alpha, interferon-2 alpha, interferon-beta, interferon-gamma, colony stimulating factor-1, colony stimulating factor-2, denileukin diftitox, interleukin-2, luteinizing hormone releasing factor and variations of the aforementioned agents that may exhibit differential binding to its cognate receptor, and increased or decreased serum half-life.

An additional class of agents that may be used as part of a combination therapy in treating cancer is immune checkpoint inhibitors. Exemplary immune checkpoint inhibitors include agents that inhibit one or more of (i) cytotoxic T-lymphocyte-associated antigen 4 (CTLA4), (ii) programmed cell death protein 1 (PD1), (iii) PDL1, (iv) LAG3, (v) B7-H3, (vi) B7-H4, and (vii) TIM3. The CTLA4 inhibitor ipilimumab has been approved by the United States Food and Drug Administration for treating melanoma.

Yet other agents that may be used as part of a combination therapy in treating cancer are monoclonal antibody agents that target non-checkpoint targets (e.g., herceptin) and non-cytotoxic agents (e.g., tyrosine-kinase inhibitors).

Yet other categories of anti-cancer agents include, for example: (i) an inhibitor selected from an ALK Inhibitor, an ATR Inhibitor, an A2A Antagonist, a Base Excision Repair Inhibitor, a Bcr-Abl Tyrosine Kinase Inhibitor, a Bruton's Tyrosine Kinase Inhibitor, a $CDCl_7$ Inhibitor, a CHK1 Inhibitor, a Cyclin-Dependent Kinase Inhibitor, a DNA-PK Inhibitor, an Inhibitor of both DNA-PK and mTOR, a DNMT1 Inhibitor, a DNMT1 Inhibitor plus 2-chloro-deoxyadenosine, an HDAC Inhibitor, a Hedgehog Signaling Pathway Inhibitor, an IDO Inhibitor, a JAK Inhibitor, a mTOR Inhibitor, a MEK Inhibitor, a MELK Inhibitor, a MTH1 Inhibitor, a PARP Inhibitor, a Phosphoinositide 3-Kinase Inhibitor, an Inhibitor of both PARP1 and DHODH, a Proteasome Inhibitor, a Topoisomerase-II Inhibitor, a Tyrosine Kinase Inhibitor, a VEGFR Inhibitor, and a WEE1 Inhibitor; (ii) an agonist of OX40, CD137, CD40, GITR, CD27, HVEM, TNFRSF25, or ICOS; and (iii) a cytokine selected from IL-12, IL-15, GM-CSF, and G-CSF.

Proteins of the invention can also be used as an adjunct to surgical removal of the primary lesion.

The amount of protein and additional therapeutic agent and the relative timing of administration may be selected in order to achieve a desired combined therapeutic effect. For example, when administering a combination therapy to a patient in need of such administration, the therapeutic agents in the combination, or a pharmaceutical composition or compositions comprising the therapeutic agents, may be administered in any order such as, for example, sequentially, concurrently, together, simultaneously and the like. Further, for example, a protein described herein may be administered during a time when the additional therapeutic agent(s) exerts its prophylactic or therapeutic effect, or vice versa.

The description above describes multiple aspects and embodiments of the invention. The patent application specifically contemplates all combinations and permutations of the aspects and embodiments.

EXAMPLES

The invention now being generally described, will be more readily understood by reference to the following examples, which are included merely for purposes of illustration of certain aspects and embodiments of the present invention, and is not intended to limit the invention.

Example 1—Binding Affinities of Various NKG2D-Binding Domains

Kinetics and affinity of various NKG2D-binding domains were assessed by surface plasmon resonance using Biacore 8K instrument (GE Healthcare). Anti-human Fc antibody was immobilized on a CM5 chip using standard amine coupling chemistry. Human monoclonal antibodies containing various NKG2D-binding domains were captured on the anti-human Fc chip at a density of approximately 100 RU. Solutions containing 0.411-100 nM soluble mouse Fc-human NKG2D dimers were injected over the captured NKG2D antibodies and control surfaces at 30 μl/min at 37° C. Surfaces were regenerated between cycles by quick injection of 10 mM glycine, pH 1.8. To obtain kinetic rate constants, double-referenced data were fit to a 1:1 interaction model using Biacore 8K Evaluation software (GE Healthcare). The equilibrium binding constant $K_D$ was determined by the ratio of dissociation constant $k_d$ and association constant $k_a$ ($k_d/k_a$). As shown in Table 9 and FIG. 3, binding affinities of NKG2D-binding domains to NKG2D are in the range of 10-62 nM.

TABLE 9

| NKG2D-binding domain | $k_a$ (1/Ms) | $k_d$ (1/s) | $K_D$ (nM) |
|---|---|---|---|
| ADI-27744 (A44) | 2.95E+05 | 2.99E-03 | 10.1 |
| ADI-27749 (A49) | 3.95E+05 | 4.89E-03 | 12.4 |
| ADI-29378 (E78) | 8.32E+05 | 4.87E-02 | 58.5 |
| ADI-29379 (E79) | 4.43E+05 | 2.25E-02 | 50.7 |
| ADI-29463 (F63) | 1.64E+06 | 1.01E-01 | 61.8 |

Example 2—Binding Epitope Binning of ADI-27744 Clone

The binning of ADI-27744 (A44) NKG2D-binding domain was performed against a series of antibodies and ULBP6 (NKG2D natural ligand) by surface plasmon resonance using a Biacore 8K instrument. Briefly, mouse Fc-human NKG2D was captured using an anti-mouse Fc antibody immobilized on a CM5 chip at a density of approximately 100 RU. This was followed by consecutive injections of antibodies, including an NKG2D monoclonal antibody comprising ADI-27744, ADI-27749, F47 (sequences listed below) or 1D11 (a commercial monoclonal NKG2D antibody), ULBP6 (sequence listed below), MS (NKG2D antibody from Novo Nordisk, sequences listed below), and MAB139 (NKG2D antibody from R&D system, clone 149810) at 30 l/min at 25'C. Biacore 8K evaluation software was used for all data analysis.

TABLE 10

| Heavy chain variable region | Light chain variable region |
|---|---|
| F47 QVQLQQWGAGLLKPSETLSLTCAVY GGSFSGYYWSWIRQPPGKGLEWIGEI DHSGSTNYNPSLKSRVTISVDTSKNQ FSLKLSSVTAADTAVYYCARARGPW SFDPWGQGTLVTSS (SEQ ID NO: 51) CDR1 (SEQ ID NO: 52) - GSFSGYYWS CDR2 (SEQ ID NO: 53) - EIDHSGSTNYNPSLKS CDR3 (SEQ ID NO: 54) - ARARGPWSFDP | DIQMTQSPSTLSASVGDRVTITCRASQ SISSWLAWYQQKPGKAPKLLIYKASS LESGVPSRFSGSGSGTEFTLTISSLQPD DFATYYCQQYDTFITFGGGTKVEIK (SEQ ID NO: 55) CDR1 (SEQ ID NO: 56) - RASQSISSWLA CDR2 (SEQ ID NO: 57) - KASSLES CDR3 (SEQ ID NO: 58) - QQYDTFIT |
| MS QVHLQESGPGLVKPSETLSLTCTVSD DSISSYYWSWIRQPPGKGLEWIGHIS YSGSANYNPSLKSRVTISVDTSKNQF SLKLSSVTAADTAVYYCANWDDAF NIWGQGTMVTSS (SEQ ID NO: 59) CDR1 (SEQ ID NO: 60) - SYYWS CDR2 (SEQ ID NO: 61) - HISYSGSANYNPSLKS CDR3 (SEQ ID NO: 62) - WDDAFNI | EIVLTQSPGTLSLSPGERATLSCRASQ SVSSSYLAWYQQKPGQAPRLLIYGAS SRATGIPDRFSGSGSGTDFTLTISRLEP EDFAVYYCQQYGSSPWTFGGGTKVEI K (SEQ ID NO: 63) CDR1 (SEQ ID NO: 64) - RASQSVSSSYLA CDR2 (SEQ ID NO: 65) - GASSRAT CDR3 (SEQ ID NO: 66) - QQYGSSPWT |

```
ULBP amino acid sequence SEQ ID NO: 67:
RRDDPHSLCYDITVIPKFRPGPRWCAVQGQVDEKTFLHYDCGNKTVTPVS

PLGKKLNVTMAWKAQNPVLREVVDILTEQLLDIQLENYTPKEPLTLQARM

SCEQKAEGHSSGSWQFSIDGQTFLLFDSEKRMWTTVHPGARKMKEKWEND

KDVAMSFHYISMGDCIGWLEDFLMGMDSTLEPSAGAPLAMSSG
```

Figure 4A:
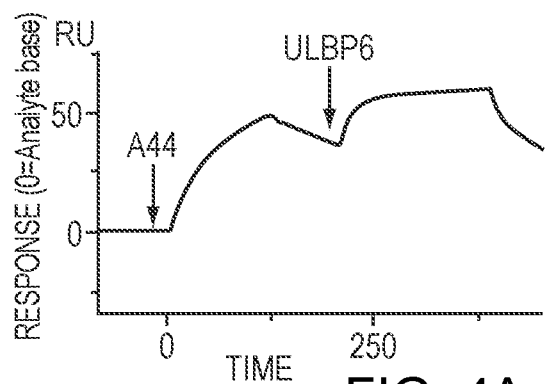
FIGS. 4A-H are profiles of competitive NKG2D binding by NKG2D-binding domain ADI-27744 (A44) and ULBP6 or other NKG2D antibodies measured by surface plasmon resonance.
Figure 4B:
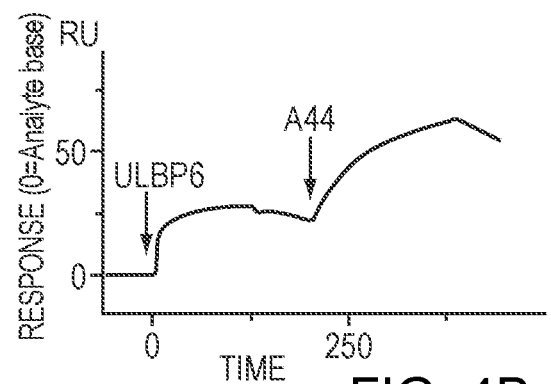

FIG. 4A shows the profile that an NKG2D monoclonal antibody comprising an ADI-27744 was injected over the immobilized NKG2D, followed by injection of ULBP6. FIG. 4B shows the profile of ULBP6 that was injected over an the immobilized NKG2D, followed by injection of NKG2D monoclonal antibody including AD-27744. These results show that NKG2D monoclonal antibody including an AD-27744 antigen-binding site does not block ULBP6 binding to NKG2D, i.e., ADI-27744 binds to an different epitope on NK(G2D from ULBP6.

Figure 4C:
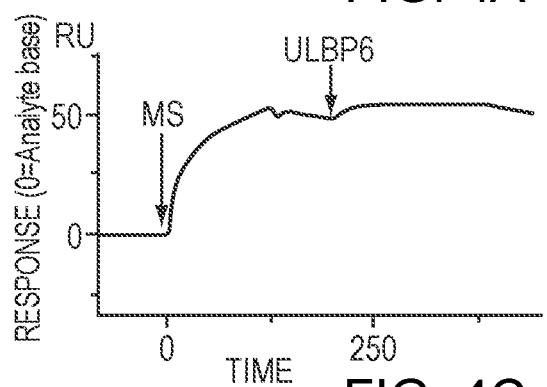
Figure 4D:
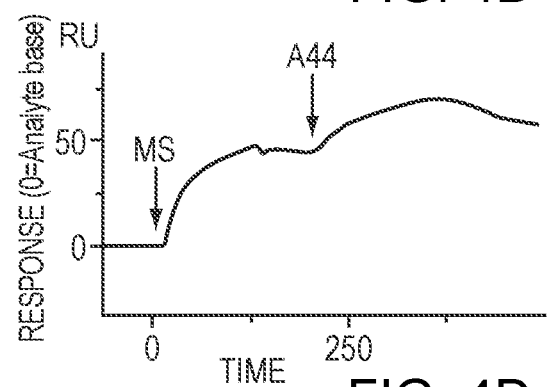
Figure 4E:
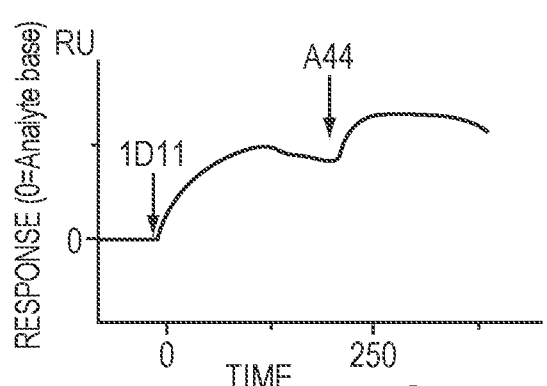
Figure 4F:
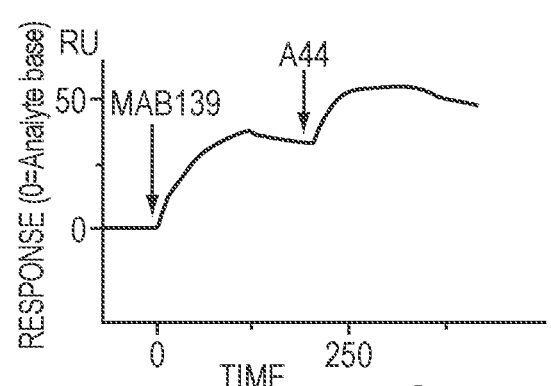
Figure 4G:
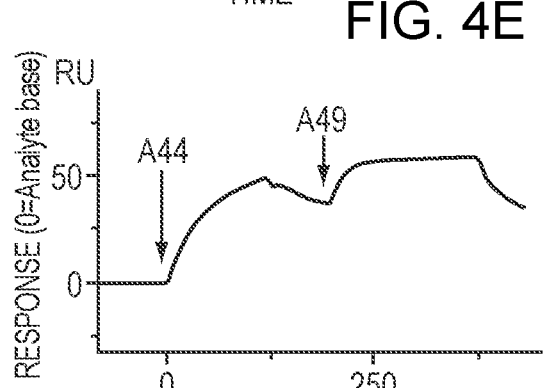
Figure 4H:
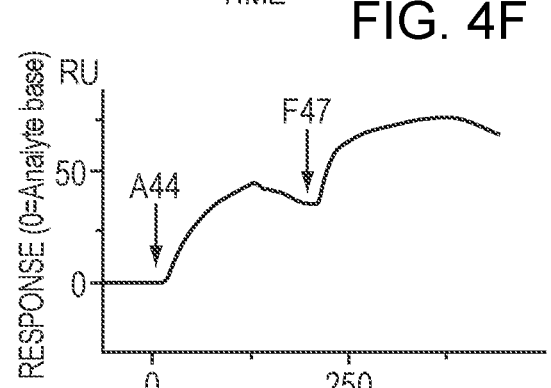

FIG. 4C shows the profile that MS monoclonal antibody was injected over the NKG2D, followed by injection of ULBP6. MS monoclonal antibody blocks ULBP6 from binding to NKG2D. FIGS. 4D-F shows the profile that MS, 1D11, or MAB139 was injected over the immobilized NKG2D, followed by injection of NKG2D monoclonal antibody comprising ADI-27744. FIGS. 4G-H shows the profile that NKG2D monoclonal antibody comprising ADI-27744 was injected over immobilized NKG2D, followed by injection of NKG2D monoclonal antibody comprising ADI-27749 or F47. ADI-27744 does not block the binding of MS, 1D11, and MAB139 to NKG2D. ADI-27749 and F47 do not block the binding of ADI-27744 to NKG2D. These results indicate that ADI-27744 binds to a unique epitope on NKG2D, different from the MS, 1D11, MAB139, ADI-27749 and F47 binding epitope(s).

Example 3—Trispecific Binding Proteins Bind to NKG2D

EL4 mouse lymphoma cell lines were engineered to express human NKG2D. Trispecific binding proteins (TriNKETs) that each contain an NKG2D-binding domain, a tumor-associated antigen-binding domain (such as a CD33 or a HER2-binding domain), and an Fc domain that binds to CD16 as shown in FIG. 1, were tested for their affinity to extracellular NKG2D expressed on EL4 cells. The binding of the multispecific binding proteins to NKG2D was detected using fluorophore-conjugated anti-human IgG secondary antibodies. Cells were analyzed by flow cytometry, and fold-over-background (FOB) was calculated using the mean fluorescence intensity (MFI) of NKG2D expressing cells compared to parental EL4 cells.

TriNKETs tested include CD33-TriNKET-A44 (ADI-27744 and a CD33 binding domain), CD33-TriNKET-A49 (ADI-27749 and a CD33 binding domain), CD33-TriNKET-F63 (ADI-29463 and a CD33 binding domain), HER2-TriNKET-A44 (ADI-27744 and a CD33 binding domain), HER2-TriNKET-A49 (ADI-27749 and a HER2 binding domain), HER2-TriNKET-F63 (ADI-29463 and a HER-binding domain), and HER2-TriNKET-E79 (ADI-29379 and a HER2 binding domain). The HER2-binding domain is composed of a heavy chain variable domain and a light chain variable domain of Trastuzumab. The CD33 binding domain is composed of a heavy chain variable domain and a light chain variable domain listed below.

```
                                           SEQ ID NO: 49
QVQLVQSGAEVKKPGASVKVSCKASGYTFTDYVVHWVRQAPGQGLEWMG
                          CDR1

YINPYNDGTKYNEKFKGRVTMTRDTSISTAYMELSRLRSDDTAVYYCAR
      CDR2

DYRYEVYGMDYWGQGTLVTVSS
      CDR3

SEQ ID NO: 50
DIVLTQSPASLAVSPGQRATITCTASSSVNYIHWYQQKPGQPPKLLIYD
                         CDR1

TSKVASGVPARFSGSGSGTDFTLTINPVEANDTANYYCQQWRSYPLTFG
CDR1                                          CDR3

QGTKLEIK
```

Figure 5:
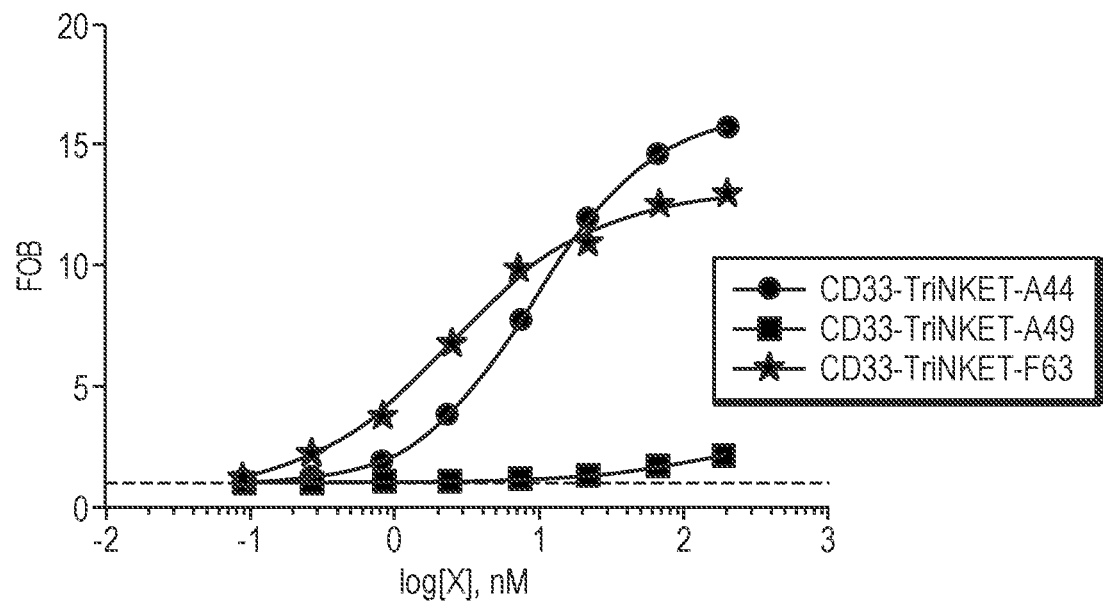
FIG. 5 are line graphs showing the binding profile of CD33-targeting TriNKETs to NKG2D expressed on EL4 cells.
Figure 6:
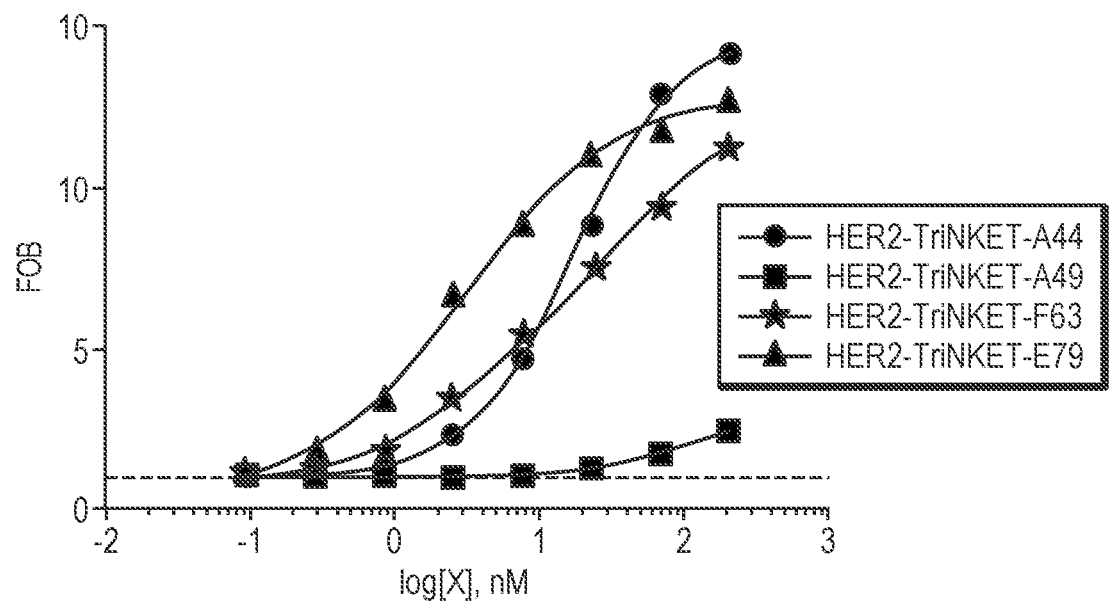
FIG. 6 are line graphs showing the binding profile of HER2-targeting TriNKETs to NKG2D expressed on EL4 cells.

All TriNKETs bind NKG2D on EL4 cells, but with different affinities. CD33-TriNKET-A44 show the same binding profile as HER2-TriNKET-A44, so do CD33-TriNKET-A49 as HER2-TriNKET-A49, and CD33-TriNKET-F63 to HER2-TriNKET-F63. The NKG2D-binding affinity for each clone was similar between cells expressing human and mouse NKG2D (FIGS. 5-6).

Example 4—Trispecific Binding Proteins Bind to Human Tumor Antigens

Trispecific Binding Proteins Bind to CD33

Human AML cell line MV4-11, expressing CD33 was used to assay the binding of TriNKETs to the tumor-associated antigen. TriNKETs and the parental CD33 monoclonal antibody were incubated with the cells, and the binding was detected using fluorophore-conjugated anti-human IgG secondary antibodies. Cells were analyzed by flow cytometry, and fold-over-background (FOB) was calculated using the mean fluorescence intensity (MFI) from TriNKETs and the parental monoclonal CD33 antibody normalized to secondary antibody controls.

Figure 7:
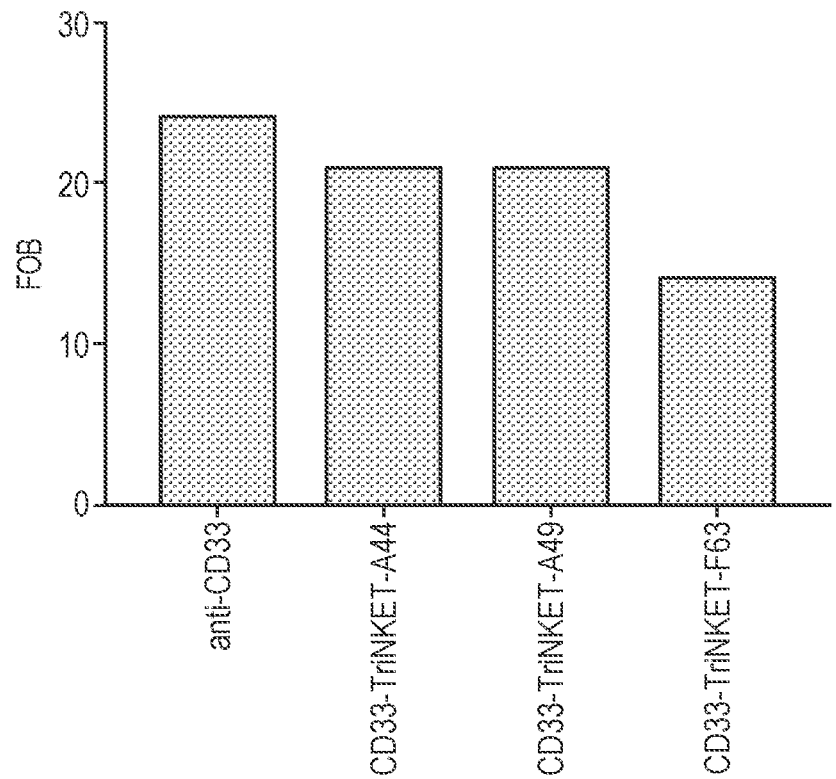
FIG. 7 are bar graphs showing the binding profile of CD33-targeting TriNKETs to CD33 expressed on Mv4-11 cells.

CD33-TriNKET-A44, CD33-TriNKET-A49, and CD33-TriNKET-F63 show comparable levels of binding to CD33 as compared with the parental CD33 antibody (FIG. 7).

Trispecific Binding Proteins Bind to HER2

Human cancer cell lines expressing HER2 were used to assay the binding of TriNKETs to the tumor-associated antigen. Renal cell carcinoma cell line 786-O expresses low level of HER2, and human lung cancer cell line NCI-H661 expresses moderate levels of HER2. TriNKETs and optionally the parental HER2 monoclonal antibody (Trastuzumab) were incubated with the cells, and the binding was detected using fluorophore-conjugated anti-human IgG secondary antibodies. Cells were analyzed by flow cytometry, and fold-over-background (FOB) was calculated using the mean fluorescence intensity (MFI) from TriNKETs and Trastuzumab normalized to secondary antibody controls.

Figure 8:
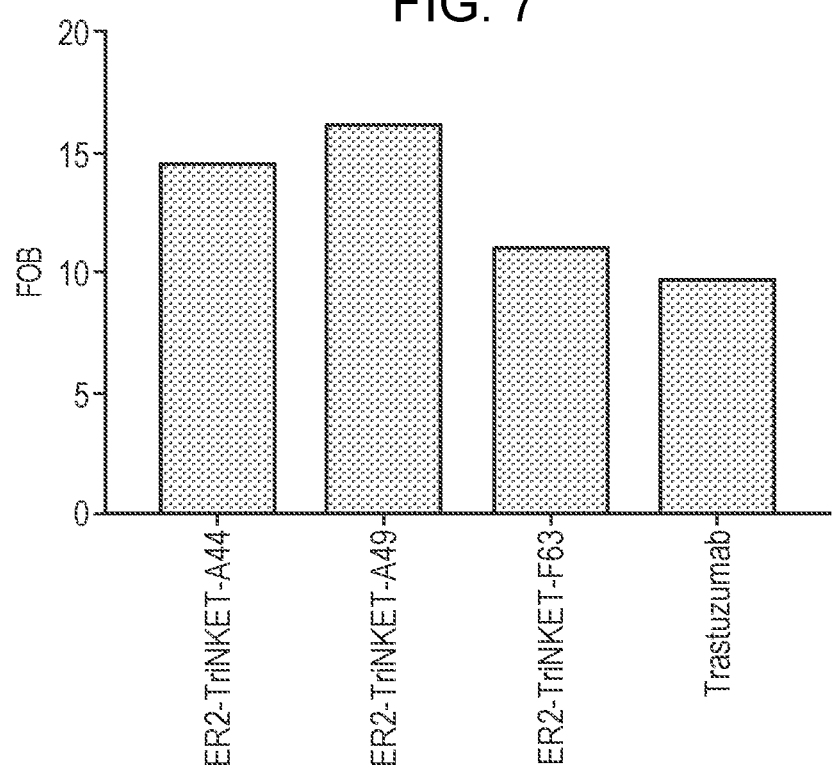
FIG. 8 are bar graphs showing the binding profile of HER2-targeting TriNKETs to HER2 expressed on 786-O cells.
Figure 9:
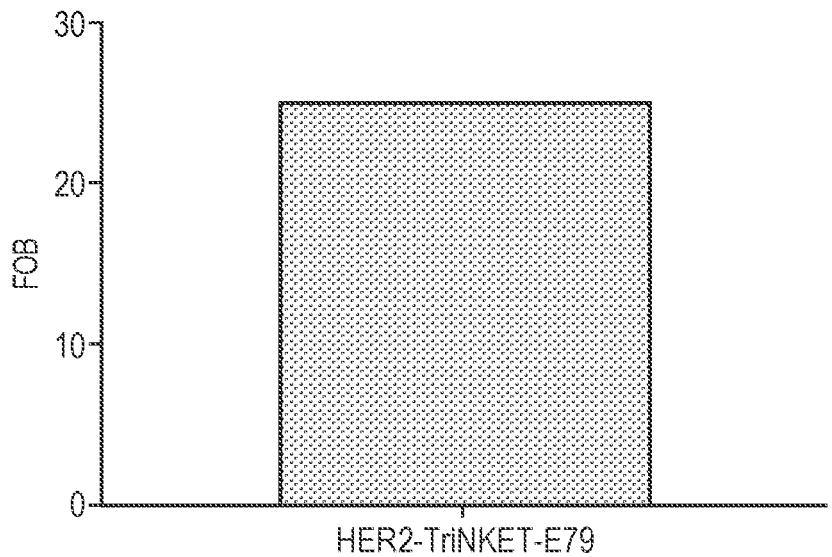
FIG. 9 are bar graphs showing the binding profile of a HER2-targeting TriNKETs to HER2 expressed on NCI-H661 cells.

HER2-TriNKET-A44, HER2-TriNKET-A49, and HER2-TriNKET-F63 show comparable levels of binding to HER2 expressed on 786-O cells as compared with Trastuzumab (FIG. 8). Binding to HER2 expressed on NCI-H661 cells by HER2-TriNKET-E79 is shown (FIG. 9).

Example 5—Trispecific Binding Proteins Activate NK Cells

Peripheral blood mononuclear cells (PBMCs) were isolated from human peripheral blood buffy coats using density gradient centrifugation. NK cells (CD3$^-$ CD56$^+$) were isolated using negative selection with magnetic beads from PBMCs, and the purity of the isolated NK cells was typically >90%. Isolated NK cells were cultured in media containing 100 ng/mL IL-2 for activation or rested overnight without cytokine. IL-2-activated NK cells were used within 24-48 hours after activation.

Human cancer cells expressing a tumor antigen were harvested and resuspended in culture media at $2 \times 10^6$ cells/mL. Monoclonal antibodies or TriNKETs targeting the tumor antigen were diluted in culture media. Activated NK cells were harvested, washed, and resuspended at $2 \times 10^6$ cells/mL in culture media. Cancer cells were then mixed with monoclonal antibodies/TriNKETs and activated NK cells in the presence of IL-2. Brefeldin-A and monensin were also added to the mixed culture to block protein transport out of the cell for intracellular cytokine staining. Fluorophore-conjugated anti-CD107a was added to the mixed culture and the culture was incubated for 4 hrs before samples were prepared for FACS analysis using fluorophore-conjugated antibodies against CD3, CD56 and IFN-gamma. CD107a and IFN-gamma staining was analyzed in CD3$^-$ CD56$^+$ cells to assess NK cell activation. The increase in CD107a/IFN-gamma double-positive cells is indicative of better NK cell activation through engagement of two activating receptors rather than one receptor.

Figure 10:
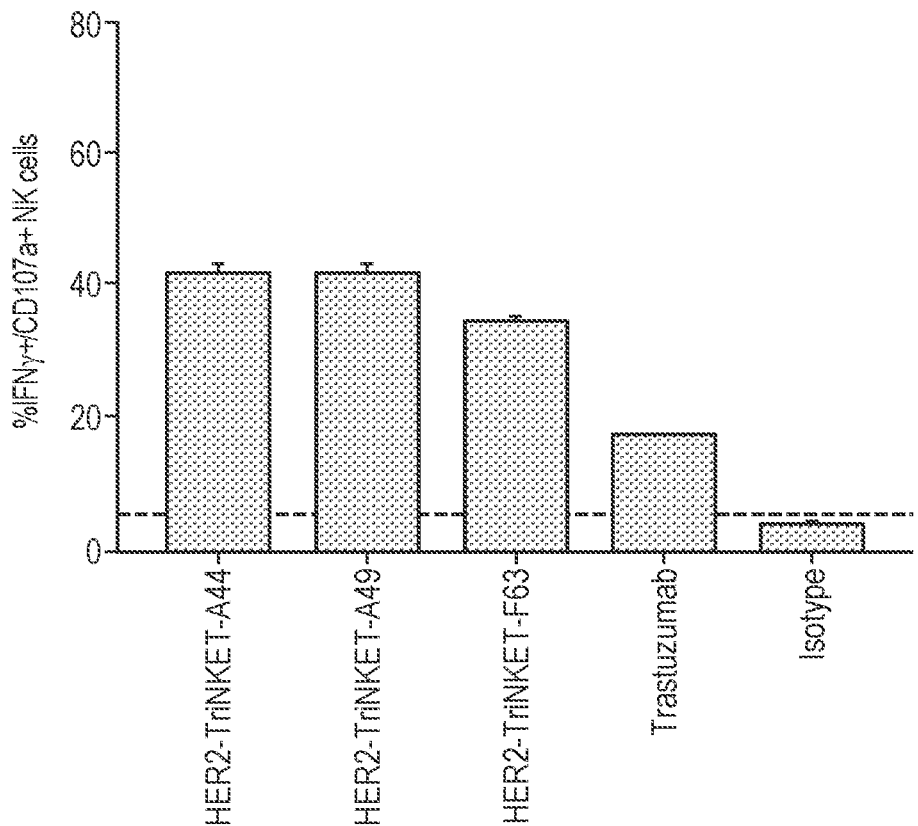
FIG. 10 are bar graphs showing that HER2-targeting TriNKETs mediate activation of human NK cells co-cultured with HER2-expressing NCI-H661 cells.
Figure 11:
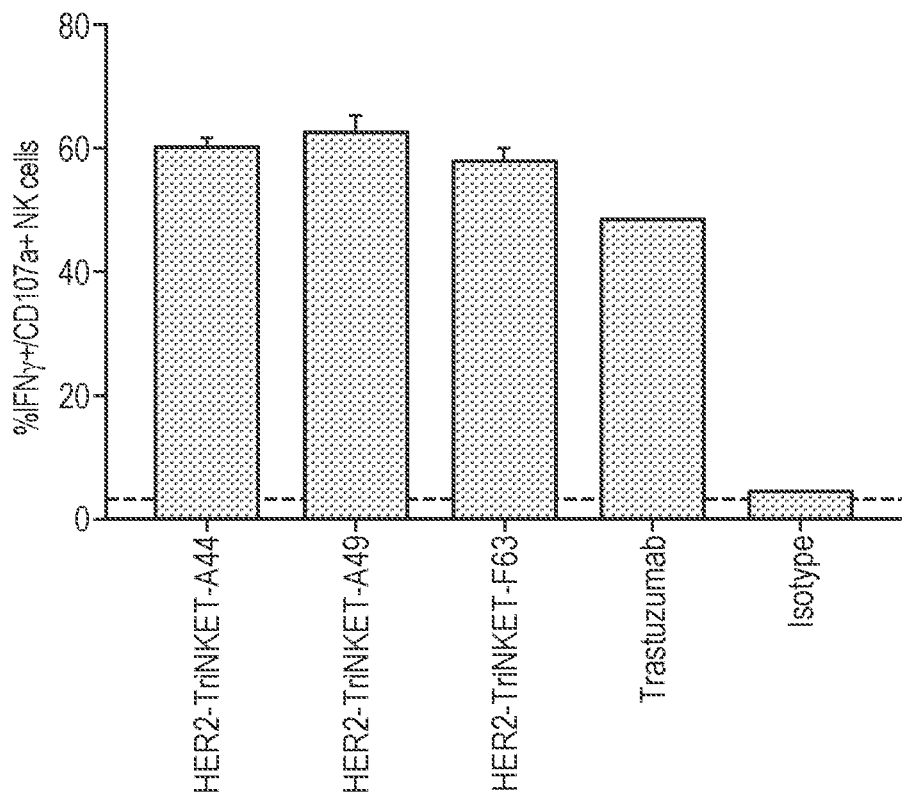
FIG. 11 are bar graphs showing that HER2-targeting TriNKETs mediate activation of human NK cells co-cultured with HER2 expressing SkBr-3 cells.

TriNKETs mediate activation of human NK cells co-cultured with HER2-expressing NCI-H661 cells (FIG. 10) and SkBr-3 cells (FIG. 11) respectively as indicated by an increase of CD107a degranulation and IFN-gamma production. Compared to the monoclonal antibody Trastuzumab, TriNKETs show superior activation of human NK cells in the presence of human cancer cells.

Figure 12:
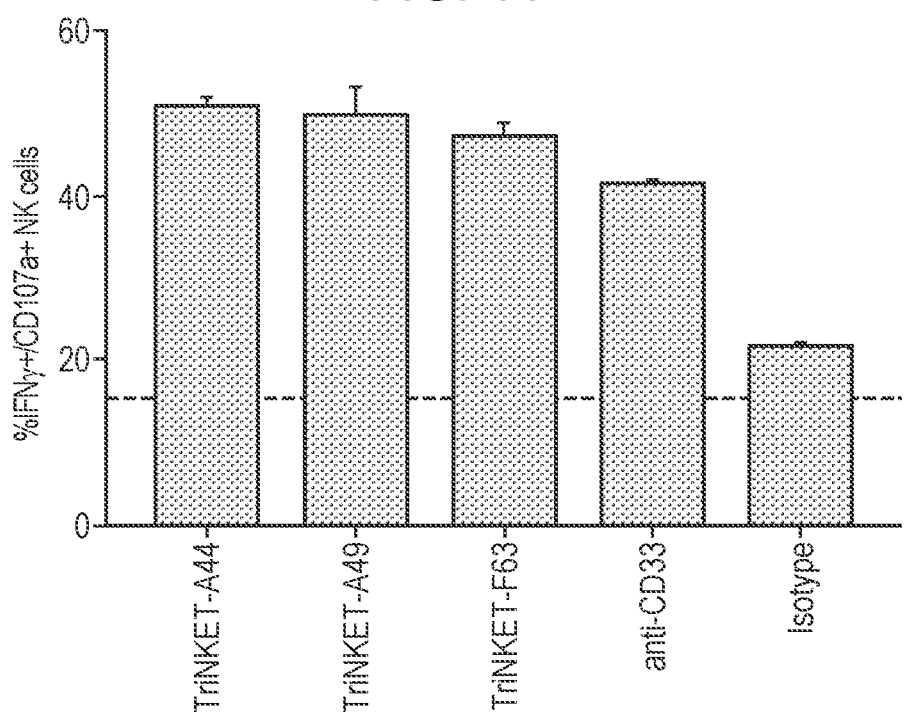
FIG. 12 are bar graphs showing that CD33-targeting TriNKETs mediate activation of human NK cells co-cultured with CD33-expressing human AML Mv4-11 cells.

TriNKETs mediate activation of human NK cells co-cultured with CD33-expressing human AML Mv4-11 cells as shown by an increase of CD107a degranulation and IFN-gamma production (FIG. 12). Compared to the monoclonal anti-CD33 antibody, TriNKETs show superior activation of human NK cells in the presence of human cancer cells.

Example 6—Trispecific Binding Proteins Enable Cytotoxicity of Target Cancer Cells Peripheral blood mononuclear cells (PBMCs) were isolated from human peripheral blood buffy coats using density gradient centrifugation. NK cells (CD3$^-$ CD56$^+$) were isolated using negative selection with magnetic beads from PBMCs, and the purity of the isolated NK cells was typically >90%. Isolated NK cells were cultured in media containing 100 ng/mL TL-2 for activation or rested overnight without cytokine. IL-2-activated or rested NK cells were used the following day in cytotoxicity assays.

In order to test the ability of human NK cells to lyse cancer cells in the presence of TriNKETs, a cytoTox 96 non-radioactive cytotoxicity assay from Promega (G1780) was used according to manufacturer's instruction. Briefly, human cancer cells expressing a tumor antigen were harvested, washed, and resuspended in culture media at 1-2×

10⁵ cells/mL. Rested and/or activated NK cells were harvested, washed, and resuspended at $10^5$-$2.0\times10^6$ cells/mL in the same culture media as that of the cancer cells. In each well of a 96 well plate, 50 µl of the cancer cell suspension was mixed with 50 µl of NK cell suspension with or without TriNKETs targeting the tumor antigen expressed on the cancer cells. After incubation at 37° C. with 5% $CO_2$ for 3 hours and 15 minutes, 10× lysis buffer was added to wells containing only cancer cells, and to wells containing only media for the maximum lysis and negative reagent control respectively. The plate was then placed back into the incubator for an additional 45 minutes to reach a total of 4 hours incubation. Cells were then pelleted, and the culture supernatant was transferred to a new 96 well plate and mixed with a substrate for development. The new plate was incubated for 30 minutes at room temperature, and the absorbance was read at 492 nm on a SpectraMax i3x. Percentage of specific lysis of the cancer cells was calculated as follows: % Specific lysis=((experimental lysis−spontaneous lysis from NK cells alone−spontaneous lysis from cancer cells alone)/ (Maximum lysis −negative reagent control))*100%

Figure 13:
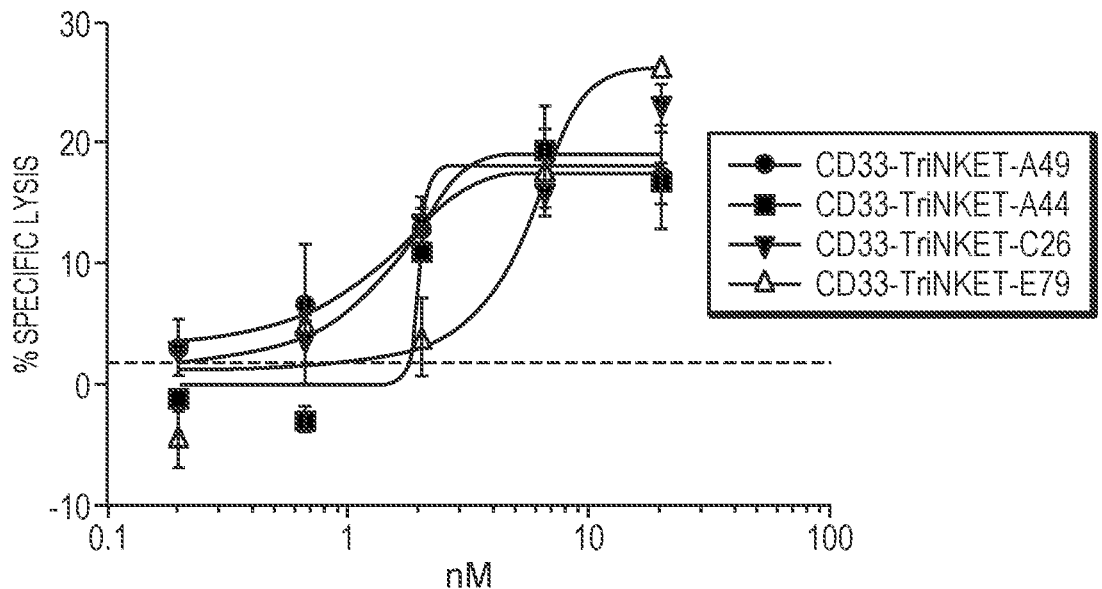
FIG. 13 are line graphs showing that CD33-targeting TriNKETs enable cytotoxicity of rested NK cells against CD33-expressing Molm-13 cancer cells.
Figure 14:
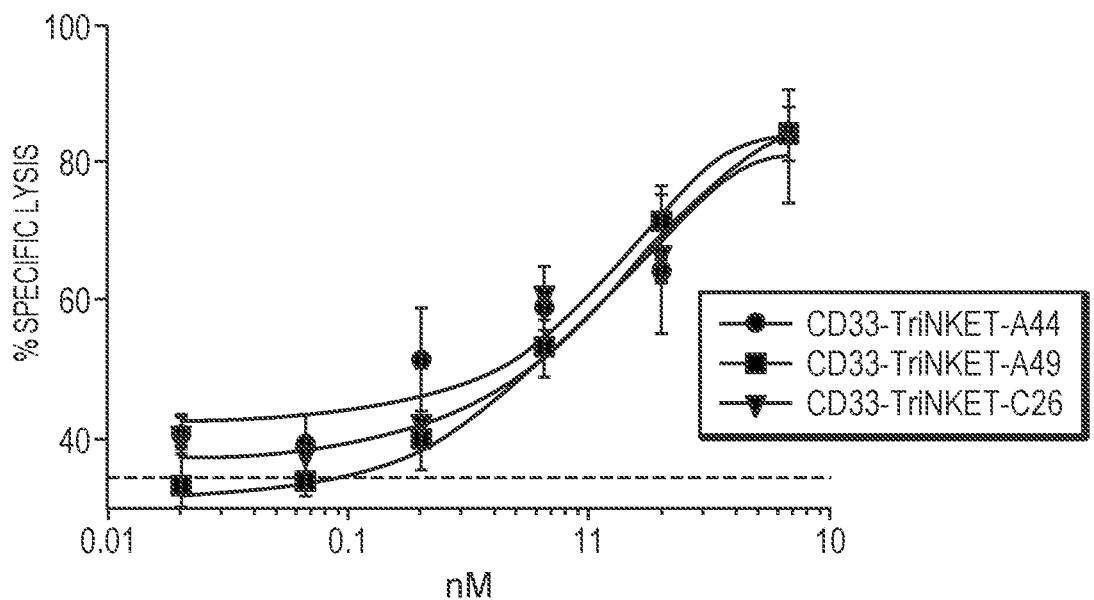
FIG. 14 are line graphs showing that CD33-targeting TriNKETs enable cytotoxicity of activated NK cells against CD33-expressing Molm-13 cancer cells.

TriNKETs mediate cytotoxicity of human NK cells against the CD33-positive Molm-13 human AML cell line. As shown in FIG. 13, rested human NK cells were mixed with Molm-13 cancer cells, and TriNKETs are able to enhance the cytotoxic activity of rested human NK cells in a dose-responsive manor against the cancer cells. The dotted line indicates cytotoxic activity of rested NK cells without TriNKETs. As shown in FIG. 14, activated human NK cells were mixed with Molm-13 cancer cells, and TriNKETs enhance the cytotoxic activity of activated human NK cells even further in a dose-responsive manor against the cancer cells.

Figure 15:
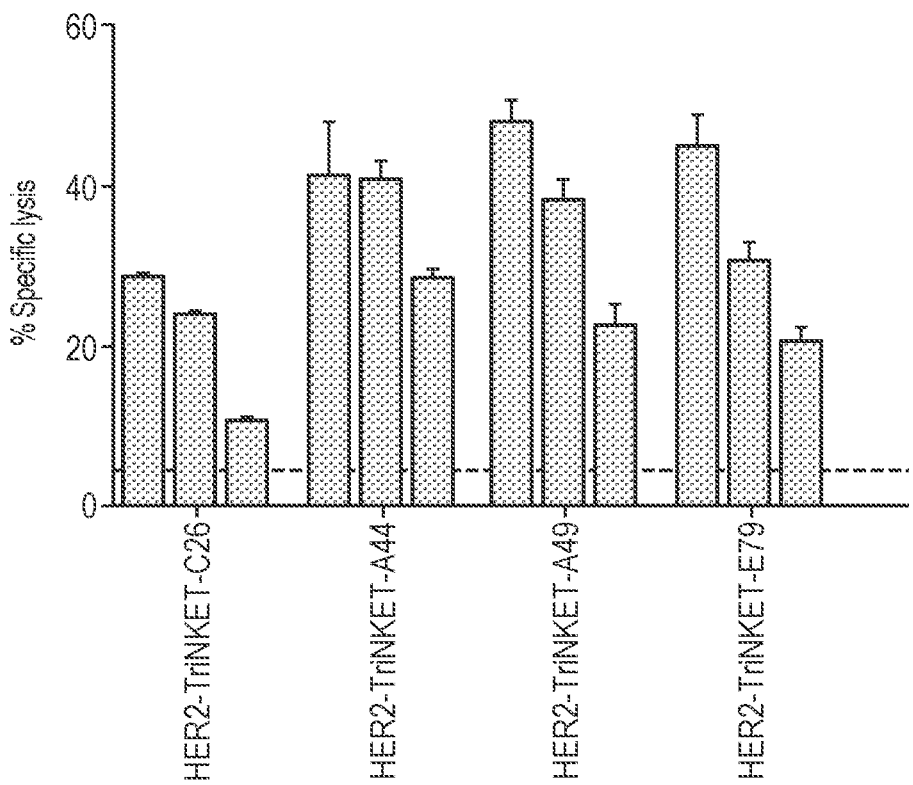
FIG. 15 are bar graphs showing that HER2-targeting TriNKETs enable cytotoxicity of rested NK cells against HER2-expressing 786-O cancer cells.
Figure 16:
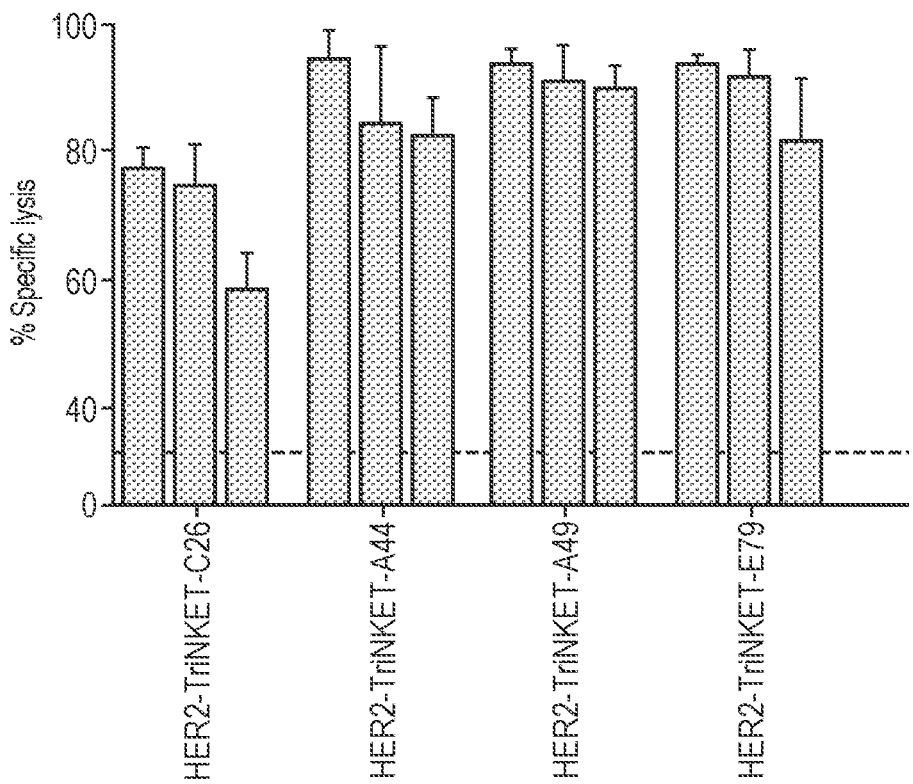
FIG. 16 are bar graphs showing that HER2-targeting TriNKETs enable cytotoxicity of activated NK cells against HER2-expressing 786-O cancer cells.
Figure 17:
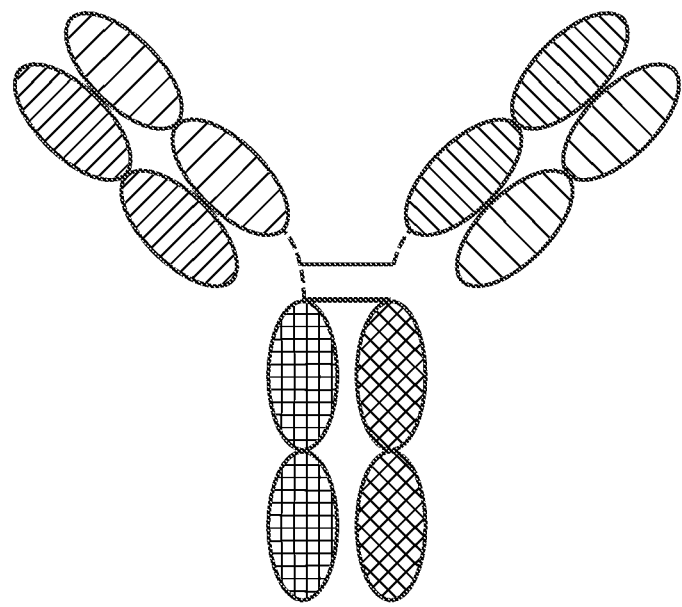
FIG. 17 is a representation of a TriNKET in the Triomab form, which is a trifunctional, bispecific antibody that maintains an IgG-like shape. This chimera consists of two half antibodies, each with one light and one heavy chain, that originate from two parental antibodies. Triomab form is an heterodimeric construct containing ½ of rat antibody and ½ of mouse antibody.
Figure 18:
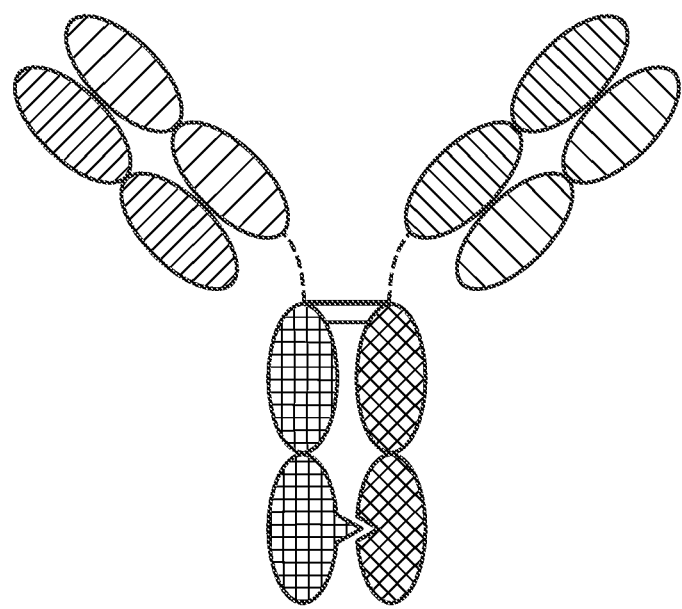
FIG. 18 is a representation of a TriNKET in the KiH Common Light Chain (LC) form, which involves the knobs-into-holes (KIHs) technology. KiH is a heterodimer containing 2 Fabs binding to target 1 and 2, and an Fc stabilized by heterodimerization mutations. TriNKET in the KiH format may be an heterodimeric construct with 2 fabs binding to target 1 and target 2, containing 2 different heavy chains and a common light chain that pairs with both HC.
Figure 19:
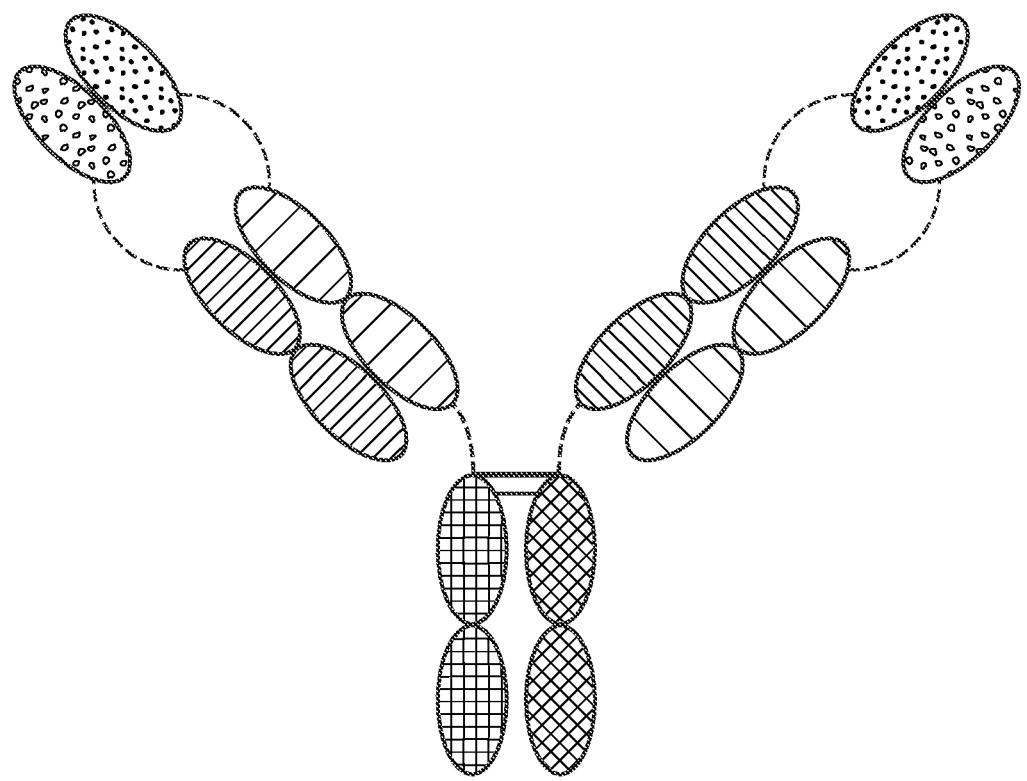
FIG. 19 is a representation of a TriNKET in the dual-variable domain immunoglobulin (DVD-Ig™) form, which combines the target binding domains of two monoclonal antibodies via flexible naturally occurring linkers, and yields a tetravalent IgG-like molecule. DVD-Ig™ is an homodimeric construct where variable domain targeting antigen 2 is fused to the N terminus of variable domain of Fab targeting antigen 1 Construct contains normal Fc.
Figure 20:
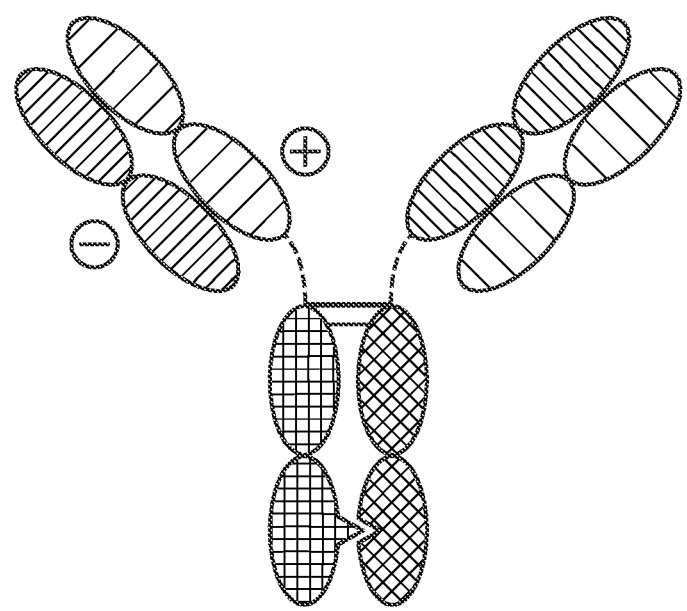
FIG. 20 is a representation of a TriNKET in the Orthogonal Fab interface (Ortho-Fab) form, which is an heterodimeric construct that contains 2 Fabs binding to target1 and target2 fused to Fc. LC-HC pairing is ensured by orthogonal interface. Heterodimerization is ensured by mutations in the Fc.
Figure 21:
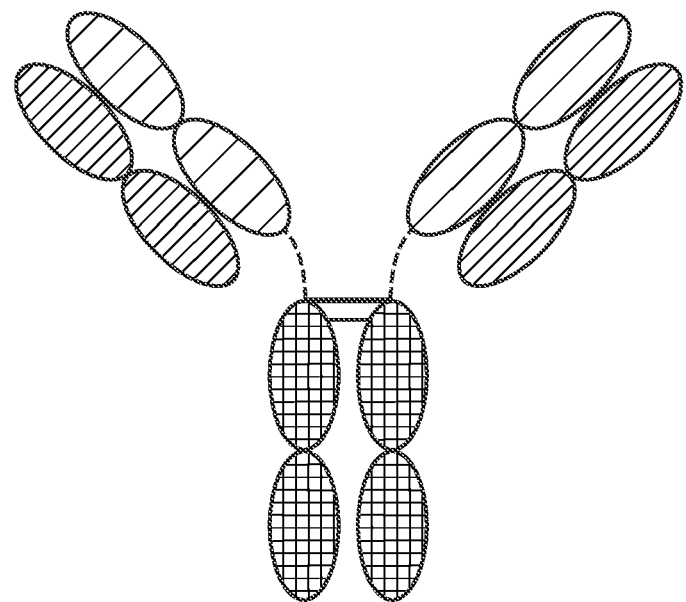
FIG. 21 is a representation of a TrinKET in the 2-in-1 Ig format.
Figure 22:
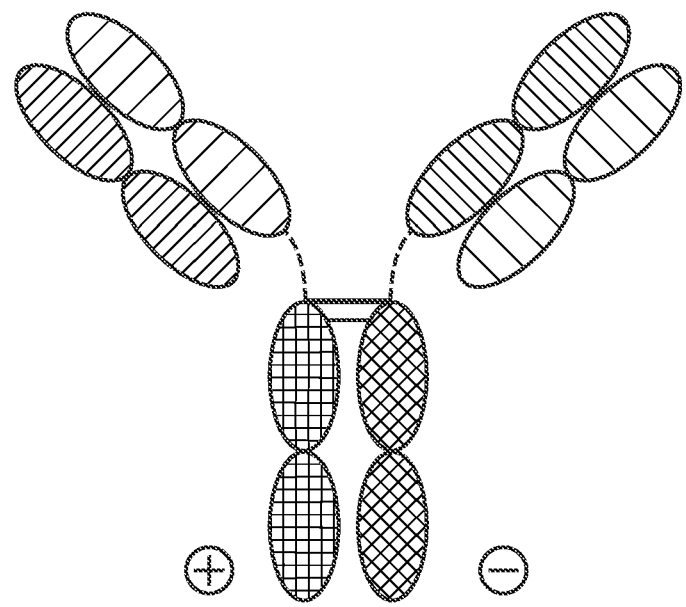
FIG. 22 is a representation of a TriNKET in the ES form, which is an heterodimeric construct containing 2 different Fabs binding to target 1 and target 2 fused to the Fc. Heterodimerization is ensured by electrostatic steering mutations in the Fc.
Figure 23:
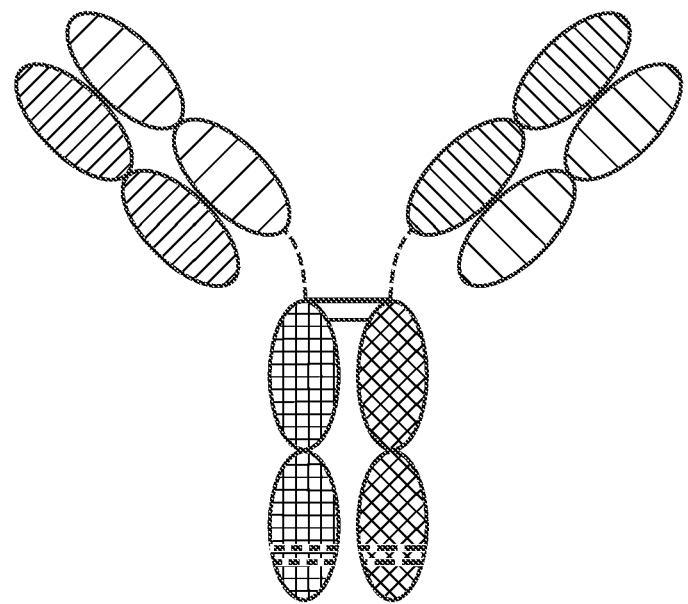
FIG. 23 is a representation of a TriNKET in the Fab Arm Exchange form: antibodies that exchange Fab arms by swapping a heavy chain and attached light chain (half-molecule) with a heavy-light chain pair from another molecule, resulting in bispecific antibodies. Fab Arm Exchange form (cFae) is a heterodimer containing 2 Fabs binding to target 1 and 2, and an Fc stabilized by heterodimerization mutations.
Figure 24:
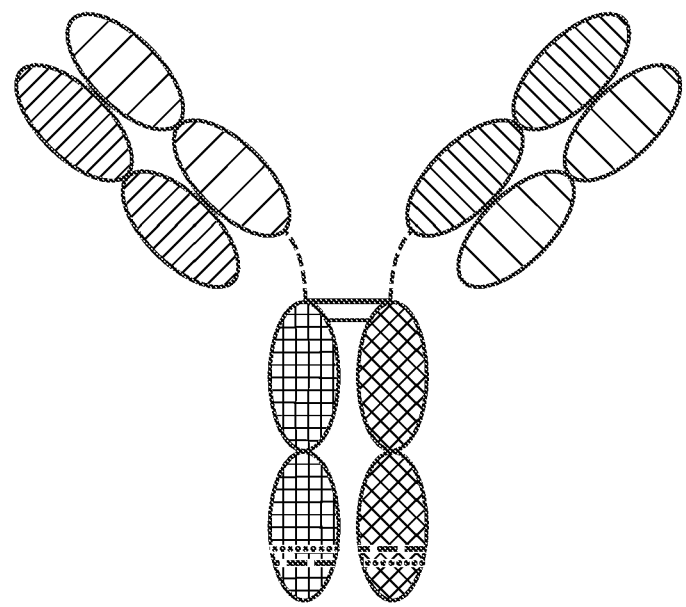
FIG. 24 is a representation of a TriNKET in the SEED Body form, which is an heterodimer containing 2 Fabs binding to target 1 and 2, and an Fc stabilized by heterodimerization mutations.
Figure 25:
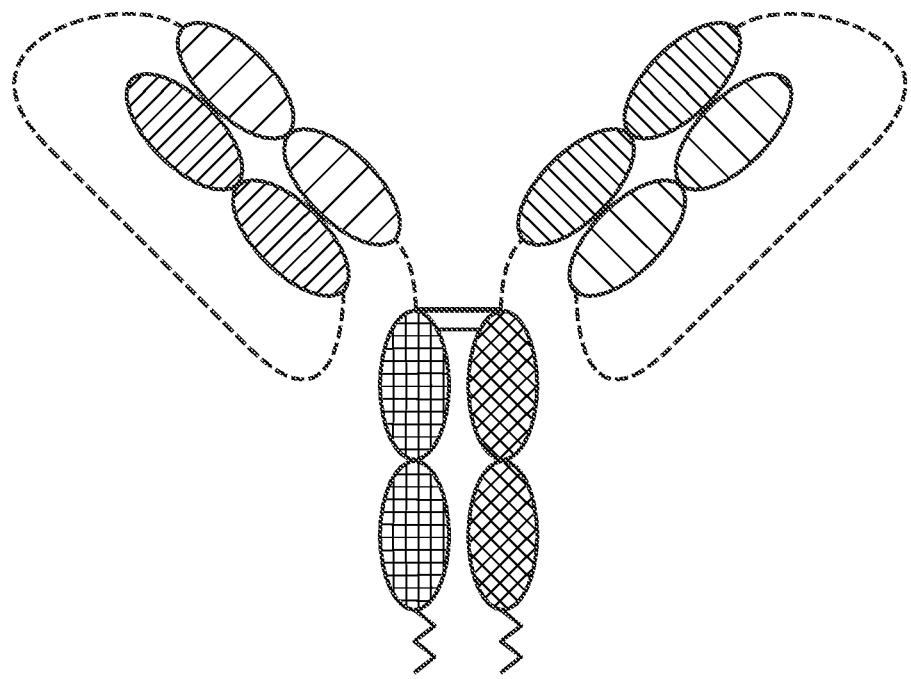
FIG. 25 is a representation of a TriNKET in the LuZ-Y form, in which leucine zipper is used to induce heterodimerization of two different HCs. LuZ-Y form is a heterodimer containing 2 different scFabs binding to target 1 and 2, fused to Fc. Heterodimerization is ensured through leucine zipper motifs fused to C-terminus of Fc.
Figure 26:
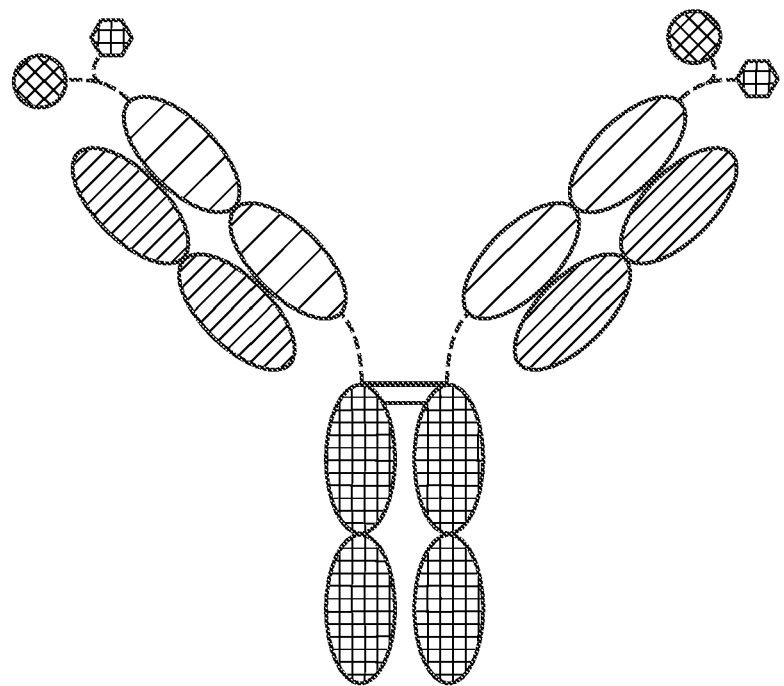
FIG. 26 is a representation of a TriNKET in the Cov-X-Body form.
Figure 27A:
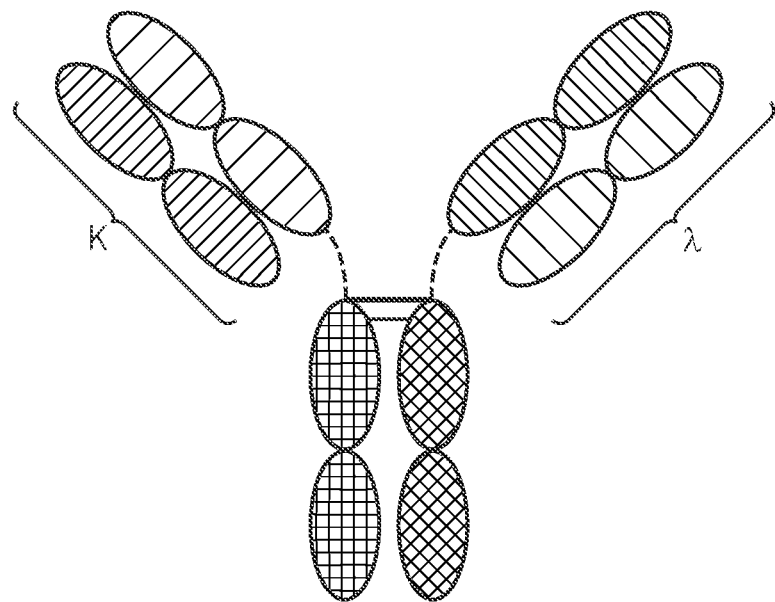
FIGS. 27A-27B are representations of TriNKETs in the κλ-Body forms, which are an heterodimeric constructs with 2 different Fabs fused to Fc stabilized by heterodimerization mutations: Fab1 targeting antigen 1 contains kappa LC, while second Fab targeting antigen 2 contains lambda LC.
Figure 27B:
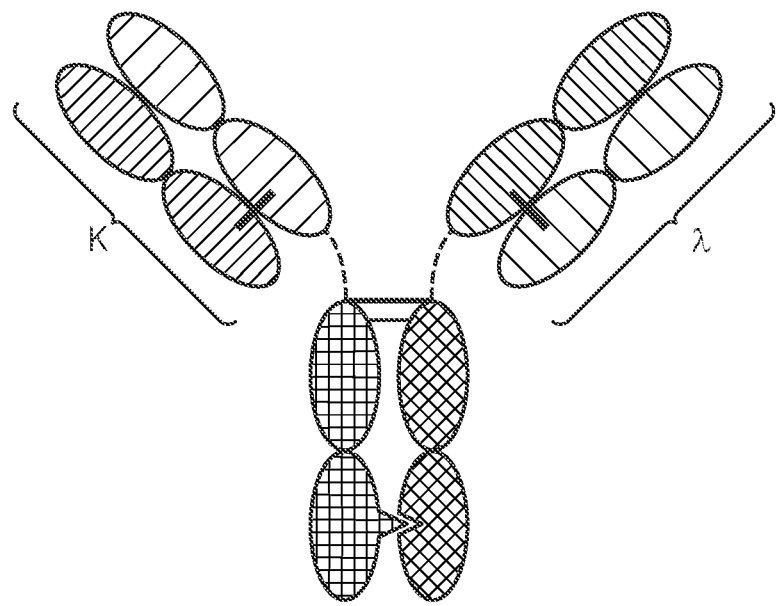
Figure 28:
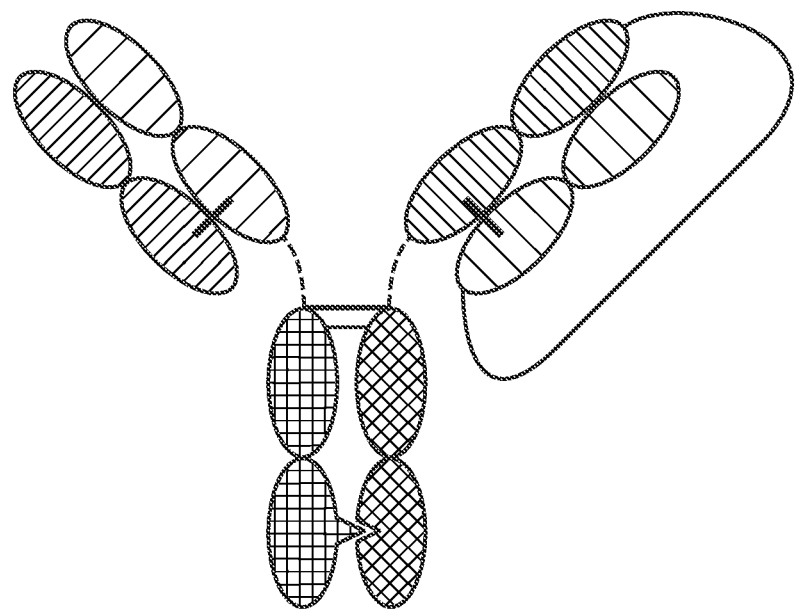
FIG. 28 is an Oasc-Fab heterodimeric construct that includes Fab binding to target 1 and scFab binding to target 2 fused to Fc. Heterodimerization is ensured by mutations in the Fc.
Figure 29:
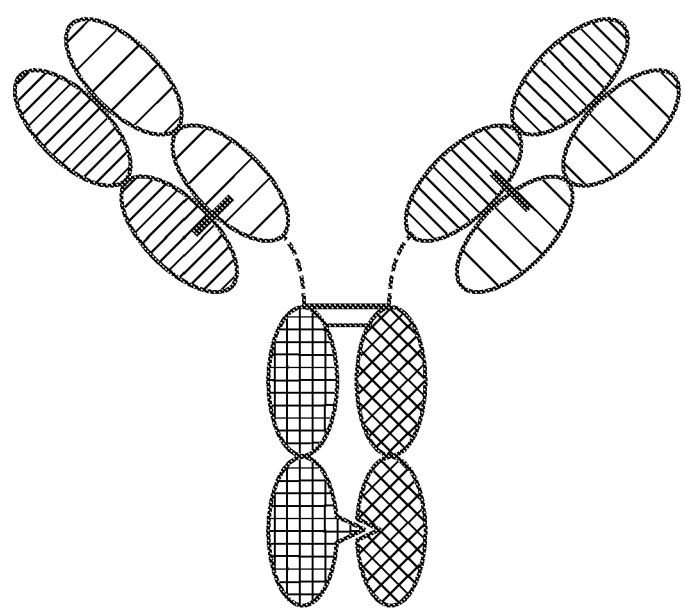
FIG. 29 is a DuetMab, which is an heterodimeric construct containing 2 different Fabs binding to antigen 1 and 2 and Fc stabilized by heterodimerization mutations. Fab 1 and 2 contain differential S-S bridges that ensure correct LC and HC pairing.
Figure 30:
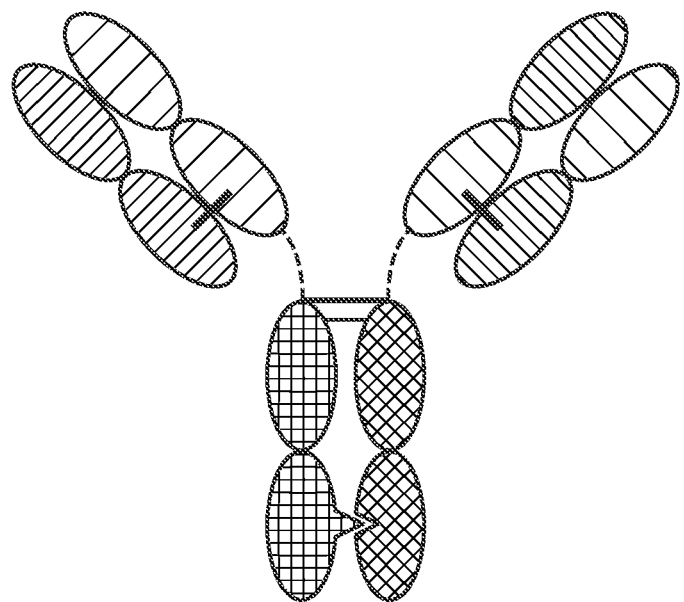
FIG. 30 is a CrossmAb, which is an heterodimeric construct with 2 different Fabs binding to Target 1 and 2 fused to Fc stabilized by heterodimerization. CL and CH1 domains and VH and VL domains are switched, e.g., CH1 is fused in-line with VL, while CL is fused in-line with VH.
Figure 31:
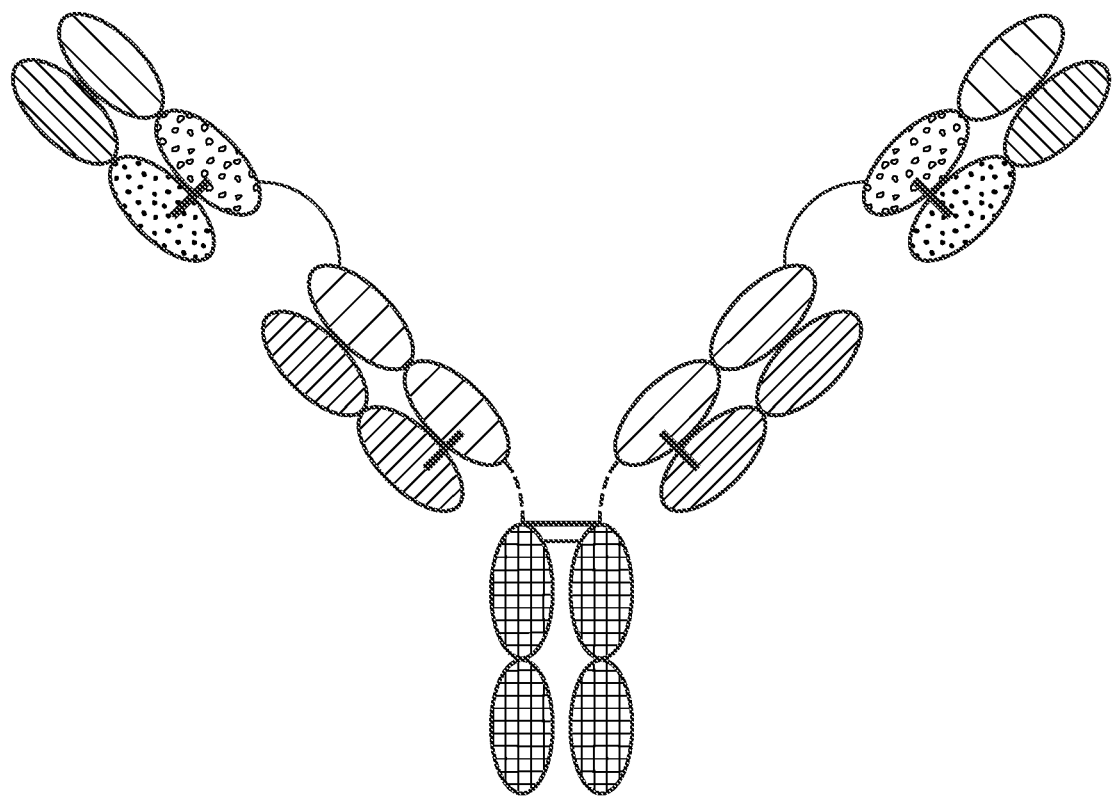
FIG. 31 is a Fit-Ig, which is an homodimeric constructs where Fab binding to antigen 2 is fused to the N terminus of HC of Fab that binds to antigen 1. The construct contains wild-type Fc.

TriNKETs mediate cytotoxicity of human NK cells against the HER2-positive 786-O human renal cell carcinoma cell line. As shown in FIG. 15, rested human NK cells were mixed with 786-O cancer cells, and TriNKETs are able to enhance the cytotoxic activity of rested human NK cells in a dose-responsive manor against the cancer cells (each TriNKET was added at 5, 1, 0.2 µg/ml in the assay and the results are represented in 3 columns from the left to the right in each TriNKET in the FIGS. 15-16). Dotted line indicates the cytotoxic activity of rested NK cells against 786-O cells in the absence of TriNKETs. As shown in FIG. 16, activated human NK cells were mixed with 786-O cells, and TriNKETs enhance the cytotoxic activity of activated human NK cells even further in a dose-responsive manor against the cancer cells. Dotted line indicates the cytotoxic activity of activated NK cells against 786-O cells in the absence of TriNKETs.

Example 7—Variants of ADI-27749 and TriNKETs Containing the Variants

As described above, ADI-27749 (A49) contains, inter alia, a heavy chain CDR3 having the amino acid sequence of GAPMGAAAGWFDP (SEQ ID NO:71). The Met at position 102 of SEQ ID NO:7 (i.e., at position 4 of this CDR3 sequence) may be replaced by Gln, Leu, Ile, Phe, or Val, thereby generating NKG2D antibodies A49MQ, A49ML, A49MI, A49MF, and A49MV, respectively, having the corresponding heavy chain variable region, light chain variable region, and CDR sequences provided in Table 1.

The effects of these mutations on hydrophobicity were analyzed using the MOE2018.01 program using the parameter setting of avg_pro_patch_cdr_hyd. Residues were mutated using the protein builder module and entire Fab was minimized after tethering all residues. Dynamic property sampling was performed using the lowMD protocol in BIOMOE. As shown in Table 11, these mutations did not have a substantial negative effect on the predicted hydrophobicity of the A49 Fab.

TABLE 11

| Amino acid residue | avg_pro_patch_cdr_hyd |
| --- | --- |
| M | 524.0968 |
| L | 529.67743 |
| I | 551.93549 |
| V | 477.09677 |
| Q | 447.09677 |
| F | 542.25806 |

The hydrophobicity of a TriNKET containing A49 ("TriNKET A") and a mutant form of TriNKET A having a substitution of Ile, Leu, Val, Gln, or Phe for the Met ("TriNKET A*") were tested by analytical hydrophobic interaction chromatography (HIC). Each of the TriNKETs also bound to a first tumor antigen. As shown in Table 12, the retention time of TriNKET A* was similar to that of TriNKET A.

TABLE 12

| Protein | Retention time |
| --- | --- |
| TriNKET A* | 8.6 min |
| TriNKET A | 8.65 ± 0.05 min |

Thermal stability of TriNKET A and TriNKET A* was examined by differential scanning calorimetry analysis (DSC) in 20 mM Histidine, 260 mM sucrose, and 0.005% PS-80 at pH 6.0. The values of the $T_m$ are shown in Table 13, where $T_m$ is the midpoint transition temperature of an individual domain. The M102 mutation had a small effect on the $T_m$ values of the two most stable transitions ($T_{m3}$ and $T_{m4}$) by shifting them 0.6 and 0.7° C. lower, compared to the TriNKET A. The earlier transitions ($T_{m1}$ and $T_{m2}$) were unaffected. Therefore, the M102 mutation had only a marginal effect on the overall thermal stability of TriNKET A.

TABLE 13

| Protein | $T_m1$ | $T_m2$ | $T_m3$ | $T_m4$ |
| --- | --- | --- | --- | --- |
| TriNKET A | 66.2 | 80.2 | 86.3 | 88.4 |
| TriNKET A* | 66.2 | 80.5 | 85.7 | 87.7 |

Figure 32:
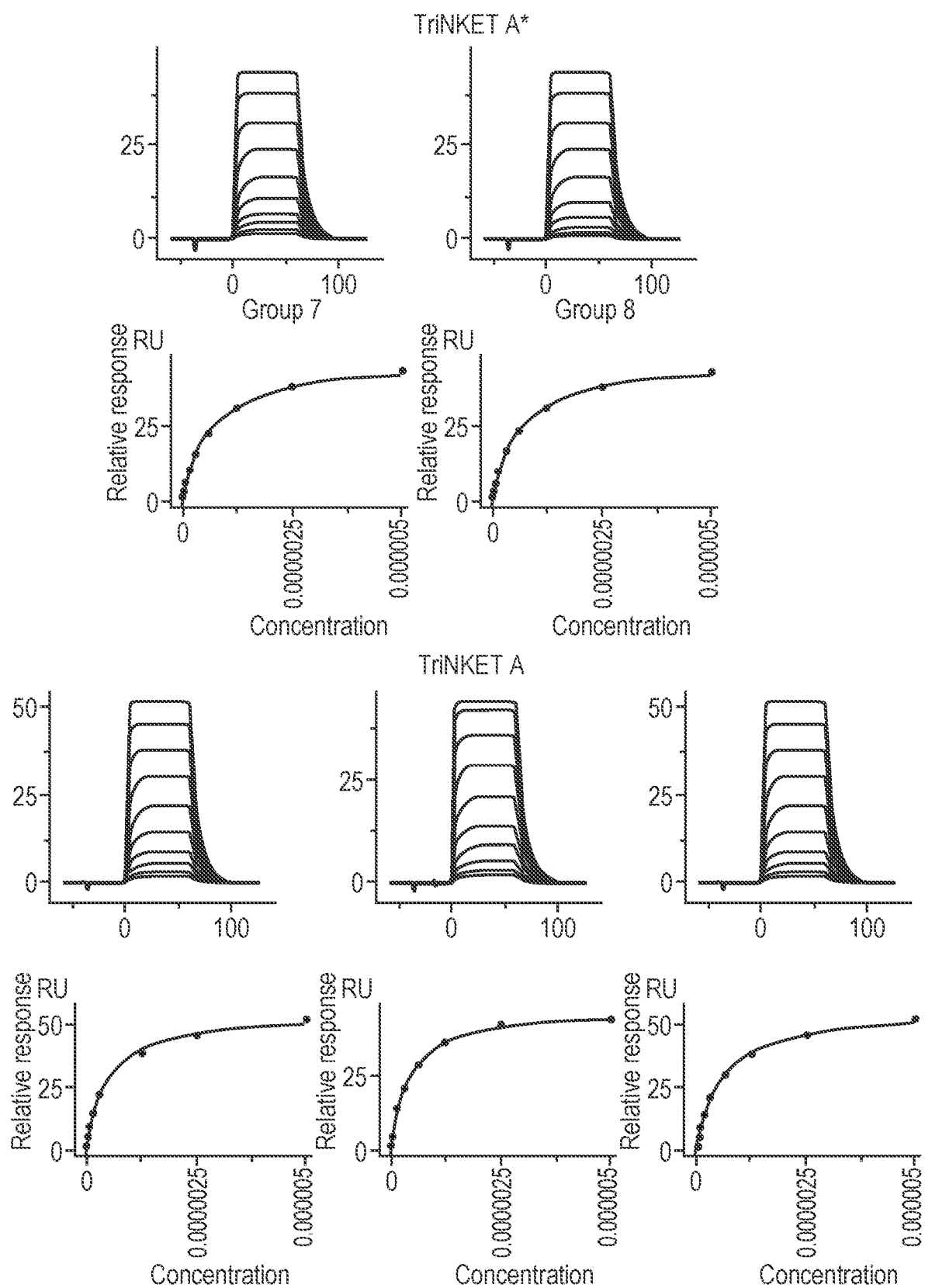
FIG. 32 is a series of line graphs showing the binding of TriNKET A* and TriNKET A to human NKG2D as tested by SPR. The upper panels represent kinetic fit, and the lower panels represent steady state affinity fit.

Binding of TriNKET A and TriNKET A* to a fusion protein of human NKG2D and murine Fc ("mFc-hNKG2D") was characterized by surface plasmon resonance (SPR) at 37° C. Two different fits, steady state affinity fit and kinetic fit, were utilized to obtain the equilibrium affinity data (FIG. 32). The kinetic constants and equilibrium affinity constants were calculated, and data from the two independent experiments for TriNKET A* and the three independent experiments for TriNKET A were averaged.

TABLE 14

| Capture | Analyte | $k_a$ (1/Ms) | $k_d$ (1/s) | Kinetics $K_D$ (M) | Steady State Affinity $K_D$ (M) | Stoichiometry |
|---|---|---|---|---|---|---|
| mFc-hNKG2D | TriNKET A* | $1.41 \times 10^5$ | $1.31 \times 10^{-1}$ | $9.31 \times 10^{-7}$ | $6.98 \times 10^{-7}$ | 0.86 |
| mFc-hNKG2D | TriNKET A* | $1.56 \times 10^5$ | $1.28 \times 10^{-1}$ | $8.19 \times 10^{-7}$ | $6.76 \times 10^{-7}$ | 0.85 |
| | Average | $1.49 \times 10^5$ | $1.30 \times 10^{-1}$ | $8.75 \times 10^{-7}$ | $6.87 \times 10^{-7}$ | 0.85 |
| mFc-hNKG2D | TriNKET A | $1.91 \times 10^5$ | $1.16 \times 10^{-1}$ | $6.05 \times 10^{-7}$ | $4.62 \times 10^{-7}$ | 1.01 |
| mFc-hNKG2D | TriNKET A | $2.03 \times 10^5$ | $1.06 \times 10^{-1}$ | $5.23 \times 10^{-7}$ | $4.20 \times 10^{-7}$ | 0.88 |
| mFc-hNKG2D | TriNKET A | $1.93 \times 10^5$ | $1.15 \times 10^{-1}$ | $5.95 \times 10^{-7}$ | $5.80 \times 10^{-7}$ | 1.25 |
| | Average ± stdev | $(1.96 \pm 0.06) \times 10^5$ | $(1.12 \pm 0.06) \times 10^{-1}$ | $(5.74 \pm 0.45) \times 10^{-7}$ | $(4.87 \pm 0.83) \times 10^{-7}$ | $1.01 \pm 0.11$ |

As shown in Table 14, the equilibrium affinity constants ($K_D$) obtained from both the affinity and kinetic fits were very similar between the replicates, which suggested a high confidence in the measured parameters. The M102 variant has less than 2-fold reduced affinity for human NKG2D compared to TriNKET A. The $K_D$ for TriNKET A* was $(6.87 \pm 0.16) \times 10^{-7}$ M, while the $K_D$ for TriNKET A was $(4.87 \pm 0.83) \times 10^{-7}$ M (calculated from the affinity fit). Similar differences in affinities were observed when $K_D$ was calculated from the kinetic fit. The stoichiometry of NKG2D binding to TriNKET A* was $0.85 \pm 0.12$, similar to the $1.01 \pm 0.11$ for TriNKET A, confirming that each NKG2D dimer binds to one molecule of TriNKET A*. This suggests that the M102 mutation had only a minor effect on the binding of an A49-containing TriNKET to human NKG2D.

Finally, the effect of the M102 mutation on the potency of TriNKETs was assessed in a cytotoxicity assay. Briefly, KHYG-1 cells expressing the high-affinity variant of CD16a (158V) were generated through retroviral transduction. Following transduction, cells were selected in puromycin-containing growth media to generate a selected population of KHYG-1-CD16V cells. The selected population was maintained in media containing 10 ng/mL human IL-2. To prepare the KHYG-1-CD16V cells for use as effectors in cytotoxicity assays, the cells were harvested from culture, pelleted, washed three times in culture media without IL-2, and resuspended in culture media without IL-2 and rested for 24 hours.

Human cancer cell lines expressing a target of interest were harvested from culture. The cells were washed with HBS, and were resuspended in growth media at $10^6$ cells/mL for labeling with BATDA reagent (Perkin Elmer C136-100). Manufacturer instructions were followed for labeling of the target cells. After labeling, the cells were washed three times with HBS and were resuspended at $0.5 \times 10^5$ cells/mL in culture media. 100 µl of BATDA labeled cells were added to each well of a 96-well plate.

TriNKETs were serially diluted in culture media, and 50 µl of a diluted TriNKET was added to each well. Rested NK cells were harvested from culture, washed, and resuspended at $1.0 \times 10^6$ cells/mL in culture media. 50 µl of NK cells were added to each well of the plate to attain a desired E:T ratio of 10:1 and to make a total of 200 µl culture volume in each well. The plate was incubated at 37° C. with 5% $CO_2$ for 2-3 hours.

After the culturing, the plate was removed from the incubator, and the cells were pelleted by centrifugation at 200×g for 5 minutes. 20 µl of culture supernatant was transferred to a clean microplate provided from the manufacturer. Supernatant from the labeled cells incubated alone without NK cells was used to measure spontaneous release of TDA. Supernatant from labeled cells incubated with 1% Triton-X was used to measure maximum lysis of the target cells. Supernatant from the labeled cells prior to the 2-3 hours of incubation was used to measure the background and for quality control purposes.

200 µl of room temperature europium solution (Perkin Elmer C135-100) was added to each well containing culture supernatant. The plate was protected from light and incubated on a plate shaker at 250 rpm for 15 minutes. Fluorescence was measured using a SpectraMax i3X instrument. The fluorescent levels represented lysis of the target cells. The values of % specific lysis were calculated as: % specific lysis=((Experimental release −Spontaneous release)/(Maximum release−Spontaneous release))×100%.

Figure 33:
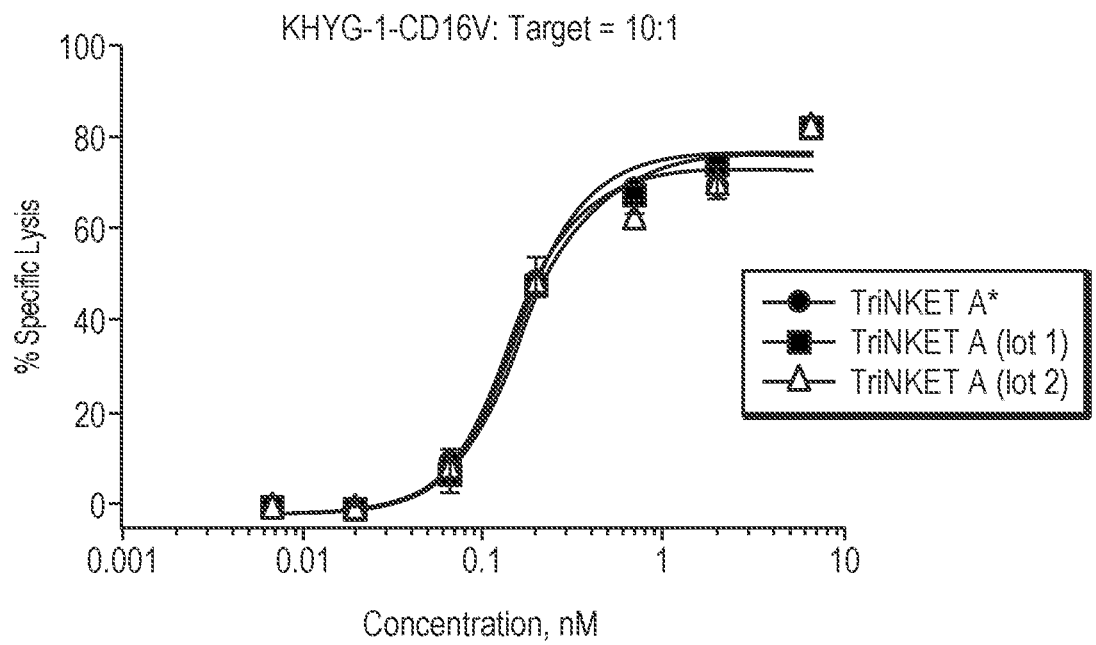
FIG. 33 is a line graph showing the potency of TriNKET A and TriNKET A* in mediating cytotoxicity of NK cells against target cells.

To measure the activity of TriNKET A and TriNKET A*, a cell line that expressed the first tumor antigen was selected as target cells. Two different lots of TriNKET A were used for comparison. The % specific lysis values were plotted in FIG. 33, and the EC50 and maximum % specific lysis values were summarized in Table 15. The EC50 and maximum % specific lysis values of TriNKET A* were similar to those of TriNKET A, suggesting that the M102 mutation did not affect the biological activity of TriNKET A.

TABLE 15

| Protein | $EC_{50}$ (nM) | Max lysis (%) |
|---|---|---|
| TriNKET A* | 0.15 | 73 |
| TriNKET A - lot 1 | 0.17 | 76 |
| TriNKET A - lot 2 | 0.15 | 76 |

Figure 34:
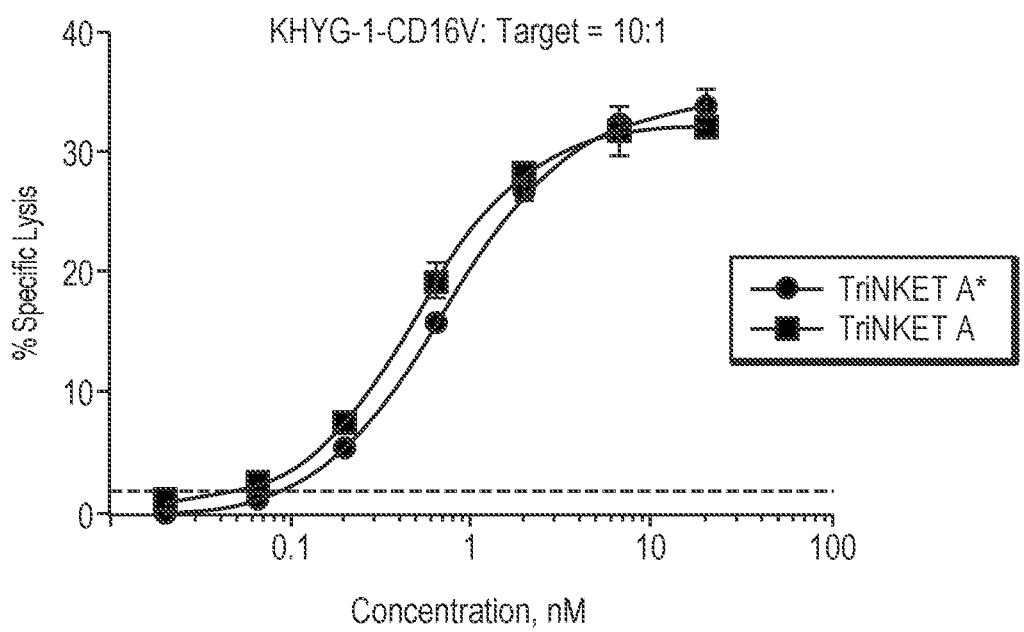
FIG. 34 is a line graph showing the potency of TriNKET A and TriNKET A* in mediating cytotoxicity of NK cells against target cells.

To confirm that the absence of effect of the M102 mutation on TriNKET activity was not tumor antigen-specific, TriNKET A and TriNKET A* that bind to a second, different tumor antigen were constructed. The activity of the two TriNKETs were compared in cytotoxicity assays using a cell line that expressed the second tumor antigen as target cells and KHYG-1-CD16V cells as effector cells. As shown in FIG. 34, TriNKET A* demonstrated equivalent activity to TriNKET A.

INCORPORATION BY REFERENCE

The entire disclosure of each of the patent documents and scientific articles referred to herein is included by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

What is claimed is:

1. An antigen-binding site that binds NKG2D, comprising an antibody heavy chain variable domain comprising a complementarity-determining region 1 (CDR1) sequence represented by the amino acid sequence of SEQ ID NO:48, a complementarity-determining region 2 (CDR2) sequence represented by the amino acid sequence of SEQ ID NO:30, and a complementarity-determining region 3 (CDR3) sequence represented by the amino acid sequence of SEQ ID NO:78, SEQ ID NO:74, SEQ ID NO:76, SEQ ID NO: 80, or SEQ ID NO:82; and an antibody light chain variable domain comprising
    a CDR1 sequence identical to the amino acid sequence of SEQ ID NO:32, a CDR2 sequence identical to the amino acid sequence of SEQ ID NO:33, and a CDR3 sequence identical to the amino acid sequence of SEQ ID NO:34.

2. The antigen-binding site according to claim 1, binding to NKG2D with a $K_D$ of 10-62 nM, as measured by surface plasmon resonance.

3. A protein comprising the antigen-binding site according to claim 1 and an additional antigen-binding site.

4. The protein according to claim 3, wherein the additional antigen-binding site binds to a tumor-associated antigen.

5. The protein according to claim 4, wherein the tumor-associated antigen is selected from the group consisting of HER2, EpCAM, CD2, CD20, CD30, CD38, CD40, CD52, CD70, EGFR/ERBB1, IGF1R, HER3/ERBB3, HER4/ERBB4, MUC1, SLAMF7, PSCA, MICA, MICB, TRAILR1, TRAILR2, MAGE-A3, B7.1, B7.2, CTLA4, and PD1.

6. The protein according to claim 3, wherein the additional antigen-binding site comprises an antibody heavy chain variable domain; and
    wherein the antibody heavy chain variable domain of the antigen-binding site that binds NKG2D is present on a first polypeptide further comprising a first antibody constant region, and the antibody heavy chain variable domain of the additional antigen-binding site is present on a second polypeptide further comprising a second antibody constant region.

7. The protein according to claim 6, wherein the first antibody constant region and the second antibody constant region:
   a. form a complex capable of binding CD16;
   b. each comprise hinge, CH2, and CH3 domains;
   c. each comprise CH1 hinge, CH2, and CH3 domains; and/or
   d. are each at least 90% identical to human IgG1 constant region.

8. The protein according to claim 7, wherein:
the amino acid sequence of the first antibody constant region differs from the amino acid sequence of an IgG1 constant region by a Y349C substitution and wherein the amino acid sequence of the second antibody constant region differs from the amino acid sequence of an IgG1 constant region by an S354C substitution; and/or
the amino acid sequence of the first antibody constant region differs from the amino acid sequence of an IgG1 constant region by K360E and K409W substitutions and wherein the amino acid sequence of the second antibody constant region differs from the amino acid sequence of an IgG1 constant region by Q347R, D399V and F405T substitutions.

9. The protein according to claim 3, wherein the protein further comprises an antigen-binding site capable of binding CD16.

10. A formulation comprising the protein according to claim 3 and a pharmaceutically acceptable carrier.

11. The antigen-binding site according to claim 1, wherein the CDR1, CDR2, and CDR3 sequences of the heavy chain variable domain are represented by the amino acid sequences of SEQ ID NOs: 48, 30, and 78, respectively, and the CDR1, CDR2, and CDR3 sequences of the light chain variable domain are represented by the amino acid sequences of SEQ ID NOs: 32, 33, and 34, respectively.

12. The antigen-binding site according to claim 11, wherein the antibody heavy chain variable domain comprises an amino acid sequence at least 95% identical to SEQ ID NO:85, and the antibody light chain variable domain comprises an amino acid sequence at least 95% identical to SEQ ID NO:8.

13. The antigen-binding site according to claim 1, wherein the antibody heavy chain variable domain comprises the amino acid sequence of SEQ ID NO: 85, 83, 84, 86, or 41, and the antibody light chain variable domain comprises the amino acid sequence of SEQ ID NO:8.

14. The antigen-binding site according to claim 1, wherein the antibody heavy chain variable domain comprises the amino acid sequence of SEQ ID NO:85, and the antibody light chain variable domain comprises the amino acid sequence of SEQ ID NO:8.

* * * * *

```
                        SEQUENCE LISTING

<160> NUMBER OF SEQ ID NOS: 86

<210> SEQ ID NO 1
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Ala Pro Asn Tyr Gly Asp Thr Thr His Asp Tyr Tyr Tyr
                100                 105                 110

Met Asp Val Trp Gly Lys Gly Thr Thr Val Thr Val Ser Ser
            115                 120                 125

<210> SEQ ID NO 2
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
                20                  25                  30

Leu Ala Trp Tyr Gln Gln Lys Pro Gly Gln Ala Pro Arg Leu Leu Ile
            35                  40                  45

Tyr Gly Ala Ser Thr Arg Ala Thr Gly Ile Pro Ala Arg Phe Ser Gly
        50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asp Asp Trp Pro Phe
                85                  90                  95

Thr Phe Gly Gly Gly Thr Lys Val Glu Ile Lys
                100                 105

<210> SEQ ID NO 3
```

<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Thr Gly Glu Tyr Tyr Asp Thr Asp Asp His Gly Met Asp
            100                 105                 110

Val Trp Gly Gln Gly Thr Thr Val Thr Val Ser Ser
        115                 120

<210> SEQ ID NO 4
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Asp Asp Tyr Trp Pro Pro
                85                  90                  95

Thr Phe Gly Gly Gly Thr Lys Val Glu Ile Lys
            100                 105

<210> SEQ ID NO 5
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Glu Val Gln Leu Leu Glu Ser Gly Gly Gly Leu Val Gln Pro Gly Gly
1               5                   10                  15

```
Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Gly Gly Tyr Tyr Asp Ser Gly Ala Gly Tyr Trp Gly
                100                 105                 110

Gln Gly Thr Leu Val Thr Val Ser Ser
            115                 120

<210> SEQ ID NO 6
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Asp Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Val Ser Tyr Pro Arg
                85                  90                  95

Thr Phe Gly Gly Gly Thr Lys Val Glu Ile Lys
                100                 105

<210> SEQ ID NO 7
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80
```

```
Leu Gln Met Asn Ser Leu Arg Ala Glu Asp Thr Ala Val Tyr Tyr Cys
                85                  90                  95

Ala Arg Gly Ala Pro Met Gly Ala Ala Gly Trp Phe Asp Pro Trp
            100                 105                 110

Gly Gln Gly Thr Leu Val Thr Val Ser Ser
        115                 120

<210> SEQ ID NO 8
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Val Ser Phe Pro Arg
                85                  90                  95

Thr Phe Gly Gly Gly Thr Lys Val Glu Ile Lys
            100                 105

<210> SEQ ID NO 9
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Gly Ala Gly Phe Ala Tyr Gly Met Asp Tyr Tyr Tyr Met
            100                 105                 110

Asp Val Trp Gly Lys Gly Thr Thr Val Thr Val Ser Ser
        115                 120                 125

<210> SEQ ID NO 10
<211> LENGTH: 107
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Asp Asn Trp Pro Phe
                85                  90                  95

Thr Phe Gly Gly Gly Thr Lys Val Glu Ile Lys
            100                 105

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Tyr Thr Phe Thr Ser Tyr Tyr Met His
1               5

<210> SEQ ID NO 12
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ile Ile Asn Pro Ser Gly Gly Ser Thr Ser Tyr Ala Gln Lys Phe Gln
1               5                   10                  15

Gly

<210> SEQ ID NO 13
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ala Arg Gly Ala Pro Asn Tyr Gly Asp Thr Thr His Asp Tyr Tyr Tyr
1               5                   10                  15

Met Asp Val

<210> SEQ ID NO 14
<211> LENGTH: 11
<212> TYPE: PRT
```

-continued

<213> ORGANISM: Artificial Sequence
<220> FEATURE:
<223> OTHER INFORMATION: Description of Artificial Sequence: Synthetic
peptide

<400> SEQUENCE: 14

Arg Ala Ser Gln Ser Val Ser Ser Asn Leu Ala
1 5 10

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 15

Gly Ala Ser Thr Arg Ala Thr
1 5

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 16

Gln Gln Tyr Asp Asp Trp Pro Phe Thr
1 5

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 17

Tyr Thr Phe Thr Gly Tyr Tyr Met His
1 5

<210> SEQ ID NO 18
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 18

Trp Ile Asn Pro Asn Ser Gly Gly Thr Asn Tyr Ala Gln Lys Phe Gln
1 5 10 15

Gly

<210> SEQ ID NO 19
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 19

Ala Arg Asp Thr Gly Glu Tyr Tyr Asp Thr Asp Asp His Gly Met Asp
1               5                   10                  15
Val

<210> SEQ ID NO 20
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Arg Ala Ser Gln Ser Val Ser Ser Asn Leu Ala
1               5                   10

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gly Ala Ser Thr Arg Ala Thr
1               5

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gln Gln Asp Asp Tyr Trp Pro Pro Thr
1               5

<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Phe Thr Phe Ser Ser Tyr Ala Met Ser
1               5

<210> SEQ ID NO 24
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Ala Ile Ser Gly Ser Gly Gly Ser Thr Tyr Tyr Ala Asp Ser Val Lys
1               5                   10                  15
Gly

<210> SEQ ID NO 25

```
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Ala Lys Asp Gly Gly Tyr Tyr Asp Ser Gly Ala Gly Asp Tyr
1               5                   10

<210> SEQ ID NO 26
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Arg Ala Ser Gln Gly Ile Asp Ser Trp Leu Ala
1               5                   10

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Ala Ala Ser Ser Leu Gln Ser
1               5

<210> SEQ ID NO 28
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Gln Gln Gly Val Ser Tyr Pro Arg Thr
1               5

<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Phe Thr Phe Ser Ser Tyr Ser Met Asn
1               5

<210> SEQ ID NO 30
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30
```

```
Ser Ile Ser Ser Ser Ser Ser Tyr Ile Tyr Tyr Ala Asp Ser Val Lys
1               5                   10                  15

Gly

<210> SEQ ID NO 31
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Ala Arg Gly Ala Pro Met Gly Ala Ala Ala Gly Trp Phe Asp Pro
1               5                   10                  15

<210> SEQ ID NO 32
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Arg Ala Ser Gln Gly Ile Ser Ser Trp Leu Ala
1               5                   10

<210> SEQ ID NO 33
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Ala Ala Ser Ser Leu Gln Ser
1               5

<210> SEQ ID NO 34
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Gln Gln Gly Val Ser Phe Pro Arg Thr
1               5

<210> SEQ ID NO 35
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Tyr Thr Phe Thr Ser Tyr Tyr Met His
1               5

<210> SEQ ID NO 36
<211> LENGTH: 17
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 36

Ile Ile Asn Pro Ser Gly Gly Ser Thr Ser Tyr Ala Gln Lys Phe Gln
1               5                   10                  15

Gly

<210> SEQ ID NO 37
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Ala Arg Glu Gly Ala Gly Phe Ala Tyr Gly Met Asp Tyr Tyr Tyr Met
1               5                   10                  15

Asp Val

<210> SEQ ID NO 38
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Arg Ala Ser Gln Ser Val Ser Ser Tyr Leu Ala
1               5                   10

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Asp Ala Ser Asn Arg Ala Thr
1               5

<210> SEQ ID NO 40
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gln Gln Ser Asp Asn Trp Pro Phe Thr
1               5

<210> SEQ ID NO 41
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 41

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Ala Pro Val Gly Ala Ala Ala Gly Trp Phe Asp Pro Trp
            100                 105                 110

Gly Gln Gly Thr Leu Val Thr Val Ser Ser
        115                 120

<210> SEQ ID NO 42
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: VARIANT
<222> LOCATION: (102)..(102)
<223> OTHER INFORMATION: Met, Leu, Ile, Val, Gln or Phe

<400> SEQUENCE: 42

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Ala Pro Xaa Gly Ala Ala Ala Gly Trp Phe Asp Pro Trp
            100                 105                 110

Gly Gln Gly Thr Leu Val Thr Val Ser Ser
        115                 120

<210> SEQ ID NO 43
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: VARIANT
<222> LOCATION: (6)..(6)
<223> OTHER INFORMATION: Met, Leu, Ile, Val, Gln or Phe

<400> SEQUENCE: 43

Ala Arg Gly Ala Pro Xaa Gly Ala Ala Ala Gly Trp Phe Asp Pro
1               5                   10                  15

<210> SEQ ID NO 44
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: VARIANT
<222> LOCATION: (4)..(4)
<223> OTHER INFORMATION: Met, Leu, Ile, Val, Gln or Phe

<400> SEQUENCE: 44

Gly Ala Pro Xaa Gly Ala Ala Ala Gly Trp Phe Asp Pro
1               5                   10

<210> SEQ ID NO 45
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Ser Tyr Tyr Met His
1               5

<210> SEQ ID NO 46
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Gly Tyr Tyr Met His
1               5

<210> SEQ ID NO 47
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Ser Tyr Ala Met Ser
1               5

<210> SEQ ID NO 48
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Ser Tyr Ser Met Asn
1               5

<210> SEQ ID NO 49
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 49

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Val Val His Trp Val Arg Gln Ala Pro Gly Gln Gly Leu Glu Trp Met
            35                  40                  45

Gly Tyr Ile Asn Pro Tyr Asn Asp Gly Thr Lys Tyr Asn Glu Lys Phe
        50                  55                  60

Lys Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Tyr Arg Tyr Glu Val Tyr Gly Met Asp Tyr Trp Gly Gln
                100                 105                 110

Gly Thr Leu Val Thr Val Ser Ser
            115                 120

<210> SEQ ID NO 50
<211> LENGTH: 106
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 50

Asp Ile Val Leu Thr Gln Ser Pro Ala Ser Leu Ala Val Ser Pro Gly
1               5                   10                  15

Gln Arg Ala Thr Ile Thr Cys Thr Ala Ser Ser Ser Val Asn Tyr Ile
                20                  25                  30

His Trp Tyr Gln Gln Lys Pro Gly Gln Pro Pro Lys Leu Leu Ile Tyr
            35                  40                  45

Asp Thr Ser Lys Val Ala Ser Gly Val Pro Ala Arg Phe Ser Gly Ser
        50                  55                  60

Gly Ser Gly Thr Asp Phe Thr Leu Thr Ile Asn Pro Val Glu Ala Asn
65                  70                  75                  80

Asp Thr Ala Asn Tyr Tyr Cys Gln Gln Trp Arg Ser Tyr Pro Leu Thr
                85                  90                  95

Phe Gly Gln Gly Thr Lys Leu Glu Ile Lys
                100                 105

<210> SEQ ID NO 51
<211> LENGTH: 117
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 51

Gln Val Gln Leu Gln Gln Trp Gly Ala Gly Leu Leu Lys Pro Ser Glu
1               5                   10                  15

```
Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
            115

<210> SEQ ID NO 52
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Gly Ser Phe Ser Gly Tyr Tyr Trp Ser
1               5

<210> SEQ ID NO 53
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Glu Ile Asp His Ser Gly Ser Thr Asn Tyr Asn Pro Ser Leu Lys Ser
1               5                   10                  15

<210> SEQ ID NO 54
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Ala Arg Ala Arg Gly Pro Trp Ser Phe Asp Pro
1               5                   10

<210> SEQ ID NO 55
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
```

```
                    20                  25                  30
Leu Ala Trp Tyr Gln Gln Lys Pro Gly Lys Ala Pro Lys Leu Leu Ile
            35                  40                  45

Tyr Lys Ala Ser Ser Leu Glu Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asp Thr Phe Ile Thr
                85                  90                  95

Phe Gly Gly Gly Thr Lys Val Glu Ile Lys
            100                 105
```

<210> SEQ ID NO 56
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

```
Arg Ala Ser Gln Ser Ile Ser Ser Trp Leu Ala
1               5                   10
```

<210> SEQ ID NO 57
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

```
Lys Ala Ser Ser Leu Glu Ser
1               5
```

<210> SEQ ID NO 58
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

```
Gln Gln Tyr Asp Thr Phe Ile Thr
1               5
```

<210> SEQ ID NO 59
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

```
Gln Val His Leu Gln Glu Ser Gly Pro Gly Leu Val Lys Pro Ser Glu
1               5                   10                  15

Thr Leu Ser Leu Thr Cys Thr Val Ser Asp Asp Ser Ile Ser Ser Tyr
            20                  25                  30

Tyr Trp Ser Trp Ile Arg Gln Pro Pro Gly Lys Gly Leu Glu Trp Ile
        35                  40                  45
```

```
Gly His Ile Ser Tyr Ser Gly Ser Ala Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Asn Trp Asp Asp Ala Phe Asn Ile Trp Gly Gln Gly Thr Met Val Thr
            100                 105                 110

Val Ser Ser
    115

<210> SEQ ID NO 60
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Ser Tyr Tyr Trp Ser
1               5

<210> SEQ ID NO 61
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

His Ile Ser Tyr Ser Gly Ser Ala Asn Tyr Asn Pro Ser Leu Lys Ser
1               5                   10                  15

<210> SEQ ID NO 62
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Trp Asp Asp Ala Phe Asn Ile
1               5

<210> SEQ ID NO 63
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60
```

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gly Gly Thr Lys Val Glu Ile Lys
            100                 105

<210> SEQ ID NO 64
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Arg Ala Ser Gln Ser Val Ser Ser Ser Tyr Leu Ala
1               5                   10

<210> SEQ ID NO 65
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Gly Ala Ser Ser Arg Ala Thr
1               5

<210> SEQ ID NO 66
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Gln Gln Tyr Gly Ser Ser Pro Trp Thr
1               5

<210> SEQ ID NO 67
<211> LENGTH: 193
<212> TYPE: PRT
<213> ORGANISM: Homo sapiens

<400> SEQUENCE: 67

Arg Arg Asp Asp Pro His Ser Leu Cys Tyr Asp Ile Thr Val Ile Pro
1               5                   10                  15

Lys Phe Arg Pro Gly Pro Arg Trp Cys Ala Val Gln Gly Gln Val Asp
                20                  25                  30

Glu Lys Thr Phe Leu His Tyr Asp Cys Gly Asn Lys Thr Val Thr Pro
            35                  40                  45

Val Ser Pro Leu Gly Lys Lys Leu Asn Val Thr Met Ala Trp Lys Ala
        50                  55                  60

Gln Asn Pro Val Leu Arg Glu Val Val Asp Ile Leu Thr Glu Gln Leu
65                  70                  75                  80

Leu Asp Ile Gln Leu Glu Asn Tyr Thr Pro Lys Glu Pro Leu Thr Leu
                85                  90                  95

Gln Ala Arg Met Ser Cys Glu Gln Lys Ala Glu Gly His Ser Ser Gly

```
                    100                 105                 110
Ser Trp Gln Phe Ser Ile Asp Gly Gln Thr Phe Leu Leu Phe Asp Ser
        115                 120                 125

Glu Lys Arg Met Trp Thr Thr Val His Pro Gly Ala Arg Lys Met Lys
    130                 135                 140

Glu Lys Trp Glu Asn Asp Lys Asp Val Ala Met Ser Phe His Tyr Ile
145                 150                 155                 160

Ser Met Gly Asp Cys Ile Gly Trp Leu Glu Asp Phe Leu Met Gly Met
                165                 170                 175

Asp Ser Thr Leu Glu Pro Ser Ala Gly Ala Pro Leu Ala Met Ser Ser
                180                 185                 190

Gly

<210> SEQ ID NO 68
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Gly Ala Pro Asn Tyr Gly Asp Thr Thr His Asp Tyr Tyr Tyr Met Asp
1               5                   10                  15

Val

<210> SEQ ID NO 69
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Asp Thr Gly Glu Tyr Tyr Asp Thr Asp Asp His Gly Met Asp Val
1               5                   10                  15

<210> SEQ ID NO 70
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Asp Gly Gly Tyr Tyr Asp Ser Gly Ala Gly Asp Tyr
1               5                   10

<210> SEQ ID NO 71
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Gly Ala Pro Met Gly Ala Ala Ala Gly Trp Phe Asp Pro
1               5                   10

<210> SEQ ID NO 72
```

```
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Glu Gly Ala Gly Phe Ala Tyr Gly Met Asp Tyr Tyr Tyr Met Asp Val
1               5                   10                  15

<210> SEQ ID NO 73
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Ala Arg Gly Ala Pro Gln Gly Ala Ala Ala Gly Trp Phe Asp Pro
1               5                   10                  15

<210> SEQ ID NO 74
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Gly Ala Pro Gln Gly Ala Ala Ala Gly Trp Phe Asp Pro
1               5                   10

<210> SEQ ID NO 75
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Ala Arg Gly Ala Pro Leu Gly Ala Ala Ala Gly Trp Phe Asp Pro
1               5                   10                  15

<210> SEQ ID NO 76
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Gly Ala Pro Leu Gly Ala Ala Ala Gly Trp Phe Asp Pro
1               5                   10

<210> SEQ ID NO 77
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77
```

Ala Arg Gly Ala Pro Ile Gly Ala Ala Ala Gly Trp Phe Asp Pro
1               5                   10                  15

<210> SEQ ID NO 78
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Gly Ala Pro Ile Gly Ala Ala Ala Gly Trp Phe Asp Pro
1               5                   10

<210> SEQ ID NO 79
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Ala Arg Gly Ala Pro Phe Gly Ala Ala Ala Gly Trp Phe Asp Pro
1               5                   10                  15

<210> SEQ ID NO 80
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Gly Ala Pro Phe Gly Ala Ala Ala Gly Trp Phe Asp Pro
1               5                   10

<210> SEQ ID NO 81
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Ala Arg Gly Ala Pro Val Gly Ala Ala Ala Gly Trp Phe Asp Pro
1               5                   10                  15

<210> SEQ ID NO 82
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Gly Ala Pro Val Gly Ala Ala Ala Gly Trp Phe Asp Pro
1               5                   10

<210> SEQ ID NO 83
<211> LENGTH: 122
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 83

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Ala Pro Gln Gly Ala Ala Ala Gly Trp Phe Asp Pro Trp
            100                 105                 110

Gly Gln Gly Thr Leu Val Thr Val Ser Ser
        115                 120

<210> SEQ ID NO 84
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Ala Pro Leu Gly Ala Ala Ala Gly Trp Phe Asp Pro Trp
            100                 105                 110

Gly Gln Gly Thr Leu Val Thr Val Ser Ser
        115                 120

<210> SEQ ID NO 85
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr

```
                    20                  25                  30
Ser Met Asn Trp Val Arg Gln Ala Pro Gly Lys Gly Leu Glu Trp Val
                35                  40                  45

Ser Ser Ile Ser Ser Ser Ser Tyr Ile Tyr Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Ala Pro Ile Gly Ala Ala Ala Gly Trp Phe Asp Pro Trp
            100                 105                 110

Gly Gln Gly Thr Leu Val Thr Val Ser Ser
            115                 120

<210> SEQ ID NO 86
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
                35                  40                  45

Ser Ser Ile Ser Ser Ser Ser Tyr Ile Tyr Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Ala Pro Phe Gly Ala Ala Ala Gly Trp Phe Asp Pro Trp
            100                 105                 110

Gly Gln Gly Thr Leu Val Thr Val Ser Ser
            115                 120
```